US010208350B2

(12) United States Patent
Beim et al.

(10) Patent No.: US 10,208,350 B2
(45) Date of Patent: Feb. 19, 2019

(54) METHODS AND SYSTEMS FOR ASSESSING INFERTILITY AND RELATED PATHOLOGIES

(71) Applicant: Celmatix Inc., New York, NY (US)

(72) Inventors: Piraye Yurttas Beim, New York, NY (US); David Emlyn Parfitt, New York, NY (US); Michael Elashoff, Redwood City, CA (US)

(73) Assignee: Celmatix Inc., New York, NY (US)

( * ) Notice: Subject to any disclaimer, the term of this patent is extended or adjusted under 35 U.S.C. 154(b) by 0 days.

(21) Appl. No.: 14/802,609

(22) Filed: Jul. 17, 2015

(65) Prior Publication Data

US 2016/0017426 A1 Jan. 21, 2016

Related U.S. Application Data

(60) Provisional application No. 62/065,416, filed on Oct. 17, 2014, provisional application No. 62/025,802, filed on Jul. 17, 2014.

(51) Int. Cl.
*C12Q 1/6883* (2018.01)
*G06F 19/20* (2011.01)

(52) U.S. Cl.
CPC ...... *C12Q 1/6883* (2013.01); *C12Q 2600/112* (2013.01); *C12Q 2600/158* (2013.01); *G06F 19/20* (2013.01)

(58) Field of Classification Search
None
See application file for complete search history.

(56) References Cited

U.S. PATENT DOCUMENTS

| 4,683,195 | A | 7/1987 | Mullis et al. |
| 5,510,270 | A | 4/1996 | Fodor et al. |
| 5,539,083 | A | 7/1996 | Cook et al. |
| 5,556,752 | A | 9/1996 | Lockhart et al. |
| 5,578,832 | A | 11/1996 | Trulson et al. |
| 6,028,189 | A | 2/2000 | Blanchard |
| 6,214,558 | B1 | 4/2001 | Shuber et al. |
| 6,300,077 | B1 | 10/2001 | Shuber et al. |
| 6,566,101 | B1 | 5/2003 | Shuber et al. |
| 6,818,395 | B1 | 11/2004 | Quake et al. |
| 6,890,763 | B2 | 5/2005 | Jackowski et al. |
| 6,925,389 | B2 | 8/2005 | Hitt et al. |
| 6,989,100 | B2 | 1/2006 | Norton |
| 7,169,560 | B2 | 1/2007 | Lapidus et al. |
| 7,211,390 | B2 | 5/2007 | Rothberg et al. |
| 7,244,559 | B2 | 7/2007 | Rothberg et al. |
| 7,264,929 | B2 | 9/2007 | Rothberg et al. |
| 7,282,337 | B1 | 10/2007 | Harris |
| 7,323,305 | B2 | 1/2008 | Leamon et al. |
| 7,335,762 | B2 | 2/2008 | Rothberg et al. |
| 7,531,635 | B2 | 5/2009 | Nelson et al. |
| 7,666,593 | B2 | 2/2010 | Lapidus |
| 9,177,098 | B2 | 11/2015 | Elashoff et al. |
| 2002/0127555 | A1* | 9/2002 | Baban .......... C12Q 1/6883 435/6.17 |
| 2002/0164629 | A1 | 11/2002 | Quake et al. |
| 2003/0027208 | A1* | 2/2003 | Horwitz ........ C12Q 1/6886 435/7.1 |
| 2005/0214836 | A1 | 9/2005 | Nakamura et al. |
| 2006/0172322 | A1 | 8/2006 | Nakabayashi et al. |
| 2006/0195269 | A1 | 8/2006 | Yeatman et al. |
| 2009/0026082 | A1 | 1/2009 | Rothberg et al. |
| 2009/0127589 | A1 | 5/2009 | Rothberg et al. |
| 2009/0137478 | A1 | 5/2009 | Bernstein et al. |
| 2009/0156412 | A1 | 6/2009 | Boyce, IV et al. |
| 2009/0191565 | A1 | 7/2009 | Lapidus et al. |
| 2010/0035252 | A1 | 2/2010 | Rothberg et al. |
| 2010/0036192 | A1 | 2/2010 | Yao et al. |
| 2010/0081135 | A1 | 4/2010 | Dorak et al. |
| 2010/0137143 | A1 | 6/2010 | Rothberg et al. |
| 2010/0188073 | A1 | 7/2010 | Rothberg et al. |
| 2010/0197507 | A1 | 8/2010 | Rothberg et al. |
| 2010/0282617 | A1 | 11/2010 | Rothberg et al. |
| 2010/0300559 | A1 | 12/2010 | Schultz et al. |

(Continued)

FOREIGN PATENT DOCUMENTS

| EP | 1484399 A1 | 12/2004 |
| EP | 1947195 A1 | 7/2008 |

(Continued)

OTHER PUBLICATIONS

Swanson, 2002, The rapid evolution of reproductive proteins, Nat Rev Genet 3:137-44.
Talkowski, 2012, Sequencing Chromosomal Abnormalities Reveals Neurodevelopmental Loci that Confer Risk across Diagnostic Boundaries, Cell 149:525-37.
Tanwar, 2008, "In vivo evidence of role of bone morphogenetic protein-4 in the mouse ovary," Anim Reprod Sci 106 (3-4):232-40.
Teixeira Filho, 2002, "Aberrant expression of growth differentiation factor-9 in oocytes of women with polycystic ovary syndrome," J Clin Endocrinol Metab 87(3):1337-44.
Telford, 1990, Transition from maternal to embryonic control in early mammalian development: a comparison of several species, Mol Reprod Dev 26:90-100.
Thompson, 1998, Mouse embryos do not wait for the MBT: chromatin and RNA polymerase remodeling in genome activation at the onset of development, Dev Genet 22:31-42.

(Continued)

*Primary Examiner* — Catherine S Hibbert
(74) *Attorney, Agent, or Firm* — Brown Rudnick LLP; Thomas C. Meyers

(57) ABSTRACT

Methods for assessing infertility and related pathologies and informing treatment type and timing thereof are provided. According to certain embodiments, methods of the invention include determining levels of one or more transcripts present in a sample obtained from a subject suspected of having endometriosis, identifying transcript levels that correspond to a regulation pattern specific to a time-point in a uterine cycle, and characterizing endometriosis of the subject based upon the identified transcript levels. The invention includes methods for assessing age-associated increase in aneuploidy rates based on FSH levels and IVF success rates based on obesity in PCOS patients.

17 Claims, 13 Drawing Sheets

(56) References Cited

U.S. PATENT DOCUMENTS

| | | |
|---|---|---|
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0071033 A1 | 3/2011 | Yurttas et al. |
| 2011/0166029 A1 | 7/2011 | Margulies et al. |
| 2012/0094845 A1 | 4/2012 | Yurttas et al. |
| 2013/0109583 A1 | 5/2013 | Beim |
| 2014/0107934 A1 | 4/2014 | Elashoff et al. |
| 2014/0171337 A1 | 6/2014 | Beim |
| 2014/0186839 A1 | 7/2014 | Margulies et al. |
| 2014/0337052 A1 | 11/2014 | Pellini et al. |
| 2015/0038778 A1* | 2/2015 | Guerrier ............ G01N 33/6893 600/34 |
| 2015/0142331 A1 | 5/2015 | Beim et al. |
| 2015/0211068 A1 | 7/2015 | Beim et al. |
| 2016/0017426 A1 | 1/2016 | Beim et al. |
| 2016/0078172 A1 | 3/2016 | Elashoff et al. |

FOREIGN PATENT DOCUMENTS

| | | | |
|---|---|---|---|
| JP | 2004-533229 A | 11/2004 | |
| WO | 2001/005935 A2 | 1/2001 | |
| WO | 2001/05935 A2 | 1/2001 | |
| WO | 2002/081492 A1 | 10/2002 | |
| WO | 03/011326 A1 | 2/2003 | |
| WO | 2006/055761 A1 | 5/2006 | |
| WO | 2008/109147 A2 | 9/2008 | |
| WO | 2009/109043 A1 | 9/2009 | |
| WO | 2010/147714 A1 | 12/2010 | |
| WO | 2011031786 A2 | 3/2011 | |
| WO | 2011/133175 A1 | 10/2011 | |
| WO | 2013/052505 A2 | 4/2013 | |
| WO | 2014/062393 A1 | 4/2014 | |
| WO | 2015/112972 A1 | 7/2015 | |
| WO | 2016011377 A1 | 1/2016 | |

OTHER PUBLICATIONS

Tian, 2009, Evolution and functional divergence of NLRP genes in mammalian reproductive systems, BMC Evol Biol 9:202.

Tian, 2009, Gene Birth, Death, and Divergence: The Different Scenarios of Reproduction Related Gene Evolution, Biology of Reproduction 80:616-21.

Tokushige, 2006, High density of small nerve fibres in the functional layer of the endometrium in women with endometriosis, Human Reproduction 21(3):782-87.

Tong, 1999, "A mouse gene encoding an oocyte antigen associated with autoimmune premature ovarian failure," Endocrinology 140(8):3720-6.

Tong, 2000, "Mater encodes a maternal protein in mice with a leucine-rich repeat domain homologous to porcine ribonuclease inhibitor," Mamm Genome 11(4):281-7.

Tong, 2000, "Mater, a maternal effect gene required for early embryonic development in mice," Nat Genet 26(3):267-8.

Tong, 2002, "A human homologue of mouse Mater, a maternal effect gene essential for early embryonic development," Hum Reprod 17(4):903-11.

Tong, 2004, "Developmental expression and subcellular localization of mouse MATER, an oocyte-specific protein essential for early development," Endocrinology 145(3):1427-34.

Toralova, 2009, "Silencing CENPF in bovine preimplantation embryo induces arrest at 8-cell stage," Reproduction 138(5):783-91.

Tormala, 2008, Zona pellucida components are present in human fetal ovary before follicle formation, Mol Cell Endocrinol 289(1-2):10-15.

Tschopp, 2003, NALPs: a novel protein family involved in inflammation, Nature Rev Molec Cell Biol 4:95-104.

Uda, 2004, "Foxl2 disruption causes mouse ovarian failure by pervasive blockage of follicle development," Hum Mol Genet 13(11):1171-81.

Uhlenhaut, 2006, "Foxl2 function in ovarian development," Mol Genet Metab 88(3):225-34.

Underwood, 1998, "A novel calcium-independent phospholipase A2, cPLA2-gamma, that is prenylated and contains homology to cPLA2," J Biol Chem 273(34):21926-32.

Van Montfoort et al., 2008, "Differential gene expression in cumulus cells as a prognostic indicator of embryo viability: a microarray analysis," HMR-Basic Science of Reproductive Medicine, 14(3):157-168.

Vatansever, 2005, "Changed Bcl:Bax ratio in endometrium of patients with unexplained infertility," Acta Histochem 107(5):345-55.

Velasco, 1999, Cloning and Characterization of Human MMP-23, a New Matrix Metalloproteinase Predominantly Expressed in Reproductive Tissues and Lacking Conserved Domains in Other Family Members, Journal of Biological Chemistry 274:4570-76.

Velculescu, 1995, Serial analysis of gene expression, Science 270:484-87.

Velculescu, 1997, Characterization of the Yeast Transcriptome, Cell, 88:243 51.

Venners, 2006, "Urinary estrogen and progesterone metabolite concentrations in menstrual cycles of fertile women with non-conception, early pregnancy loss or clinical pregnancy," Human Reprod 21(9):2272-80.

Vernet, 1992, Changes in permissiveness for the expression of microinjected DNA during the first cleavages of mouse embryos, Mech Dev 36:129-39.

Vitale, 2007, "Proteomic profiling of murine oocyte maturation," Mol Reprod Dev 74(5):608-16.

Vitt, 2001, "Stage-dependent role of growth differentiation factor-9 in ovarian follicle development," Mol Cell Endocrinol 183(1-2)171-7.

Vogt, 2009, "Aurora kinase B, epigenetic state of centromeric heterochromatin and chiasma resolution in oocytes," Reprod Biomed Online 19(3):352-68.

Wan, 2008, "Maternal depletion of CTCF reveals multiple functions during oocyte and preimplantation embryo development," Development 135(16):2729-38.

Wang, 1996, "Purification and biochemical heterogeneity of the mammalian SWI-SNF complex," EMBO J 15(19):5370-82.

Wang, 2006, Search for basonuclin target genes, Biochemical and Biophysical Research Communications 348:1261-71.

Watkins, 2006, "An investigation into FOXE1 polyalanine tract length in premature ovarian failure," Mol Hum Reprod 12(3):145-9.

Weis, 1992, Detection of rare mRNAs via quantitative RT-PCR, Trends in Genetics 8:263-64.

Wilcoxon, 1945, "Individual comparisons by ranking methods," Biometrics Bulletin 1(6):80-83.

Wright, 2003, "ePAD, an oocyte and early embryo-abundant peptidylarginine deiminase-like protein that localizes to egg cytoplasmic sheets," Dev Biol 256(1):73-88.

Wu, 2003, "Zygote arrest 1 (Zar1) is a novel maternal-effect gene critical for the oocyte-to-embryo transition," Nat Genet 33(2):187-91.

Wu, 2009, "Maternal depletion of NLRP5 blocks early embryogenesis in rhesus macaque monkeys (*Macaca mulatta*)," Hum Reprod 24(2):415-24.

Xiao, 1999, "HSF1 is required for extra-embryonic development, postnatal growth and protection during inflammatory responses in mice," EMBO J 18(21):5943-52.

Yan, 2005, "Mice deficient in oocyte-specific oligoadenylate synthetase-like protein OAS1D display reduced fertility," Mol Cell Biol 25(11):4615-24.

Yang, 2001, "BADGE, BeadsArray for the Detection of Gene Expression, a High-Throughput Diagnostic Bioassay," Genome Res 11:1888-98.

Yang, 2008, "Towards a transgenic model of Huntington's disease in a non-human primate," Nature 453:921-24.

Yang, 2008, "Parental effect of DNA (Cytosine-5) methyltransferase 1 on grandparental-origin-dependent transmission ratio distortion in mouse crosses and human families," Genetics 178(1):35-45.

Yeung, 2001, "Principal component analysis for clustering gene expression data," Bioinformatics 17(9):763-74.

(56) References Cited

OTHER PUBLICATIONS

Youngson, 2011, A missense mutation in the transcription factor Foxo3a causes teratomas and oocyte abnormalities in mice, Mammalian Genome 22:235-48.
Yu & Bradley, 2001, "Mouse genomic technologies: engineering chromosomal rearrangements in mice," Nature Reviews Genetics 2:780-90.
Yurttas, 2008, "Role for PADI6 and the cytoplasmic lattices in ribosomal storage in oocytes and translational control in the early mouse embryo," Development 135(15):2627-36.
Yurttas, 2010, Use of proteomics to identify highly abundant maternal factors that drive the egg-to-embryo transition, Reproduction 139:809-23.
Zhang, 2005, "Localization of mitotic arrest deficient 1 (MAD1) in mouse oocytes during the first meiosis and its functions as a spindle checkpoint protein," Biol Reprod 72(1):58-68.
Dong, 1996, "Growth differentiation factor-9 is required during early ovarian folliculogenesis," Nature 383(6600):531-5.
Doolin, 2002, Maternal Genetic Effects, Exerted by Genes Involved in Homocysteine Remethylation Influence, Am J of Human Genet 71(5):1222-26.
Dube, 1998, "The bone morphogenetic protein 15 gene is X-linked and expressed in oocytes," Mol Endocrinol 12(12):1809-17.
Egholm, 1993,PNA hybridizes to complementary oligonucleotides obeying the Watson-Crick hydrogen-bonding rules, Nature 365:566-68.
Eisen, 1998, "Cluster analysis and display of genome-wide expression patterns," PNAS 95(25):14863-68.
Elnakat & Ratnam, 2006, Role of folate receptor genes in reproduction and related cancers, Frontiers in Bioscience 11:506-19.
Ertunc, 2005, Glutathione-S-transferase P1 gene polymorphism and susceptibility to endometriosis, Human Reprod 20(8):2157-61.
Esposito, 2007, "Peptidylarginine deiminase (PAD) 6 is essential for oocyte cytoskeletal sheet formation and female fertility," Mol Cell Endocrinol 273(1-2):25-31.
Evans, 2008, "Prokineticin 1 signaling and gene regulation in early human pregnancy," Endocrinology 149(6):2877-87.
Ferguson, 1996, High-Density Fiber-Optic DNA Random Microsphere Array, Nature Biotech. 14:1681-84.
Ferguson, 2000, High-Density Fiber Optic DNA Random Microsphere Array, Analytical Chemistry 72:5618.
Fodor, 1991, Light-directed, spatially addressable parallel chemical synthesis, Science 251:767-773.
Fogli, 2003, "Ovarian failure related to eukaryotic initiation factor 2B mutations," Am J Hum Genet 72(6):1544-50.
Friedman, 1937, "The use of ranks to avoid the assumption of normality implicit in the analysis of variance," J Amer Stat Assoc 32(200):675-701.
Froehler, 1986, Synthesis of DNA via deoxynudeoside H-phosphonate Intermediates, Nucleic Acids Res 14:5399-5407.
Fu 2010, Clathrin recruits phosphorylated TACC3 to spindle poles for bipolar spindle assembly and chromosome alignment, J. Cell. Sci. 123:3645-51.
Fujimoto, 2010, Highdensity lipoprotein metabolism and the human embryo, Human Reproduction Update 16, 25 20-38.
Fukumura, 2003, A sensitive transcriptome analysis method that can detect unknown transcripts, Nucl. Acids. Res. 31(16):e94.
Galan-Caridad, 2007, "Zfx controls the self-renewal of embryonic and hematopoietic stem cells," Cell 129(2):345-57.
Galloway, 2000, "Mutations in an oocyte-derived growth factor gene (BMP15) cause increased ovulation rate and infertility in a dosage-sensitive manner," Nat Genet 25(3):279-83.
Garcia-Cruz, 2009, "ATR, BRCA1 and gammaH2AX localize to unsynapsed chromosomes at the pachytene stage in human oocytes," Reprod Biomed Online 18(1):37-44.
Genuis, 2012, J of Environmental & Public Health, article ID 185731, 10 pages.
Gonzalo, 2006, DNA methyltransferases control telomere length and telomere recombination in mammalian cells, Nat. Cell Biol. 8:416-24.
Greenfeld, 2007, "BAX is involved in regulating follicular growth, but is dispensable for follicle atresia in adult mouse ovaries," Reproduction 133(1):107-16.
Greenfeld, 2007, "BAX regulates follicular endowment in mice," Reproduction 133(5):865-76.
Grigorova, 2007, "Haplotype structure of FSHB, the beta-subunit gene for fertility-associated follicle-stimulating hormone:possible influence of balancing selection," Ann Hum Genet 71(Pt 1):18-28.
Gurtu, 2002, "Maternal effect for DNA mismatch repair in the mouse," Genetics 160(1):271-7.
Guzman, 2006, Cystathionine beta-synthase is essential for female reproductive function, Hum Mol Genet 15(21):3168-76.
Halperin, 2008, "Prolactin signaling through the short form of its receptor represses forkhead transcription factor FOXO3 and its target gene gait causing a severe ovarian defect," Mol Endocrinol 22(2):513-22.
Hao, 2002, "TACC3 expression and localization in the murine egg and ovary," Mol Reprod Dev 63(3):291-9.
Hardison, 1997, Long human-mouse sequence alignments reveal novel regulatory elements: a reason to sequence the mouse genome, Genome Res 7:959-66.
Hardouin & Nagy, 2000, Mouse models for human disease, Clinical Genetics 57(4):237-44.
Harris, 2005, "INHA promoter polymorphisms are associated with premature ovarian failure," Mol Hum Reprod 11(11):779-84.
Harris, 2008, Single-Molecule DNA Sequencing of a Viral Genome, Science 320:106-109.
Hawkins, 2011, Functional MicroRNA Involved in Endometriosis, Molecular Endocrinology 25(5):821-32.
Heid, 1996, Real Time Quantitative PCR, Genome Research 6:986-994.
Herr, 2008, "Distribution of RNA binding protein MOEP19 in the oocyte cortex and early embryo indicates pre-patterning related to blastomere polarity and trophectoderm specification," Dev Biol 314(2):300-16.
Hirasawa, 2008, Maternal and zygotic Dnmt1 are necessary and sufficient for the maintenance of DNA methylation imprints during preimplantation development, Genes Dev 22(12):1607-16.
Hod, 1992, A simplified ribonuclease protection assay, Biotechniques 13(6):852-54.
Hollingsworth, 2004, Mucins in cancer: protection and control of the cell surface, Nature Rev Cancer 4(1):45-60.
Horn, 1995, "A member of the caudal family of homeobox genes maps to the X-inactivation centre region of the mouse and human X chromosomes," Hum Mol Genet 4(6):1041-7.
Howe, 2011, "Limitation of inverse probability-of-censoring weights in estimating survival in the presence of strong selection bias," Am J Epidmiology 173:569-77.
Howell, 2001, "Genomic imprinting disrupted by a maternal effect mutation in the Dnmt1 gene," Cell 104(6):829-38.
Hu, 2007, "p53 regulates maternal reproduction through LIF," Nature 450(7170):721-4.
Hu, 2008, "p53:a new player in reproduction," Cell Cycle 7(7):848-52.
Hu, 2010, FIGLA, a Basic Helix-Loop-Helix Transcription Factor, Balances Sexually Dimorphic Gene Expression in Postnatal Oocytes, Mol Cell Biol, 30(14):3661-67.
Huber, 2004, matchprobes: a Bioconductor package for the sequence-matching of microarray probe elements, Bioinformatics 20(10):1651-52.
Hughes, 2001, Expression profiling using microarrays fabricated by an ink-jet oligonucleotide synthesizer, Nat Biotech 19:342-47.
Huntriss, 2002, "Isolation, characterization and expression of the human Factor in the Germline alpha (FIGLA) gene in ovarian follicles and oocytes," Mol Hum Reprod 8(12):1087-95.
Huntriss, 2006, "cDNA cloning and expression of the human NOBOX gene in oocytes and ovarian follicles," Mol Hum Reprod 12(5):283-9.
Zhang, 2007, Distinct sets of developmentally regulated genes that are expressed by human oocytes and human embryonic stem cells, Fertil Steril 87(3):677-90.

(56) References Cited

OTHER PUBLICATIONS

Zhang 2008, "Expression analysis of the NLRP gene family suggests a role in human preimplantation development," PLoS One 3(7):e2755.
Zhang, 2009, "Proteomic-based identification of maternal proteins in mature mouse oocytes," BMC Genomics 10:348.
Zhao 2008, "Transcription factor FIGLA is mutated in patients with premature ovarian failure," Am J Hum Genet 82 (6):1342-8.
Zheng, 2007, Oocyte-Specific Genes Affect Folliculogenesis, Fertilization, and Early Development, Semin Reprod Med 25(4):243-51.
Zheng, 2009, "Role of Filia, a maternal effect gene, in maintaining euploidy during cleavage-stage mouse embryogenesis," Proc Natl Acad Sci U S A 106(18)1473-8.
Zuccotti, 2008, Maternal Oct-4 is a potential key regulator of the developmental competence of mouse oocytes, BMC Dev Biol 8:97.
Zuccotti, 2009, "Oct-4 regulates the expression of Stella and Foxj2 at the Nanog locus:implications for the developmental competence of mouse oocytes," Hum Reprod 24(9):2225-37.
Zuccotti, 2009, Role of Oct-4 during acquisition of developmental competence in mouse oocyte, Reprod Biomed Online 19 Suppl 3:57-62.
Australian Patent Examination Report No. 1 for App. No. 2010351560, dated Apr. 22, 2014, 5 pages.
International Preliminary Report on Patentability for PCT/US10/50063, dated Oct. 23, 2012, 6 pages.
International Preliminary Report on Patentability for PCT/US12/58492, dated Jan. 23, 2013, 6 pages.
International Search Report and Written Opinion for PCT/US10/50063, dated Feb. 3, 2011, 9 pages.
International Search Report and Written Opinion for PCT/US12/58492, dated Jan. 24, 2013, 7 pages.
International Search Report and Written Opinion for PCT/US13/63381, dated Dec. 16, 2013, 10 pages.
Supplementary European Search Report for EP10850395.4, dated Sep. 2, 2013.
Rupp & Locker, 1987, Purification and analysis of RNA from paraffin-embedded tissues, Lab Invest 56:A67.
Sha, G., et al. "Differentially expressed genes in human endometrial endothelial cells derived from eutopic endometrium of patients with endometriosis compared with those from patients without endometriosis." Human reproduction 22.12 (2007): 3159-3169.
Crispi, Stefania, et al. "Transcriptional profiling of endometriosis tissues identifies genes related to organogenesis defects." Journal of cellular physiology 228.9 (2013): 1927-1934.
Eyster, Kathleen M., et al. "Whole genome deoxyribonucleic acid microarray analysis of gene expression in ectopic versus eutopic endometrium." Fertility and sterility 88.6 (2007): 1505-1533.
Hever, Aniko, et al. "Human endometriosis is associated with plasma cells and overexpression of B lymphocyte stimulator." Proceedings of the National Academy of Sciences 104.30 (2007): 12451-12456.
Hull, M. Louise, et al. "Endometrial-peritoneal interactions during endometriotic lesion establishment." The American Journal of pathology 173.3 (2008): 700-715.
Talbi, S., et al. "Molecular phenotyping of human endometrium distinguishes menstrual cycle phases and underlying biological processes in normo-ovulatory women." Endocrinology 147.3 (2006): 1097-1121.
International Search Report and Written Opinion for PCT/US15/40947 dated Nov. 2, 2015 (15 pages).
Nassieri et al. Elevated Day 3 Serum Follicle Stimulating Hormone And/Or Estradiol May Predict Fetal Aneuploidy. Ferility and Sterility. Apr. 1999, vol. 71, No. 4, pp. 715-718.
International Search Report and Written Opinion for PCT/US2015/012887 dated Jun. 24, 2015 (16 pages).
Crackower et al., 2003, Essential Role of Fkbp6 in Male Fertility and Homologous Chromosome Pairing in Meiosis, Science 300(5623): 1291-1295.

O'Bryan et al, 2006, Mouse models for genes involved in impaired spermatogenesis, International Journal of Andrology, 29(1): 76-88.
Yatsenko et al, 2010, The power of mouse genetics to review study spermatogenesis, J. Androl., 31(1): 34-44.
Yurttas et al, 2013, Personalized reproductive medicine on the brink: progress, opportunities and challenges ahead, Reproductive BioMedicine Online 27: 611-623.
Freudenberg et al, 2002, A similarity-based method for genome-wide prediction of disease-relevant human genes, Bioinformatics, Suppl 2:S110-5.
Ford et al., Mutation Res., vol. 313, p. 153-164 (1994).
International Search Report and the Written Opinion of the International Searching Authority for PCT/US13/63381, dated Dec. 16, 2013, 11 pages.
Oh, 1997, "Spindlin, a major maternal transcript expressed in the mouse during the transition from oocyte to embryo," Development 124:493-503.
Ohsugi, 2008, "Maternally derived FILIA-MATER complex localizes asymmetrically in cleavage-stage mouse embryos," Development 135(2)259-69.
Okuwaki, 2012, Function of homo- and hetero-oligomers of human nucleoplasmin/nucleophosmin family proteins NPM1, NPM2 and NPM3 during sperm chromatin remodeling, Nucleic Acids Res 40(11):4861-78.
Oliphant, 2002, "BeadArray Technology: Enabling an Accurate Cost-Effective Approach to High-Throughput Genotyping," Discovery of Markers for Disease, Biotechniques 32:s56-61.
Palmer, 1990, "Comparison of human ZFY and ZFX transcripts," Proc Natl Acad Sci U S A 87(5):1681-5.
Park, 2006, Genetic approach to identify critical factors for mouse early embryogenesis, Integrative Biosciences 10:41-47.
Parker & Barnes, 1999, mRNA: Detection by In Situ and Northern Hybridization, Methods in Molecular Biology 106:247-83.
Parry, 2011, Mutations Causing Familial Biparental Hydatidiform Mole Implicate C6orf221 as a Possible Regulator of Genomic Imprinting in the Human Oocyte, Am J Hum Genet 89(3):451-58.
Pasini, 2004, "Suz12 is essential for mouse development and for EZH2 histone methyltransferase activity," EMBO J 23(20):4061-71.
Patterson, 2003, "Proteomics: the first decade and beyond," Nat Genet Supplement 33:311-23.
Pavlik, 2011, Divergent effects of the 677C>T mutation of the 5,10-methylenetetrahydrofolate reductase (MTHFR) gene on ovarian responsiveness and anti-Müllerian hormone concentrations, Fertility and Sterility 95(7):2257-62.
Payer, 2003, "Stella is a maternal effect gene required for normal early development in mice," Curr Biol 13(23):2110-7.
Paynton, 1994, Polyadenylation and deadenylation of maternal mRNAs during oocyte growth and maturation in the mouse, Molecular Reproduction and Development 37.
Pease, 1994, Light-generated oligonucleotide arrays for rapid DNA sequence analysis, PNAS 91(11):5022-26.
Penny, 1996, "Requirement for Xist in X chromosome inactivation," Nature 379(6561):131-7.
Pittman, 2004, "Integrated modeling of clinical and gene expression information for personalized prediction of disease outcomes," PNAS 101(22):8431-36.
Pozzi, 2009, Maternal polymorphisms for methyltetrahydrofolate reductase and methionine synthetase reductase and risk of children with Down syndrome, Am J Obstet Gynecol 200(6):636.e1-6.
Prueitt, 2000, "Physical mapping of nine Xq translocation breakpoints and identification of XPNPEP2 as a premature ovarian failure candidate gene," Cytogenet Cell Genet 89(1-2):44-50.
Punnonen, 1996, "Increased levels of interleukin-6 and interleukin-10 in the peritoneal fluid of patients with endometriosis," Am J Obstet Gynecol 174(5):1522-6.
Rajkovic, 2002, "The ret finger protein-like 4 gene, Rfpl4, encodes a putative E3 ubiquitin-protein ligase expressed in adult germ cells," Mech Dev 112(1-2):173-7.
Rajkovic, 2004, "NOBOX deficiency disrupts early folliculogenesis and oocyte-specific gene expression," Science 305(5687):1157-9.
Rankin, 1999, "Abnormal zonae pellucidae in mice lacking ZP1 result in early embryonic loss," Development 126(17):3847-55.

(56) References Cited

OTHER PUBLICATIONS

Ratnam, 2002, "Dynamics of Dnmt1 methyltransferase expression and intracellular localization during oogenesis and preimplantation development," Dev Biol 245(2):304-14.
Rosenthal & Brown, 2007, "The mouse ascending: perspectives for human-disease models," Nature Cell Biology 9:993-99.
Roth, 1998, "Finding DNA regulatory motifs within unaligned noncoding sequences clustered by whole-genome mRNA quantitation," Nat Biotechnol 16:939-45.
Rucker, 2000, "Bcl-x and Bax regulate mouse primordial germ cell survival and apoptosis during embryogenesis," Mol Endocrinol 14(7):1038-52.
Ruczinski, 2003, Journal of Computational and Graphical Statistcs 12:475-512.
Rupp & Locker, 1987, "Purification and analysis of RNA from paraffin-embedded tissues," Biotechniques 6(1):56-60.
Sahoo, 2011, Microdeletion of Xq28 involving the AFF2 (FMR2) gene in two unrelated males with developmental delay, Am. J. Med. Genet. A 155A:3110-15.
Salih, 2008, Regulation of catechol O-methyltransferase expression in granulosa cells: a potential role for follicular arrest in polycystic ovary syndrome, Fertility and Sterility 89(5) Supplement:1414-21.
Sanger, 1977, DNA sequencing with chain-terminating inhibitors, Proc.National Academy of Science USA 74(12):5463-7.
Santini, 2003, "Evolutionary conservation of regulatory elements in vertebrate Hox gene clusters," Genome Research 13.6a:1111-22.
Santos, 2002, Dynamic Reprogramming of DNA Methylation in the Early Mouse Embryo, Dev Biol 241(1):172-82.
Saskova, 2008, "Aurora kinase a controls meiosis I progression in mouse oocytes," Cell Cycle 7(15):2368-76.
Sato et al., 2011, Characterization of porcine autism susceptibility candidate 2 as a candidate gene for the number of corpora lutea in pigs, Animal Reproduction Science 126:211-20.
Schena, 1995, Quantitative Monitoring of Gene Expression Patterns with a Complementary DNA Microarray, Science 270:467-70.
Schena, 1996, Parallel human genome analysis: Microarray-based expression monitoring of 1000 genes, PNAS 93:10614-19.
Schmidt, 2011, Prenatal vitamins, one-carbon metabolism gene variants, and risk for autism, Epidemiology 22(4):476-85.
Schneider-Gadicke, 1989, "ZFX has a gene structure similar to ZFY, the putative human sex determinant, and escapes X inactivation," Cell 57(7):1247-58.
Schultz, 1977, Biochemical studies of mammalian oogenesis: protein synthesis during oocyte growth and meiotic maturation in the mouse, Journal of Cell Science 24:167-94.
Schultz, 2002, The molecular foundations of the maternal to zygotic transition in the preimplantation embryo, Hum Reprod Update 8:323-31.
Schumann, 2011, Genome-wide association and genetic functional studies identify autism susceptibility candidate 2 gene (AUTS2) in the regulation of alcohol consumption, Proc. Natl. Acad. Sci. U.S.A. 108:7119-24.
Seydoux, 2006, Pathway to totipotency: lessons from germ cells, Cell 127:891-904.
Shalon, 1996, A DNA microarray system for analyzing cmopelx DNA samples using two-color fluorescent probe hybridization, Genome Res 6:639-45.
Sharan, 2004, "BRCA2 deficiency in mice leads to meiotic impairment and infertility," Development 131(1):131-42.
Soni & Meller, 2007, Progress toward ultrafast DNA sequencing using solid-state nanopores, Clin Chem 53: 1996-2001.
Soyal, 2000, "FIGalpha, a germ cell-specific transcription factor required for ovarian follicle formation," Development 127(21):4645-54.
Stanislawska-Sachadyn, 2010, The transcobalamin (TCN2) 776C>G polymorphism affects homocysteine concentrations among subjects with low vitamin B12 status, Eur J Clin Nutr 64(11):1338-43.
Sturn, 2002, "Genesis: cluster analysis of microarray data," Bioinformatics 18(1):207-08.
Suzumori, 2003, "RFPL4 interacts with oocyte proteins of the ubiquitin-proteasome degradation pathway," Proc Natl Acad Sci U S A 100(2):550-5.
Abrams, 1997, Cognitive, behavioral, and neuroanatomical assessment of two unrelated male children expressing FRAXE, Am. J. Med. Genet. 74:73-81.
Agarwal, 2003, Role of reactive oxygen species in the pathophysiology of human reproduction, Fertility and Sterility 79(4):829-43.
Allingham-Hawkins, 1999, "Fragile X premutation is a significant risk factor for premature ovarian failure: The International collaborative POF in fragile X study—preliminary data," Am J Med Genet 83:322-25.
Amano, 2006, "Identification and targeted disruption of the mouse gene encoding ESG1 (PH34/ECAT2/DPPA5)," BMC Dev Biol 6:11, 9 pages.
Andersson, 2007, "Distinct and cooperative roles of mammalian Vg1 homologs GDF1 and GDF3 during early embryonic development," Dev Biol 311(2):500-11.
Aoki, 1997, Regulation of transcriptional activity during the first and second cell cycles in the preimplantation mouse embryo, Dev Biol 181:296-307.
Arnhold, 2009, "Inactivating mutations of luteinizing hormone beta-subunit or luteinizing hormone receptor cause oligo-amenorrhea and infertility in women," Horm Res 71(2):75-82.
Bachvarova, 1981, Synthesis, turnover, and stability of heterogeneous RNA in growing mouse oocytes, Dev Biol 86:384-92.
Barlow, 1998, "Atm deficiency results in severe meiotic disruption as early as leptonema of prophase I," Development 125(20):4007-17.
Bayne, 2004, "Increased expression of the FIGLA transcription factor is associated with primordial follicle formation in be human fetal ovary," Mol Hum Reprod 10(6):373-81.
Bedell, 1997, "Mouse models of human disease. Part I: Techniques and resources for genetic analysis in mice," Genes and Development 11:1-10.
Bedogni, 2010, Tbr1 regulates regional and laminar identity of postmitotic neurons in developing neocortex, Proceedings of the National Academy of Sciences 107:13129-34.
Benkhalifa, 2010, Imprinting: RNA expression for homocysteine recycling in the human oocyte, Fertility & Sterility 93(5) 1585-90.
Berker, 2009, Homocysteine concentrations in follicular fluid are associated with poor oocyte and embryo qualities in oolycystic ovary syndrome patients undergoing assisted reproduction, Human Reproduction 24(9):2293-2302.
Bione, 1998, "A human homologue of the *Drosophila melanogaster* diaphanous gene is disrupted in a patient with premature ovarian failure:evidence for conserved function in oogenesis and implications for human sterility," Am J Hum Genet 62(3):533-41.
Blackburn, 2000, Metabolic Consequences of Adenosine Deaminase Deficiency in Mice Are Associated with Defects in Alveogenesis, Pulmonary Inflammation, and Airway Obstruction, Journal of Experimental Medicine 192:159-70.
Blanchard, 1996, High-density oligonucleotide arrays, Biosensors & Bioelectronics 11:687-90.
Blanchette, 2002, "Discovery of regulatory elements by a computational method for phylogenetic footprinting," Genome Res 12:739-48.
Bornstein, 2000, Thrombospondin 2 Modulates Collagen Fibrillogenesis and Angiogenesis, Journal of Investigative Dermatology Symposium Proceedings 5(1):61-66.
Borowczyk, 2009, Identification of a region of the DNMT1 methyltransferase that regulates the maintenance of genomic imprints, PNAS 106(49):20806-11.
Bottini, 2001, Autism: evidence of association with adenosine deaminase genetic polymorphism, Neurogenetics 3:111-13.
Bottini, 2002, Cooperative effect of adenosine deaminase and ABO-secretor genetic complex on susceptibility to childhood asthma, European Respiratory Journal 20:1613-15.
Braslaysky, 2003, Sequence information can be obtained from single DNA molecules, Proceedings of the National Academy of Sciences, (USA) 100:3960-4.

(56) References Cited

OTHER PUBLICATIONS

Brenner, 2000, Gene expression analysis by massively parallel signature sequencing (MPSS) on microbead arrays, Nature Biotechnology 18:630-34.
Brenner, 2002, Conserved regulation of the lymphocyte-specific expression of lck in the Fugu and mammals, PNAS 99:2936-41.
Bultman, 2000, "A Brg1 null mutation in the mouse reveals functional differences among mammalian SWI/SNF complexes," Mol Cell 6(6):1287-95.
Bultman, 2006, "Maternal BRG1 regulates zygotic genome activation in the mouse," Genes Dev 20(13):1744-54.
Burney, 2007, Gene Expression Analysis of Endometrium Reveals Progesterone Resistance and Candidate Susceptibility Genes in Women with Endometriosis, Endocrinology 148(8):3814-26.
Burns, 2003, Roles of NPM2 in chromatin and nucleolar organization in oocytes and embryos, Science 300:633-36.
Carabatsos, 1998, "Characterization of oocyte and follicle development in growth differentiation factor-9-deficient mice," Dev Biol 204(2):373-84.
Carlson, 1992, Properties and localization of DNA methyltransferase in preimplantation mouse embryos: implications for genomic imprinting, Genes Dev. 6:2536-41.
Cenarro, 2003, A common variant in the ABCA1 gene is associated with a lower risk for premature coronary heart disease in familial hypercholesterolaemia, Journal of Medical Genetics 40:163-68.
Chang, 2011, MUC4 gene polymorphisms associate with endometriosis development and endometriosis related infertility, BMC Med 9:19.
Chirgwin, 1979, Isolation of biologically active ribonucleic acid from sources enriched in ribonuclease, Biochemistry, 18:5294-99.
Chiu, 2008, Effects of Native Human Zona Pellucida Glycoproteins 3 and 4 on Acrosome Reaction and Zona Pellucida Binding of Human Spermatozoa, Biol Reprod 79(5):869-77.
Chong, 1993, "Preimplantation prevention of X-linked disease:reliable and rapid sex determination of single human cells by restriction analysis of simultaneously amplified ZFX and ZFY sequences," Hum Mol Genet 2(8):1187-91.
Christians, 1997, "Evidence for the involvement of mouse heat shock factor 1 in the atypical expression of the HSP70.1 heat shock gene during mouse zygotic genome activation," Mol Cell Biol 17(2):778-88.
Christians, 2000, "Maternal effect of Hsf1 on reproductive success," Nature 407(6805):693-4.
Christiansen-Weber, 2000, Functional Loss of ABCA1 in Mice Causes Severe Placental Malformation, Aberrant Lipid Distribution, and Kidney Glomerulonephritis As Well As High-Density Lipoprotein Cholesterol Deficiency, The American Journal of Pathology 157:1017.
Ciccone, 2009, "KDM1B is a histone H3K4 demethylase required to establish maternal genomic imprints," Nature 461(7262):415-8.
Cirio, 2008, "DNA methyltransferase 1o functions during preimplantation development to preclude a profound level of epigenetic variation," Dev Biol 324(1):139-50.
Collins, 2006, The Application of genomic and proteomic technoloies in predictive, preventive and personalized medicine, Vascular Pharmacology, Vascular Pharmacology 45(5):258-67.
Davidson, 2003, "Cdx4 mutants fail to specify blood progenitors and can be rescued by multiple hox genes," Nature 425(6955):300-6.
Davis, 1993, "A null c-myc mutation causes lethality before 10.5 days of gestation in homozygotes and reduced fertility in heterozygous female mice," Genes Dev 7(4):671-82.
De Andres, 1995, Improved Method for mRNA Extraction from Paraffin a Embedded Tissues, BioTechniques 18:42-44.
De Klein, 2000, "Targeted disruption of the cell-cycle checkpoint gene ATR leads to early embryonic lethality in mice," Curr Biol 10(8):479-82.
Dean, 1992, "Biology of mammalian fertilization:role of the zona pellucida," J Clin Invest 89(4):1055-9.
DeRisi, 1996, Use of a cDNA microarray to analyse gene expression patterns in human cancer, Nature Genetics 14:457-60.
Ding & Cantor, 2003, A high-throughput gene expression analysis technique using competitive PCR and matrix-assisted laser desorption ionization time-of-flight MS, PNAS 100(6):3059-64.
Dion, 2008, Dnmtl deficiency promotes CAG repeat expansion in the mouse germline, Human Molecular Genetics 17:1306-17.
Iglesias, 2008, "Expression pattern of glypican-3 (GPC3) during human embryonic and fetal development," Histol Histopathol 23(11):1333-40.
Ikeda, 2010, Expression of methylation pathway enzymes in bovine oocytes and preimplantation embryos, J of Exper Zoology Part A: Ecol Genet & Physiol 313A(3):129-36.
Irizarry, 2003, Exploration, normalization, and summaries of high density oligonucleotide array probe level data, Biostatistics 4(2):249-64.
Iuchi, 1999, Basonuclin, a zinc finger protein of keratinocytes and reproductive germ cells, binds to the rRNA gene promoter, Proc. Natl. Acad. Sci. U.S.A. 96:9628-32.
Jeddi-Tehrani, 2011, Analysis of Plasminogen Activator Inhibitor-1, Integrin Beta3, Beta Fibrinogen, and Methylenetetrahydrofolate Reductase Polymorphisms in Iranian Women with Recurrent Pregnancy Loss, Am J of Reprod Immunol 66(2)149-56.
Kanai, 1994, Rapid and simple method for preparation of genomic DNA from easily obtainable clotted blood, J Clin Pathol 47:1043-44.
Kang, 2009, "Single-nucleotide polymorphisms in the p53 pathway regulate fertility in humans," Proc Natl Acad Sci U S A 106(24):9761-6.
Kanka, 2003, Gene expression and chromatin structure in the pre-implantation embryo, Theriogenology 59:3-19.
Kao, 2003, "Expression profiling of endometrium from women with endometriosis reveals candidate genes for disease-based implantation failure and infertility," Endocrinology 144(7):2870-81.
Karolchik, 2008, "Comparative genomic analysis using the UCSC genome browser," Comparative Genomics (Humana Press), 17-33.
Kawai, 2012, Negative regulation of Odd-skipped related 2 by TGF-beta achieves the induction of cellular migration and the arrest of cell cycle, Biochem & Biophys Research Communications 421(4):696-700.
Kawamoto, 1999, "Expression profiling by iAFLP: a PCR-based method for genome-wide gene expression profiling," Genome Res 12:1305-12.
Kay, 1993, "Expression of Xist during mouse development suggests a role in the initiation of X chromosome inactivation," Cell 72(2):171-82.
Kim, 2008, SEBOX Is Essential for Early Embryogenesis at the Two-Cell Stage in the Mouse, Biol Reprod 79(6):1192-1201.
Komiyana, 2007, Local activation of TGF-beta1 at endometriosis sites, J Reprod Med 52(4):306-12.
Kononen, 1998, "Tissue microarrays for high-throughput molecular profiling of tumor specimens," Nat Med 4(7):844-47.
Kosaki, 2004, "Premature ovarian failure in a female with proximal symphalangism and Noggin mutation," Fertil Steril 81(4)1137-9.
Latham 1992, Acquisition of a transcriptionally permissive state during the 1-cell stage of mouse embryogenesis, Dev Biol 149:457-62.
Lee, 2004, "Effects of bone morphogenetic protein-7 (BMP-7) on primordial follicular growth in the mouse ovary," Mol Reprod Dev 69(2):159-63.
Lefievre, 2004, "Four zona pellucida glycoproteins are expressed in the human," Hum Reprod 19(7):1580-6.
LeGouy, 1998, "Differential preimplantation regulation of two mouse homologues of the yeast SWI2 protein," Dev Dyn 212(1):38-48.
Leland, 2009, "Heterozygosity for a Bub1 mutation causes female-specific germ cell aneuploidy in mice," Proc Natl Acad Sci U S A 106(31):12776-81.
Li, 2008, "A subcortical maternal complex essential for preimplantation mouse embryogenesis," Dev Cell 15(3):416-25.
Liang & Pardee, 1992, Differential display of eukaryotic messenger RNA by means of the polymerase chain reaction, Science 257:967-71.
Lockhart, 1996, Expression monitoring by hybridization to high-density oligonucleotide arrays, Nature Biotechnology 14(13):1675.

(56) References Cited

OTHER PUBLICATIONS

Loffler, 2003, "Etiology of ovarian failure in blepharophimosis ptosis epicanthus inversus syndrome:FOXL2 is a conserved, early-acting gene in vertebrate ovarian development," Endocrinology 144(7):3237-43.
Loughery, 2011, DNMT1 deficiency triggers mismatch repair defects in human cells through depletion of repair protein levels in a process involving the DNA damage response, Human Molecular Genetics 20:3241-55.
Lyall, 2010, "Association between ovulation inducing drug use, infertility, and autism spectrum disorders in the nurses' health study II," Meeting for Autism Research: International Society for Autism Research [Retrieved Dec. 23, 2012] from https://imfar.confex.com/imfar/2010/webprogram/Paper5541.html. Abstract.
Lyall, 2011, Maternal Ealry Life Factors Associated with Hormone Levels and the Risk of Having a Child with an Autism Spectrum Disorder in the Nurses Health Study II, J Autism Dev Disord 41:618-27.
Ma, 2006, "Basonuclin:a novel mammalian maternal-effect gene," Development 133(10):2053-62.
Ma, 2008, Histone deacetylase 1 (HDAC1) regulates histone acetylation, development, and gene expression in preimplantation mouse embryos, Dev Biol 319:110-20.
Maldonado-Perez, 2007, "Potential roles of the prokineticins in reproduction," Trends Endocrinol Metab 18(2).
Malizia, 2009, "Cumulative live-birth rates after in vitro fertilization," New England J Med 360:236-43.
Mannikko, 2005, Association between Sequence variations in genes encoding human zona pellucida glycoproteins and fertilization failure in IVF, Human Reproduction, 20(6):1578-1585.
Marguilies, 2005, "Genome sequencing in microfabricated high-density picolitre reactors," Nature 437:376-80.
Maskos & Southern, 1992, Oligonucleotide hybridisations on glass supports: a novel linker for oligonucleotide synthesis and hybridisation properties of oligonucleotides synthesised in situ, Nuc Acids Res 20:1679-84.
Matzuk, 2002, Genetic dissection of mammalian fertility pathways, Nature Cell Bio 4 Suppl:s41-49.
Maxam, 1977, A new method for sequencing DNA, Proc. of National Academy of Science USA 74:560-4.
McBride, 1983, An Investigation of Several Oeoxynucleoside Phosphoramidites Useful for Synthesizing Deoxyoligonucleotides, Tetrahedron Lett 24:245-48.
McCarthy, 2003, Loss of Bard1, the Heterodimeric Partner of the Brca1 Tumor Suppressor, Results in Early Embryonic Lethality and Chromosomal Instability, Molecular Cellular Biology 23(14):5056-63.
McKenzie, 2004, "Human cumulus granulosa cell gene expression: a predictor of ferilization and embryo selection in women undergoing IVF," Human reproduction, 19(12):2869-2874.
Medina & Lebovic, 2009, Endometriosis-associated nerve fibers and pain, Acta Obstet Gynecol Scand 88:968-75.
Messina, 2011, Dysregulation of Semaphorin7A/$\beta$1-integrin signaling leads to defective GnRH-1 cell migration, abnormal gonadal development and altered fertility, Hum Mol Genetics 20(24):4759-74.
Miettinen, 2001, Abnormal lipoprotein metabolism and reversible female infertility in HDL receptor (SR-BI)—deficient mice, J Clin Invest 108:1717-22.
Moore, 2005, "Molecular biology and physiological role of the oocyte factor, BMP-15," Mol Cell Endocrinol 234(1-2):67-73.
Mottershead, 2008, "Characterization of recombinant human growth differentiation factor-9 signaling in ovarian granulosa cells," Mol Cell Endocrinol 283(1-2):58-67.
Moudrianakis & Beer, 1965, Base sequence determination in nucleic acids with the electron microscope, PNAS 53:564-71.
Mouillet, 2008, "DEAD-box protein-103 (DP103, Ddx20) is essential for early embryonic development and modulates ovarian morphology and function," Endocrinology 149(5):2168-75.
Murray, 1999, Microdeletions in FMR2 may be a significant cause of premature ovarian failure, Journal of Medical Genetics 36:767-70.
Nicotra, 1998, Adenosine deaminase and human reproduction: a comparative study of fertile women and women with recurrent spontaneous abortion, Am. J. Reprod. Immunol. 39:266-70.

\* cited by examiner

 Mechanisms of endometriosis development complicate its treatment
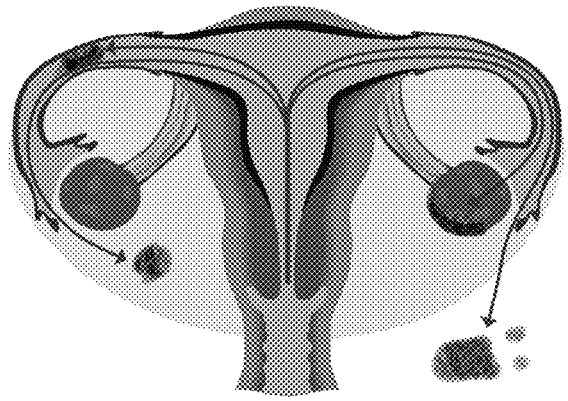
Retrograde Menstruation
FIG. 3
 Mechanisms of endometriosis development complicate its treatment
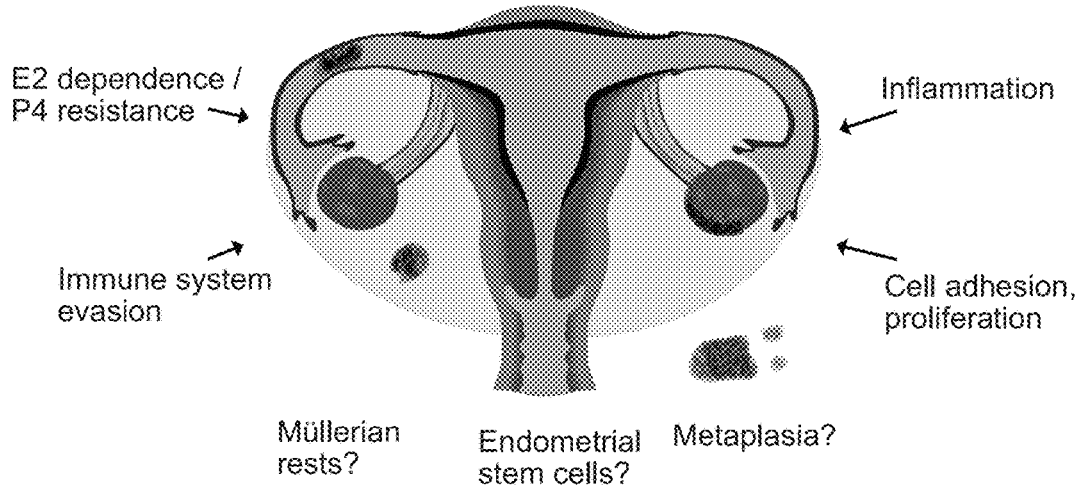
E2 dependence / P4 resistance
Immune system evasion
Inflammation
Cell adhesion, proliferation
Müllerian rests?  Endometrial stem cells?  Metaplasia?
FIG. 4

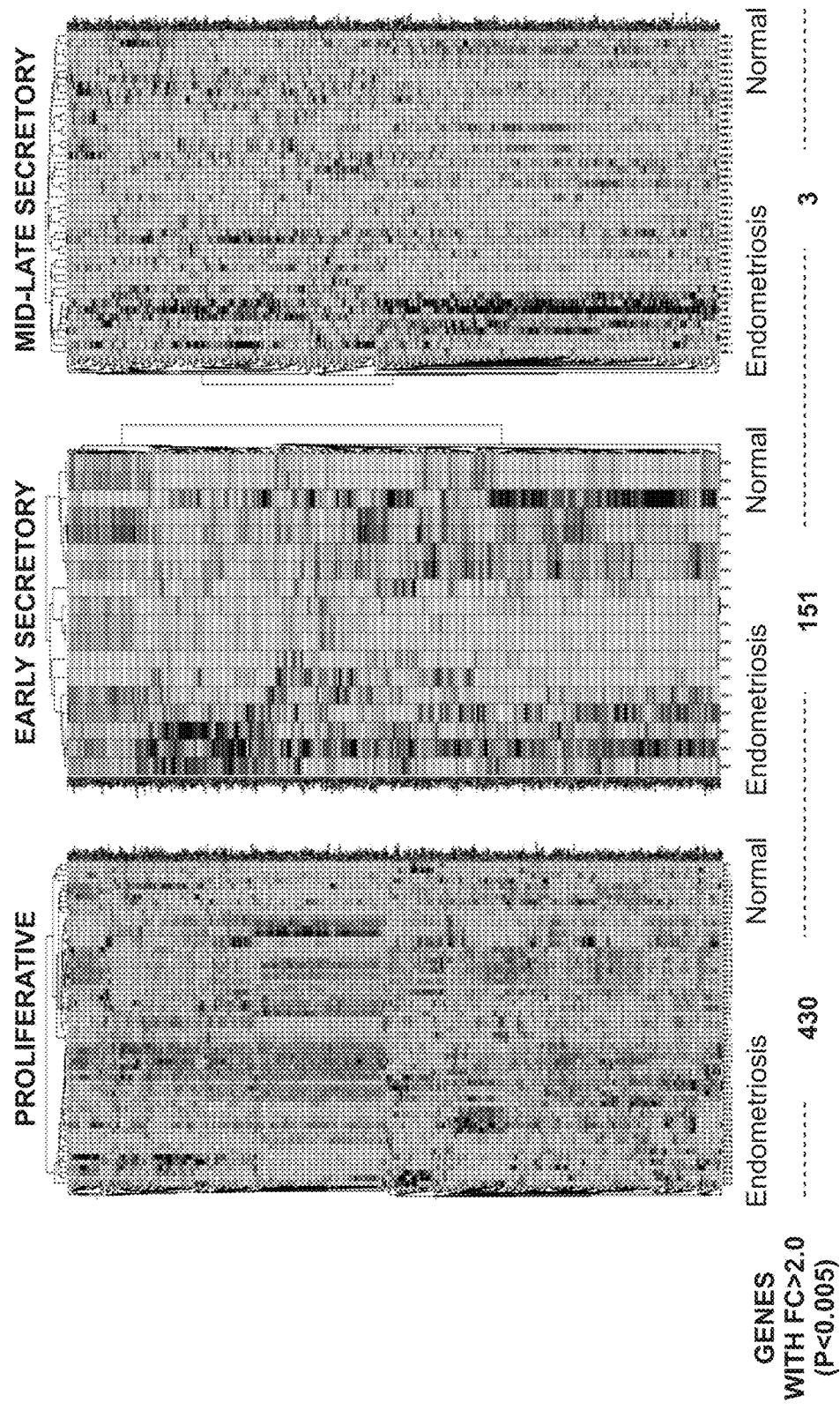

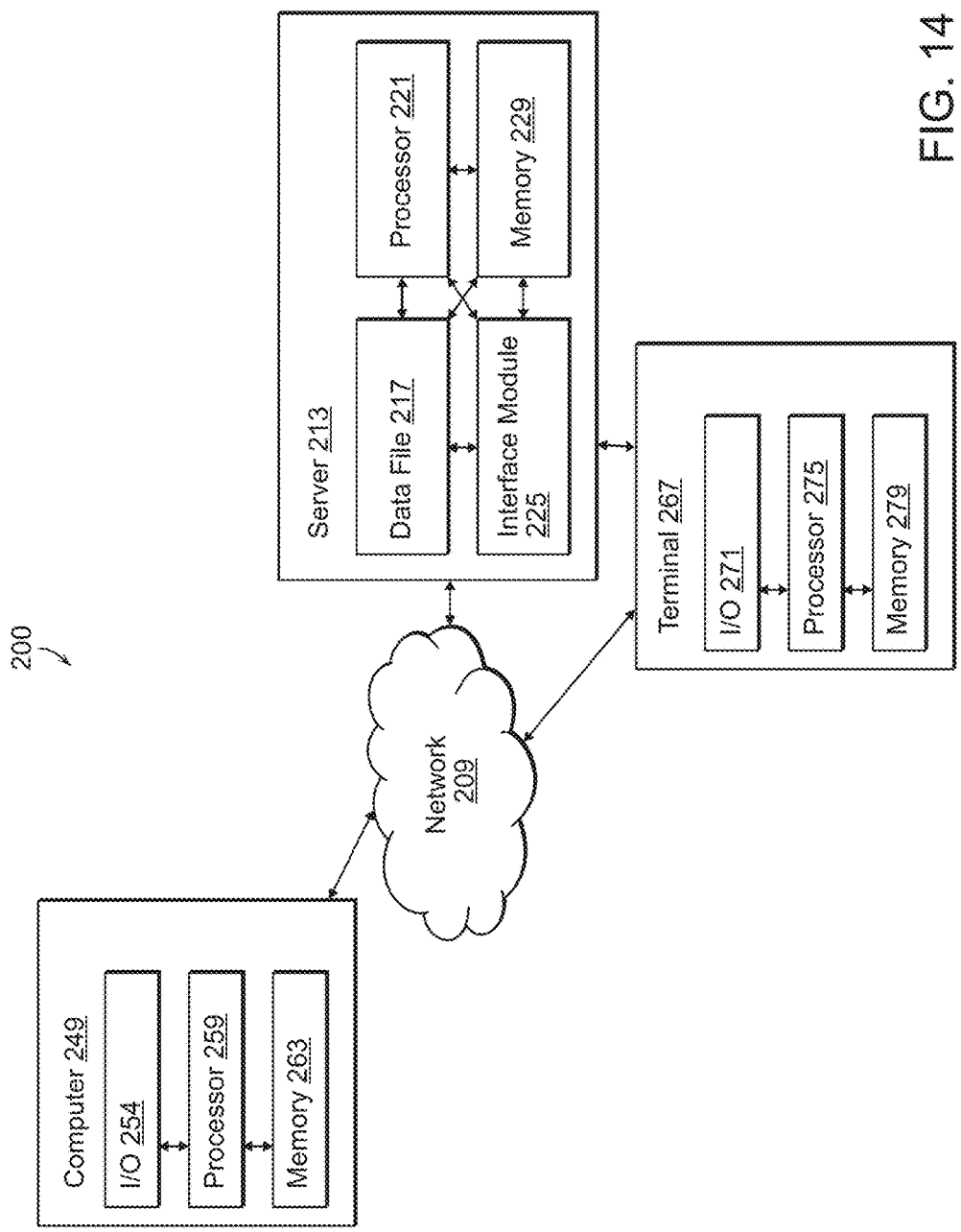

METHODS AND SYSTEMS FOR ASSESSING INFERTILITY AND RELATED PATHOLOGIES

CROSS-REFERENCE TO RELATED APPLICATIONS

This application claims priority to, and the benefit of, U.S. Provisional Application No. 62/025,802, filed Jul. 17, 2014, and U.S. Provisional Application No. 62/065,416, filed Oct. 17, 2014, each of which is incorporated by reference in its entirety.

BACKGROUND

According to the Centers for Disease Control and Prevention, 6.7 million women (around 10.9%) in the United States between the ages of 15 and 44 suffer from impaired fecundity, or the ability to become pregnant and carry a baby to term. See Chandra A, Copen C E, Stephen E H. Infertility and impaired fecundity in the United States, 1982-2010: Data from the National Survey of Family Growth. National health statistics reports; no 67. Hyattsville, Md.: National Center for Health Statistics, 2013. A variety of factors such as endometriosis, high rates of aneuploid embryos, and polycystic ovary syndrome (PCOS) can contribute to impaired fecundity and understanding these causes on a case-by-case basis can help inform treatment decisions.

Endometriosis affects 10% to 15% of reproductive-age women. Symptoms of endometriosis may include infertility, chronic pelvic pain, irregular uterine bleeding, dysmenorrhea, and/or dyspareunia. Endometriosis is characterized by the abnormal growth of endometrial tissue, which normally lines the inside of one's uterus, on the outside of one's uterus. The displaced endometrial tissue may spread to one's ovaries, bowels, or pelvic tissue, and, in some cases, continues to act like normal intrauterine endometrial tissue during one's uterine cycle—by thickening, breaking down, and bleeding. The uterine cycle is regulated by hormones and has three major phases: the menstrual phase, the proliferative phase, and the secretory phase. The secretory phase is often further broken down into the early secretory stage, mid-secretory phase, and late secretory phase. Symptoms and severity vary by case along with the need for fertility treatment and the likelihood of success thereof.

The cause of endometriosis is unclear. The most widely-accepted explanation of endometriosis is retrograde menstruation. Retrograde menstruation occurs when menstrual blood containing endometrial cells flows back through the fallopian tubes and into the pelvic cavity, as opposed to flowing out the body. The endometrial cells present in the back flow are believed to stick to the pelvic walls and surfaces of the pelvic organs, where they continue to proliferate. Other proffered causes of endometriosis include embryonic cell growth, surgical scar implantation, endometrial cell transport, or an immune system disorder.

Expression studies for examining genes associated with endometriosis have provided further understanding of its etiology. For example, the expression studies have indicated that misregulation of a number of molecular pathways are associated with endometriosis. While expression studies offer insight as to what genes correlate with endometriosis, there has yet to be a consistent approach that allows one to characterize endometriosis or inform treatment of endometriosis based on expression levels and regulation patterns.

PCOS is a common endocrine system disorder with symptoms that may include irregular or no menstrual periods, heavy periods, excess body and facial hair, acne, pelvic pain, trouble getting pregnant, and patches of thick, darker, velvety skin. Impaired fecundity resulting from PCOS may be treated using a number of methods including diet adjustments, ovulation-inducing medications, surgical intervention, and assisted reproductive techniques such as in-vitro fertilization (IVF). For women with PCOS, like other disorders affecting fertility, success rates for these treatments vary on a case-by-case basis and are not generally predictable and understood.

Aneuploidy is the presence of an abnormal number of chromosomes in a cell. High aneuploidy rates are often associated with poor oocyte and embryo quality, both of which decrease with age and often lead to unviable embryos and, accordingly, impaired fecundity. While aneuploidy rates appears to increase with a woman's age, the association has not been well characterized and the ability to predict aneuploidy rates for a given individual would be useful in informing family planning and possible fertility treatment.

As noted, many cases of impaired fecundity are treatable, allowing a woman to become pregnant and carry a baby to term. Some methods, such as IVF, can be expensive and painful while not necessarily producing the desired outcome. Accordingly, providing an accurate picture of an individual patient's likelihood of success with a given treatment method and equipping the patient to maximize that likelihood is extremely important before undertaking a treatment regimen.

SUMMARY

The invention relates to methods and systems for assessing infertility and related pathologies, including endometriosis, PCOS, and high aneuploidy rates. The invention includes systems and methods for assessing endometriosis and informing course of treatment. Aspects of the invention include identifying genetic signatures of endometriosis that correlate to the various phases of a woman's uterine cycle. In certain embodiments, a woman's phase-specific endometriosis signatures are identified by comparing the patient's genomic expression data to reference phase-specific expression patterns associated with endometriosis. The phase-specific endometriosis signatures are utilized to provide accurate diagnostics (e.g. determine phase of a patient's uterine cycle or determine type/severity of the endometriosis), tailor treatment based on the phase-specific endometriosis signature, and/or tailor treatment to coincide with a phase of interest.

Systems and methods of the invention also relate to assessing risk of IVF failure in patients with PCOS. In general, methods include identifying obese patients suffering from PCOS through a measure such as body mass index (BMI) and predicting likelihood of implantation, clinical pregnancy, and/or live birth outcomes in IVF treatment. The invention includes systems and methods for assessing an individual's risk of producing an aneuploid embryo based on factors including age and follicle-stimulating hormone (FSH) levels.

According to certain aspects, phase-specific genetic signatures for a patient are determined by identifying the patient's gene expression levels that correspond to a regulation pattern associated with a specific phase of the uterine cycle. The regulation pattern may be indicative of an endometriotic condition or a non-endometriotic condition. The regulation pattern specific to the uterine cycle may be obtained from a consensus data set that incorporates data from one or more sources, including a certain patient population, publications, studies, and data repositories (including protein-protein interactions and tissue expression patterns). In particular embodiments, the regulation pattern includes statistically-significant expression patterns associated with endometriosis obtained from the consensus data set. In certain embodiments, a meta-analysis is performed on the consensus data set to determine the regulation pattern. The meta-analysis may process and filter data based on a number a variables, such ectopic and/or eutopic tissue, the phases of the uterine cycle, particular patient populations, e.g. infertile/not infertile, positive/negative diagnosis for endometriosis, location of the ectopic tissue, pain and other endometriosis-associated symptoms.

In some embodiments, the invention provides methods for assessing endometriosis that include conducting a laboratory procedure to determining levels of transcripts present in a sample obtained from a patient who is suspected of having endometriosis, and identifying transcript levels that correspond to a regulation pattern specific to a time-point in the patient's uterine cycle. In some embodiments, the time-point of the regulation pattern is a phase of the uterine cycle. The identified transcript levels of the patient are then used to characterize endometriosis. The characterization may include determining the phase(s) of the subject's uterine cycle based on the identified transcripts. Additionally, the characterization may include determining the type/stage of the endometriosis based on the identified transcripts. In further embodiments, the method may further include determining the type of treatment for the endometriosis (e.g. a drug or therapeutic that targets the gene or the biochemical pathways associated with the gene) or timing of the treatment based on the characterization (e.g., during a certain phase of the uterine cycle).

Other aspects involve methods for targeting treatment of endometriosis. In certain embodiments, such methods include determining expression levels of one or more genes over different time-points during a subject's uterine cycle, identifying a time point during the uterine cycle in which expression levels are not synchronous or are dissimilar with respect to a non-endometriotic condition. For example, the subject may have differentially expressed genes at a certain phase—in circumstances where a subject's genes are regulation pattern (i.e. up-regulated/de-regulated) during the proliferative phase is different from the non-endometriodic regulation patterns at the proliferative phase. A course of treatment may then be indicated to coincide with the phases where the misregulation is indicated. In addition, a course of treatment may be indicated that based on the misregulation, e.g. a drug or therapeutic that targets the gene or the biochemical pathways associated with the gene.

Further embodiments involve determining genetic signatures of a patient across the various phases of the patient's uterine cycle in order to classify endometriosis. Such methods include determining expression levels of one or more transcripts in a sample obtained from a subject with endometriosis across different time-points of the subject's uterine cycle. The determined transcript levels are then compared to reference transcript levels corresponding to different time-points of the uterine cycle. The reference transcript level may be the consensus expression level of one or more transcripts obtained from a population of certain subjects. The subjects that make up the population for the reference level may be chosen based on certain phenotypic traits—e.g., positive for endometriosis, negative for endometriosis, infertile, fertile, certain age or weight, etc. Based on the comparison, differential transcripts at each time point of the uterine cycle are determined. The differential transcripts at each time point are considered the subject's genetic signature for the respective time points. The subject's genetic signature can then be used to classify endometriosis, e.g., determine the type/stage of the endometriosis, and to determine a course of treatment specific to the subject's genetic signatures.

Certain aspects of the invention include an array for assessing endometriosis. The array includes a substrate and a plurality of oligonucleotides attached to the substrate at discrete addressable positions. At least one of the oligonucleotides hybridizes to a portion of one of the following genes: CCL3L1, CCL3, FAM180A, THBS2, PDGFRL, FN1, CLE11A, CCNA2, KIF20A, BUB1B, HSD17B6, HSD11B1, C7, C3, CXCL2, CXCL12, CXCL13, PDGFC, CXCL14, ACTA2, TAGLN, and SORBS1.

In certain aspects, systems and methods of the invention relate to determining that a patient has a decreased probability of successful IVF treatment where the patient is diagnosed with PCOS and the patient's BMI is greater than or equal to a threshold level. In certain embodiments the threshold level may be 30 kg/m$^2$.

In certain aspects, methods of the invention relate to assessing future aneuploidy rates. The methods includes conducting a laboratory procedure to determine a follicle stimulating hormone (FSH) level in a sample obtained from an individual and matching the FSH level with the individual's age. The method also includes the steps of identifying a prospective risk of producing an aneuploid embryo at a given age based upon said matching step.

In certain embodiments, the sample may include blood or urine obtained from the individual. The matching step may include comparing the FSH level to a threshold level. In various embodiments, where the FSH level is below the threshold level, prospective risk may be identified by taking an initial risk of producing an aneuploidy embryo and increasing that risk by about 10% for each year of the individual's age above puberty. In alternative methods, where the FSH level is above the threshold level, prospective risk may be identified by taking an initial risk of producing an aneuploidy embryo and increasing that risk by about 15% for each year of the individual's age above puberty. In certain embodiments, the threshold level may be about 13 mUI/mL. Methods may include preparing a written report recommending an accelerated course of treatment for the individual or preparing a written report recommending oocyte retrieval and cryopreservation. In certain embodiments, methods may include retrieving and cryopreserving an oocyte from the individual where the FSH level is greater than the threshold level.

BRIEF DESCRIPTION OF DRAWINGS

FIG. 3 illustrates retrograde menstruation.

FIG. 4 illustrates conditions associated with endometriosis.

FIG. 7 illustrates the phase-specific genetic signature differences between endometriosis and normal populations.

FIG. 14 illustrates a system for performing methods of the invention.

DETAILED DESCRIPTION

Figure 1:
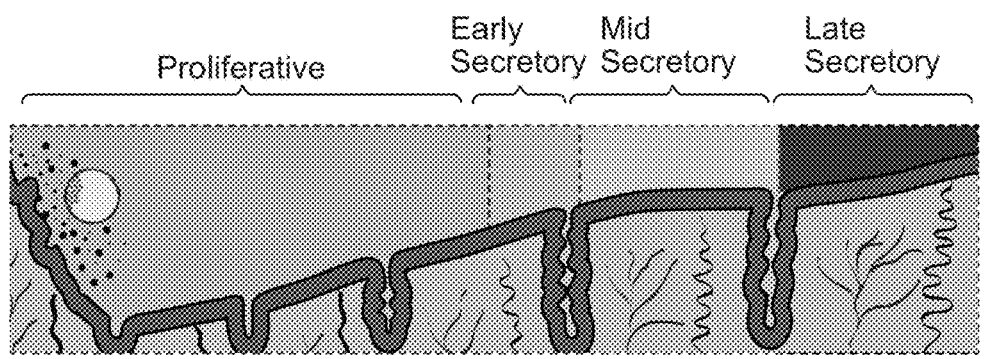
FIG. 1 illustrates the thickness changes of the endometrial lining as the uterine cycle progresses from the proliferative stage to the late secretory stage.

The invention generally relates to methods and systems for assessing endometriosis in a subject and informing course of treatment. Aspects of the invention include identifying genomic signatures for endometriosis that correlate to the various phases of a woman's uterine cycle. The phase-specific endometriosis signatures are utilized to provide accurate diagnostics (e.g. determine phase of a patient's uterine cycle or determine type/severity of the endometriosis), tailor treatment based on the phase-specific endometriosis signature, and/or tailor treatment to coincide with a particular phase.

Methods of the invention relate to characterizing and informing treatment of endometriosis. Endometriosis is the abnormal proliferation of endometrial tissue outside of the uterine. The endometrial tissue outside of the uterine is often referred to as ectopic tissue; whereas the normal endometrial tissue that lines the inside of the uterine is referred to as eutopic tissue. In some instances, the ectopic endometrial tissue behaves in a similar manner as the eutopic tissue, i.e. thickening and bleeding over the course of the uterine (or menstrual) cycle. The menstrual fluid generated from the ectopic tissue, unlike the eutopic tissue, has no direct route of discharge. As a result, cysts often form at sites of endometriotic adhesion and the surrounding area may become chronically inflamed, which elicits cellular responses relating to immunity and tissue remodeling.

There are several different types/stages of endometriosis. The stage of the endometriosis is based on the location, amount, depth, and size of the ectopic tissue. Specific criteria include the extent and spread of the tissue, the involvement of pelvic structures in the disease, the extent of pelvic adhesions, and the blockage of fallopian tubes. Stage I (subtle stage) involves minimal ectopic tissue, i.e. subtle cyst-like growths from 1 to 3 mm. Stage II (typical stage) includes mild ectopic tissue, including cysts and fibrous growths that may span 1 to 2 cm. Stage III (cystic ovarian stage) involves large cysts ranging from 4-15 cm that cover ovaries. Stage IV (severe stage) involves wide-spread solid tumors covering a majority of the pelvic structures.

The uterine cycle governing endometrial tissue (both eutopic and ectopic) has several different phases. The different phases are characterized by hormone changes, and thus the phases vary from person to person. The uterine cycle begins with the menstrual or menstruation phase. The menstrual phase is the phase during which the endometrium is shed as menstrual flow. For eutopic tissue, the menstrual flow sheds out of the cervix and vagina, whereas the menstrual flow may not be discharged for ectopic tissue. The first day of menstrual flow is defined as the first day of the menstrual cycle. The menstrual phase lasts about 3 to 7 days. During the menstrual phase, the pituitary glands begin to secrete follicle-stimulating hormone (FSH). The rise in FSH triggers the proliferation phase (Follicular).

The proliferation phase is the part of the uterine cycle during which follicles inside the ovaries develop and mature in preparation for ovulation. The levels of FSH increase in the bloodstream during the proliferation phase, stimulating the maturation of follicles. The follicles each contain an egg, and usually only one will reach full growth and will be released at ovulation. Also during the proliferation phase, the ovaries produce estrogen, which causes endometrium tissue to thicken. Once estrogen levels peak, the pituitary glands slow the secretion of FSH in favor of secreting luteinizing hormone (LH). Increased levels of LH cause the mature follicle to rupture and release the egg. The released egg will travel to the fallopian tubes. The releasing of the egg is called ovulation, and it usually occurs about 14 days from the beginning of the next uterine cycle.

The end of ovulation marks the beginning of the secretory (Luteal) phase. During the secretory phase, LH and FSH decrease. The ruptured follicle closes after releasing the egg and forms a corpus luteum, which produces progesterone. Estrogen levels are high during the secretory phase, and progesterone and estrogen cause the lining of the uterus to thicken more in order to prepare for possible fertilization. If the egg is not fertilized, the corpus luteum degenerates, progesterone production stops and estrogen levels decrease. Eventually, the top layers of the endometrial lining break down and shed, starting a new uterine cycle. The progression of the secretary phase may further broken down in to early secretory, mid secretory, and late secretory. FIG. 1 illustrates the changing of the thickness of the endometrial lining as the uterine cycle progresses from the proliferative stage to the late secretory stage.

Aspects of the invention determine and analyze gene expression patterns during different time-points over the uterine cycle. In certain embodiments, the different time-points are the various phases of the uterine cycle. For example, expression levels of one or more genes may be determined during the menstrual phase, proliferation phase, or the secretory phase (early, mid or late).

Methods of the invention involve obtaining a sample, e.g. a tissue or body fluid, which is suspected to include an endometrial-associated gene or gene product. The sample may be collected in any clinically acceptable manner. A tissue is a mass of connected cells and/or extracellular matrix material, e g skin tissue, endometrial tissue, nasal passage tissue, CNS tissue, neural tissue, eye tissue, liver tissue, kidney tissue, placental tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue. A sample also may be media containing cells or biological material. In certain embodiments, infertility-associated genes or gene products may be found in reproductive cells or tissues, such as gametic cells, gonadal tissue, fertilized embryos, and placenta. In certain embodiments, the sample is drawn maternal blood or saliva.

In particular embodiments, the sample is obtained from endometrial tissue. The endometrial tissue may be eutopic (e.g. normal intrauterine endometrial tissue), or ectopic, (e.g., misplaced endometrial tissue). The endometrial tissue samples may be obtained over different time-points across the uterine cycle.

Laboratory procedures described below (e.g., determining expression levels using a microarray or nucleic acid extraction, enrichment, amplification, or sequencing) are performed on the sample to determine expression levels for one or more transcripts. Nucleic acid is extracted from the sample according to methods known in the art. See for example, Maniatis, et al., Molecular Cloning: A Laboratory Manual, Cold Spring Harbor, N.Y., pp. 280-281, 1982, the contents of which are incorporated by reference herein in their entirety. In certain embodiments, a genomic sample is collected from a subject followed by enrichment for genetic regions or genetic fragments of interest, for example by hybridization to a nucleotide array comprising endometrial-related genes or gene fragments of interest. The sample may be enriched for genes of interest (e.g., endometrial-associated genes) using methods known in the art, such as hybrid capture. See for examples, Lapidus (U.S. Pat. No. 7,666,593), the content of which is incorporated by reference herein in its entirety.

RNA may be isolated from eukaryotic cells by procedures that involve lysis of the cells and denaturation of the proteins contained therein. Tissue of interest includes gametic cells, gonadal tissue, endometrial tissue, fertilized embryos, and placenta. RNA may be isolated from fluids of interest by procedures that involve denaturation of the proteins contained therein. Fluids of interest include blood, menstrual fluid, mammary fluid, follicular fluid of the ovary, peritoneal fluid, or culture medium. Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., Biochemistry 18:5294-5299 (1979)). Poly(A)+RNA is selected by selection with oligo-dT cellulose (see Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol. If desired, RNase inhibitors may be added to the lysis buffer. Likewise, for certain cell types, it may be desirable to add a protein denaturation/digestion step to the protocol.

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or SEPHADEX (see Ausubel et al., CURRENT PROTOCOLS IN MOLECULAR BIOL- OGY, vol. 2, Current Protocols Publishing, New York (1994). Once bound, poly(A)+mRNA is eluted from the affinity column using 2 mM EDTA/0.1% SDS.

According to certain embodiments, expression levels of a patient are compared to a reference data specific to phase in the uterine cycle. The reference data may comprise phase-specific endometriosis signatures (ectopic signatures) or phase-specific normal signatures (eutopics). The signatures may be determined by conducting a meta-analysis on one or more sources of expression data obtained from normal patients, endometriosis patients, or both. A meta-analysis suitable for use in accordance with the invention is described hereinafter. The phase-specific signatures are typically regulation pattern exhibited by either the healthy or the diseased tissue. Regulation patterns associated with endometriosis typically include up-regulated or de-regulated genes and the misregulation changes across the various phases of the uterine cycle. Up-regulation is a process that occurs within a cell triggered by a signal (originating internal or external to the cell), which results in increased expression of one or more genes and as a result the protein(s) encoded by those genes. Conversely, de-regulation is a process resulting in decreased gene and corresponding protein expression. In certain embodiments, the reference data may include a consensus expression levels associated with a particular patient population (e.g. endometriosis population or normal population).

Figure 8:
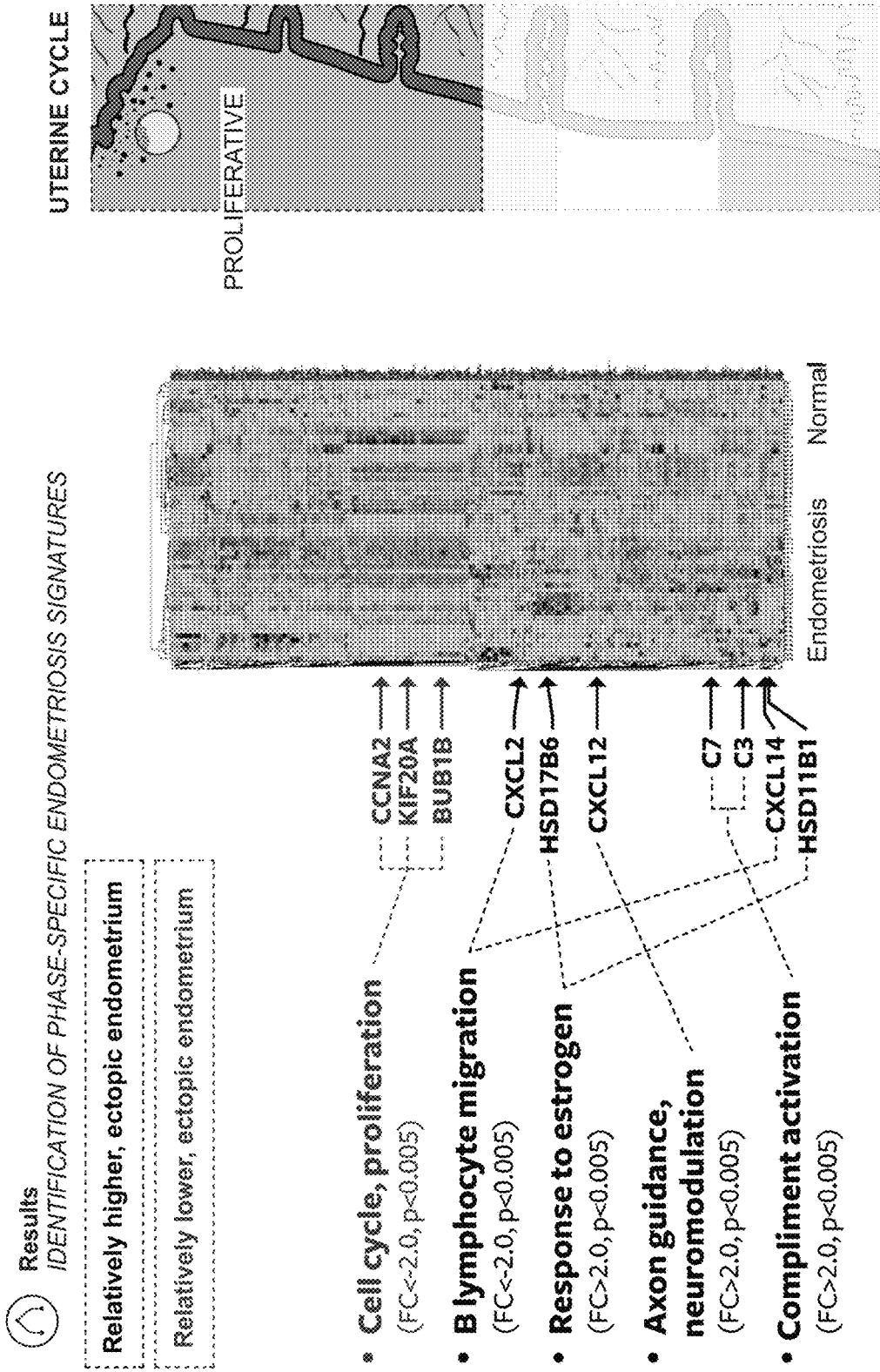
FIG. 8 illustrates up-regulated and de-regulated genes associated with endometriosis at the proliferative stage.
Figure 9:
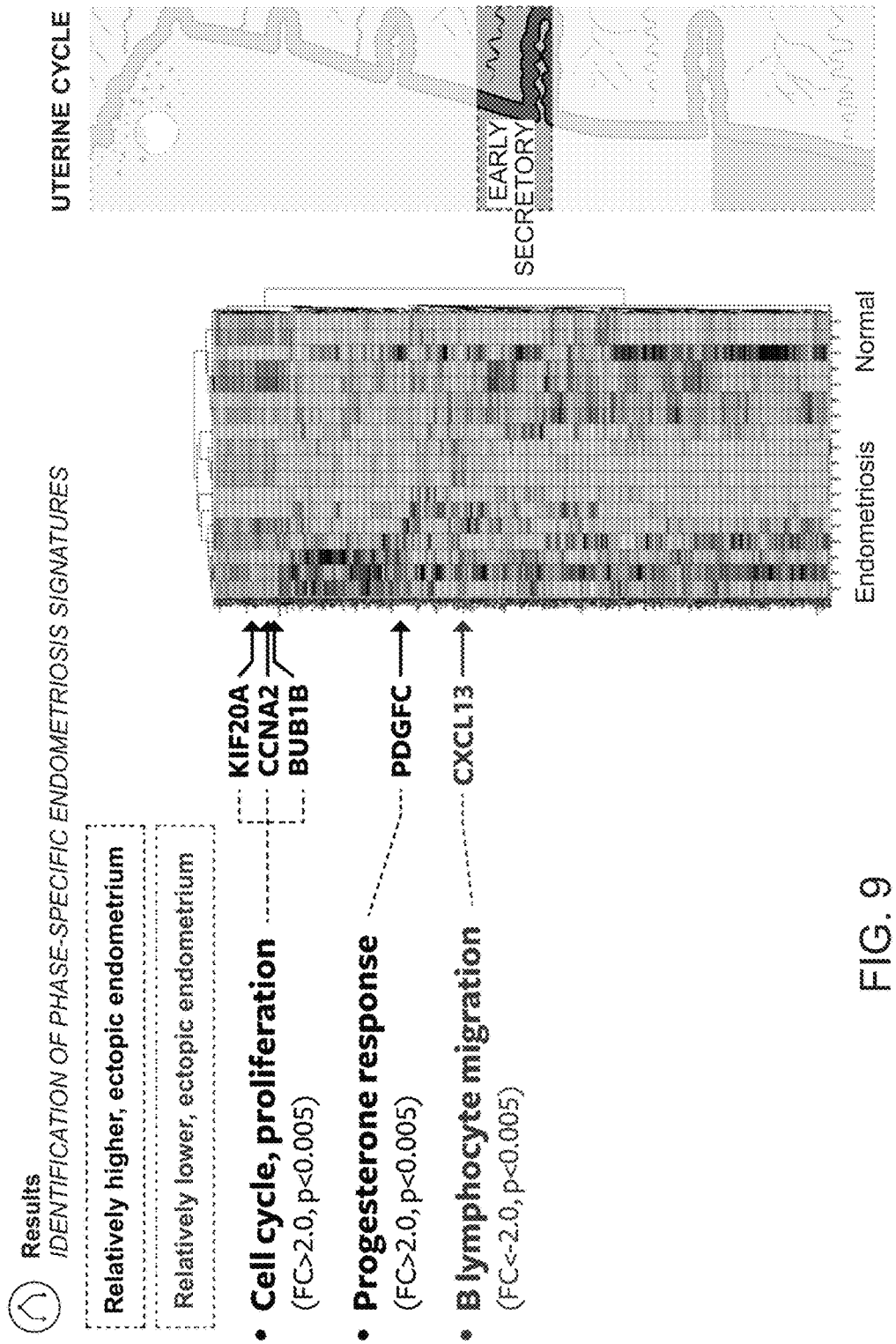
FIG. 9 illustrates up-regulated and de-regulated genes associated with endometriosis at the early secretory stage.
Figure 10:
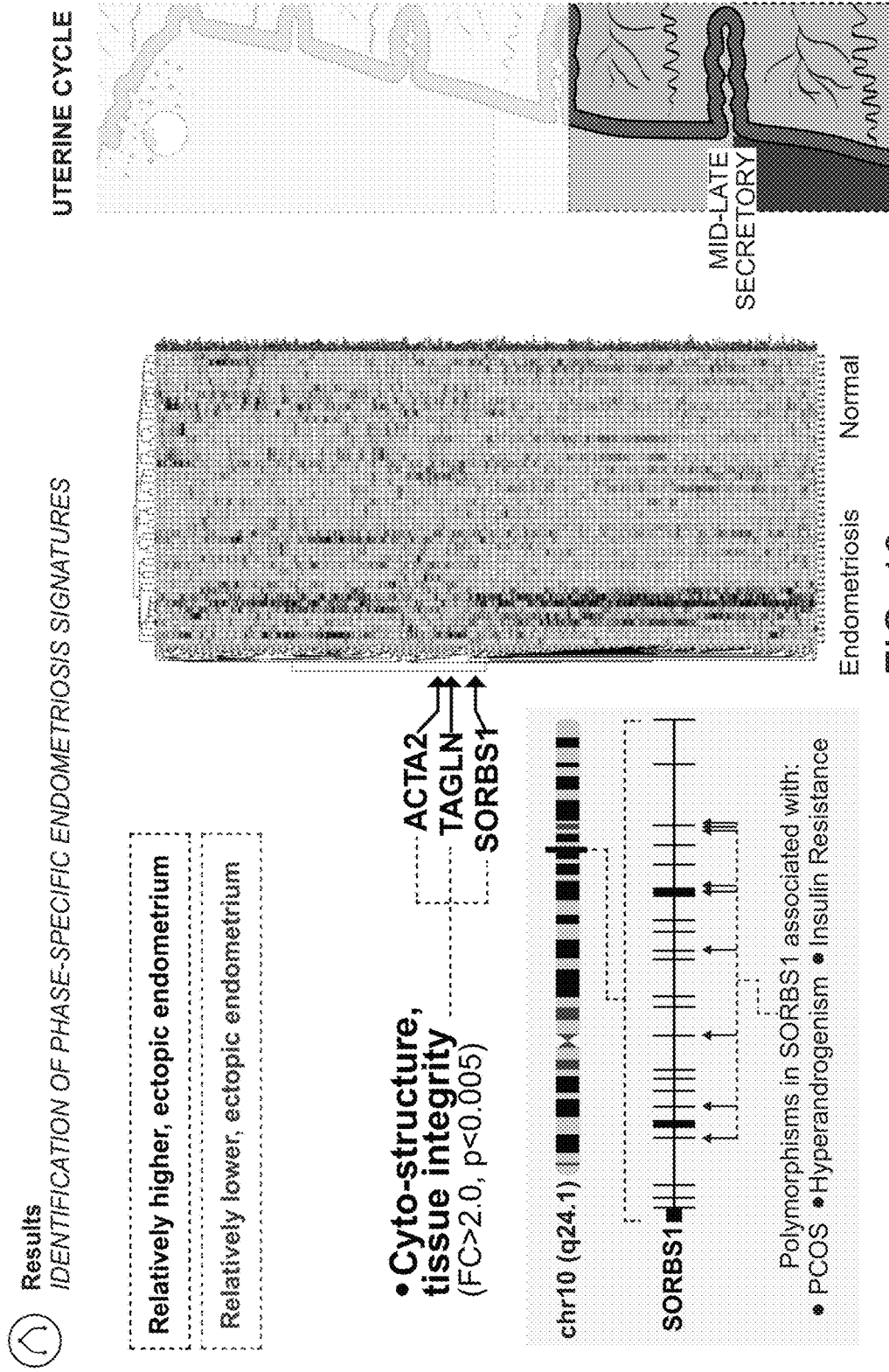
FIG. 10 illustrates up-regulated genes associated with endometriosis at the mid- to late secretory phase.

The following is a list of genes whose expression levels correlate significantly with endometriosis: CCL3L1, CCL3, FAM180A, THBS2, PDGFRL, FN1, CLE11A, CCNA2, KIF20A, BUB1B, HSD17B6, HSD11B1, C7, C3, CXCL2, CXCL12, CXCL13, PDGFC, CXCL14, ACTA2, TAGLN, and SORBS1. As shown in FIG. 8, de-regulated genes associated with the proliferative phase include CCNA2, KIF20A, BUB1B. Up-regulated genes associated with the proliferative phase include HSD17B6, HSD11B1, C7, C3, CXCL2, CXCL12, CXCL14. As indicated in FIG. 9, de-regulated genes associated with the early secretory phase include CXCL13. Up-regulated genes associated with the early secretory phase include CCNA2, KIF20A, BUB1B. As shown in FIG. 10, up-regulated genes associated with the mid- to late include ACTA2, TAGLN, and SORBS1.

Phase-specific genes associated with endometriosis are also described in: Hawkins, Shannon M., et al. "Functional microRNA involved in endometriosis." Molecular endocrinology 25.5 (2011): 821-832; Sha, G., et al. "Differentially expressed genes in human endometrial endothelial cells derived from eutopic endometrium of patients with endometriosis compared with those from patients without endometriosis." Human reproduction 22.12 (2007): 3159-3169; Burney, Richard O., et al. "Gene expression analysis of endometrium reveals progesterone resistance and candidate susceptibility genes in women with endometriosis." Endocrinology 148.8 (2007): 3814-3826; Crispi, Stefania, et al. "Transcriptional profiling of endometriosis tissues identifies genes related to organogenesis defects." Journal of cellular physiology 228.9 (2013): 1927-1934; Eyster, Kathleen M., et al. "Whole genome deoxyribonucleic acid microarray analysis of gene expression in ectopic versus eutopic endometrium." Fertility and sterility 88.6 (2007): 1505-1533; Hever, Aniko, et al. "Human endometriosis is associated with plasma cells and overexpression of B lymphocyte stimulator." Proceedings of the National Academy of Sciences 104.30 (2007): 12451-12456; Hull, M. Louise, et al. "Endometrial-peritoneal interactions during endometriotic lesion establishment." The American journal of pathology 173.3 (2008): 700-715; Talbi, S., et al. "Molecular phenotyping of human endometrium distinguishes menstrual cycle phases and underlying biological processes in normo-ovulatory women." Endocrinology 147.3 (2006): 1097-1121.

According to certain aspects, methods of the invention provide for obtaining phase-specific genetic reference data (i.e. signature or regulation pattern) based on data obtained from a number of endometriosis related sources. The data sources may include public and private endometriosis related databases. The reference endometriosis data set may include data obtained from a multitude of patients of similar or diverse background, a variety of sample types, and samples taken over different time points. In certain embodiments, parameters associated with the data set include age, negative/positive diagnosis of endometriosis, stage/type of the disease, pain associated with endometriosis, gravidity/parity, endometrioma position, tissue sampling method, phase of the uterine cycle, and ethnicity.

Figure 2:
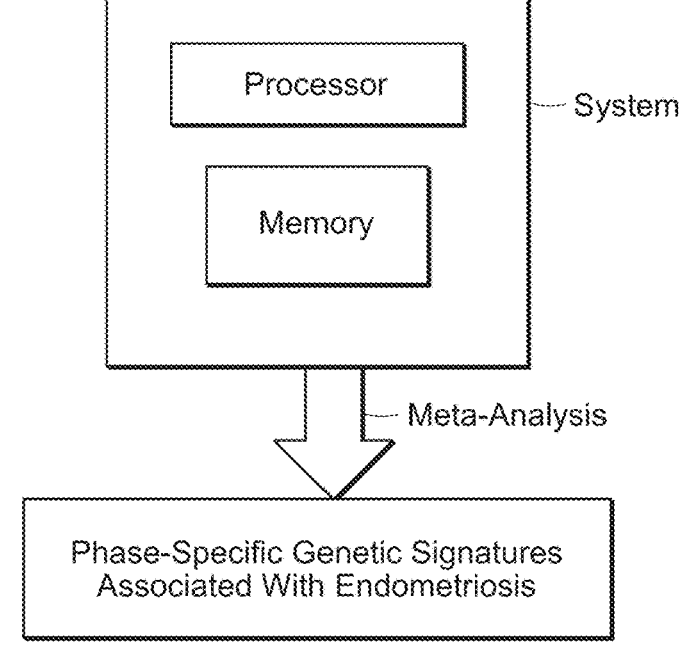
FIG. 2 provides a schematic illustration of the meta-analysis process.

FIG. 2 provides a schematic illustration of the meta-analysis process. As shown in FIG. 2, microarray data is obtained from several studies that examine gene expression differences between the tissue of patients with endometriosis and the tissue of normal patients (e.g. normal patients). The association between gene expression and endometriosis may be analyzed within each case or by comparing cases and controls using analysis of variance. According to certain embodiments, the micro-array data between studies may differ due to patient variability, tissue type, uterine phase during sample, experimental technique, etc. The micro-array data is entered into the system, processed to normalize the expression data and then subjected to a statistical analysis to identify endometriosis-related expression patterns of statistical significance. Statistical parameters may be chosen to identify gene expression patterns that are statistically significant. Based on the data, the system can also identify statistically significant expression patterns associated with specific phases of the uterine cycle.

Method of logistic regression are described, for example in, Ruczinski (Journal of Computational and Graphical Statistics 12:475-512, 2003); Agresti (An Introduction to Categorical Data Analysis, John Wiley & Sons, Inc., 1996, New York, Chapter 8); and Yeatman et al. (U.S. patent application number 2006/0195269), the content of each of which is hereby incorporated by reference in its entirety.

Other algorithms for analyzing associations are known. For example, the stochastic gradient boosting is used to generate multiple additive regression tree (MART) models to predict a range of outcome probabilities. Each tree is a recursive graph of decisions the possible consequences of which partition patient parameters; each node represents a question (e.g., is the FSH level greater than x?) and the branch taken from that node represents the decision made (e.g. yes or no). The choice of question corresponding to each node is automated. A MART model is the weighted sum of iteratively produced regression trees. At each iteration, a regression tree is fitted according to a criterion in which the samples more involved in the prediction error are given priority. This tree is added to the existing trees, the prediction error is recalculated, and the cycle continues, leading to a progressive refinement of the prediction. The strengths of this method include analysis of many variables without knowledge of their complex interactions beforehand.

A different approach called the generalized linear model, expresses the outcome as a weighted sum of functions of the predictor variables. The weights are calculated based on least squares or Bayesian methods to minimize the prediction error on the training set. A predictor's weight reveals the effect of changing that predictor, while holding the others constant, on the outcome. In cases where one or more predictors are highly correlated, in a phenomenon known as collinearity, the relative values of their weights are less meaningful; steps must be taken to remove that collinearity, such as by excluding the nearly redundant variables from the model. Thus, when properly interpreted, the weights express the relative importance of the predictors. Less general formulations of the generalized linear model include linear regression, multiple regression, and multifactor logistic regression models, and are highly used in the medical community as clinical predictors.

In order to determine expression levels associated with endometriosis that are statistically significant, a series of logistic regression models may be used. The p-values and odds ratio can be used for statistical inference. Logistic regression models are common statistical classification models. The endometriotic expression patterns across the different phases that are statistically significant are considered biomarkers or signatures for the disease.

According to aspects of the invention, the reference phase-specific endometriotic signatures can then be used to identify a patient's phase-specific endometriotic signatures, classify the patient's endometriosis and tailor treatment of the same.

In certain embodiments, the patient's genetic signatures are identified by comparing the patient's expression data across one or more time-points in the uterine cycle to reference phase-specific expression levels. The patient's phase specific genetic signature for endometriosis may include expression levels that are the same as or dissimilar from the reference phase-specific reference data. For example, the reference phase-specific pattern or expression data may represent expression levels of subjects having endometriosis. In such instance, similarities between the patient's expression levels and the reference may be indicative of the patient's phase-specific genetic signature. In another example, the reference phase-specific pattern or expression data may represent expression levels of subjects without endometriosis. In such instance, dissimilarities between the patient's expression levels and the reference may be indicative of the patient's phase-specific genetic signature.

By identifying the patient's phase-specific endometriosis signature, a treatment regimen can be prescribed or set forth in an informative report that is targeted to the patient's signature. For example, a drug or therapeutic that targets the gene or the biochemical pathways associated with the gene may be prescribed. In certain embodiments, the course of treatment is tailored to the patient's expression signatures in each phase. For example, treatment may only be indicated in one of the phases (such as the proliferative phase) or different treatments may be indicated for two or more of the phases. As such, methods of the inventions advantageous inform both timing and type of treatment.

In certain embodiments, the invention provides methods for assessing endometriosis that include determining levels of transcripts present a patient's sample, who is suspected of having endometriosis, identifying those transcript levels that correspond to a regulation pattern specific to a time-point in a uterine cycle and characterizing endometriosis based upon the identified transcript levels. In some embodiments, the time-point of the regulation pattern is a phase of the uterine cycle. The characterization may include determining the phase(s) of the subject's uterine cycle based on the identified transcripts. Additionally, the characterization may include determining the type/stage of the endometriosis based on the identified transcripts. In further embodiments, the method may further include determining the timing or type of treatment for the endometriosis based on the characterization.

Other embodiments involve methods for targeting treatment of endometriosis. For example, some embodiments for targeting the treatment of endometriosis include determining expression levels of one or more genes over different time-points during a subject's uterine cycle, identifying a time point during the uterine cycle in which expression levels are dyssynchronous or dissimilar with respect to a non-endometriotic condition, and informing a course of treatment specific to the subject that coincides with the identified time point. For example, the subject may have differentially expressed genes at a certain phase, in circumstances where a subject's genes are regulation pattern (i.e. upregulated/deregulated) during the proliferative phase is different from the non-endometriodic regulation patterns at the proliferative phase. Treatments may involve a variety of known methods such as hormone therapies (e.g., hormonal contraceptives, gonadotropin-releasing hormone (Gn-RH) agonists and antagonists, Medroxyprogesterone, and Danazol), surgery to remove endometrial tissue, or even hysterectomy.

Further embodiments involve determining phase-specific genetic signatures of a patient across the various phases of the patient's uterine cycle to classify endometriosis. Such methods include determining expression levels of one or more transcripts in a sample obtained from a subject with endometriosis across different time-points of the subject's uterine cycle. The determined transcript levels are then compared to reference transcript levels corresponding to different time-points of the uterine cycle. The reference transcript level may be the consensus expression level of one or more transcripts obtained from a patient population. The patient population chosen for the reference level may be chosen based on certain phenotypic traits—e.g., positive for endometriosis, negative for endometriosis, infertile, fertile, certain age or weight, etc. Based on the comparison, differential transcripts at each time point of the uterine cycle are determined. The differential transcripts at each time point are considered the subject's genetic signature for the respective time points. The subject's genetic signature can then be used to classify endometriosis, e.g., determine the type/stage of the endometriosis and, and to determine a course of treatment specific to the subject's genetic signatures.

In certain aspects, the invention involves assessing transcripts present in a biological sample. Such methods may involve preparing amplified cDNA from total RNA. cDNA is prepared and indiscriminately amplified without diluting the isolated RNA sample or distributing the mixture of genetic material in the isolated RNA into discrete reaction samples. Preferably, amplification is initiated at the 3' end as well as randomly throughout the whole transcriptome in the sample to allow for amplification of both mRNA and non-polyadenylated transcripts. The double-stranded cDNA amplification products are thus optimized for the generation of sequencing libraries for Next Generation Sequencing platforms. Suitable kits for amplifying cDNA in accordance with the methods of the invention include, for example, the Ovation® RNA-Seq System.

Methods of the invention also involve sequencing the amplified cDNA. While any known sequencing method can be used to sequence the amplified cDNA mixture, single molecule sequencing methods are preferred. Preferably, the amplified cDNA is sequenced by whole transcriptome shotgun sequencing (also referred to herein as ("RNA-Seq"). Whole transcriptome shotgun sequencing (RNA-Seq) can be accomplished using a variety of next-generation sequencing platforms such as the Illumina Genome Analyzer platform, ABI Solid Sequencing platform, or Life Science's 454 Sequencing platform.

Differential transcript levels within the biological sample can also be analyzed using via microarray techniques. The amplified cDNA can be used to probe a microarray containing gene transcripts associated with one or conditions or diseases, such as any prenatal condition, or any type of cancer, inflammatory, or autoimmune disease.

In certain aspects, the invention provides a microarray including a plurality of oligonucleotides attached to a substrate at discrete addressable positions, in which at least one of the oligonucleotides hybridizes to a portion of a gene selected from CCL3L1, CCL3, FAM180A, THBS2, PDGFRL, FN1, CLE11A, CCNA2, KIF20A, BUB1B, HSD17B6, HSD11B1, C7, C3, CXCL2, CXCL12, CXCL13, PDGFC, CXCL14, ACTA2, TAGLN, and SORBS1.

Methods of constructing microarrays are known in the art. See for example Yeatman et al. (U.S. patent application number 2006/0195269), the content of which is hereby incorporated by reference in its entirety.

Microarrays are prepared by selecting probes that include a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

The probe or probes used in the methods of the invention are preferably immobilized to a solid support which may be either porous or non-porous. For example, the probes of the invention may be polynucleotide sequences which are attached to a nitrocellulose or nylon membrane or filter covalently at either the 3' or the 5' end of the polynucleotide. Such hybridization probes are well known in the art (see, e.g., Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, the solid support or surface may be a glass or plastic surface. In a particularly preferred embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

In preferred embodiments, a microarray comprises a support or surface with an ordered array of binding (e.g., hybridization) sites or "probes" each representing one of the genes described herein, particularly one of CCL3L1, CCL3, FAM180A, THBS2, PDGFRL, FN1, CLE11A, CCNA2, KIF20A, BUB1B, HSD17B6, HSD11B1, C7, C3, CXCL2, CXCL12, CXCL13, PDGFC, CXCL14, ACTA2, TAGLN, and SORBS1. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). In preferred embodiments, each probe is covalently attached to the solid support at a single site.

Microarrays can be made in a number of ways, of which several are described below. However produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. The microarrays are preferably small, e.g., between 1 cm$^2$ and 25 cm$^2$, between 12 cm$^2$ and 13 cm$^2$, or 3 cm$^2$. However, larger arrays are also contemplated and may be preferable, e.g., for use in screening arrays. Preferably, a given binding site or unique set of binding sites in the microarray will specifically bind (e.g., hybridize) to the product of a single gene in a cell (e.g., to a specific mRNA, or to a specific cDNA derived therefrom). However, in general, other related or similar sequences will cross hybridize to a given binding site.

The microarrays of the present invention include one or more test probes, each of which has a polynucleotide sequence that is complementary to a subsequence of RNA or DNA to be detected. Preferably, the position of each probe on the solid surface is known. Indeed, the microarrays are preferably positionally addressable arrays. Specifically, each probe of the array is preferably located at a known, predetermined position on the solid support such that the identity (i.e., the sequence) of each probe can be determined from its position on the array (i.e., on the support or surface).

According to the invention, the microarray is an array (i.e., a matrix) in which each position represents one of the biomarkers described herein. For example, each position can contain a DNA or DNA analogue based on genomic DNA to which a particular RNA or cDNA transcribed from that genetic marker can specifically hybridize. The DNA or DNA analogue can be, e.g., a synthetic oligomer or a gene fragment. In one embodiment, probes representing each of the markers are present on the array. In certain embodiments, the array comprises probes for genes known to be associated with endometriosis. In addition, the array probes may be specific to genes known to be associated with endometriosis at a certain phase of the uterine cycle.

As noted above, the probe to which a particular polynucleotide molecule specifically hybridizes according to the invention contains a complementary genomic polynucleotide sequence. The probes of the microarray preferably consist of nucleotide sequences of no more than 1,000 nucleotides. In some embodiments, the probes of the array consist of nucleotide sequences of 10 to 1,000 nucleotides. In a preferred embodiment, the nucleotide sequences of the probes are in the range of 10-200 nucleotides in length and are genomic sequences of a species of organism, such that a plurality of different probes is present, with sequences complementary and thus capable of hybridizing to the genome of such a species of organism, sequentially tiled across all or a portion of such genome. In other specific embodiments, the probes are in the range of 10-30 nucleotides in length, in the range of 10-40 nucleotides in length, in the range of 20-50 nucleotides in length, in the range of 40-80 nucleotides in length, in the range of 50-150 nucleotides in length, in the range of 80-120 nucleotides in length, and most preferably are 60 nucleotides in length.

The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates.

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe on the microarray will be between 10 bases and 50,000 bases, usually between 300 bases and 1,000 bases in length. PCR methods are well known in the art, and are described, for example, in Innis et al., eds., PCR PROTOCOLS: A GUIDE TO METHODS AND APPLICATIONS, Academic Press Inc., San Diego, Calif. (1990). It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., Nucleic Acid Res. 14:5399-5407 (1986); McBride et al., Tetrahedron Lett. 24:246-248 (1983)). Synthetic sequences are typically between about 10 and about 500 bases in length, more typically between about 20 and about 100 bases, and most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., Nature 363:566-568 (1993); U.S. Pat. No. 5,539,083).

Probes are preferably selected using an algorithm that takes into account binding energies, base composition, sequence complexity, cross-hybridization binding energies, and secondary structure. See Friend et al., International Patent Publication WO 01/05935, published Jan. 25, 2001; Hughes et al., Nat. Biotech. 19:342-7 (2001).

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

The probes are attached to a solid support or surface, which may be made, e.g., from glass, plastic (e.g., polypropylene, nylon), polyacrylamide, nitrocellulose, gel, or other porous or nonporous material. A preferred method for attaching the nucleic acids to a surface is by printing on glass plates, as is described generally by Schena et al, Science 270:467-470 (1995). This method is especially useful for preparing microarrays of cDNA (See also, DeRisi et al, Nature Genetics 14:457-460 (1996); Shalon et al., Genome Res. 6:639-645 (1996); and Schena et al., Proc. Natl. Acad. Sci. U.S.A. 93:10539-11286 (1995)).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Science 251: 767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510, 270) or other methods for rapid synthesis and deposition of defined oligonucleotides (Blanchard et al., Biosensors & Bioelectronics 11:687-690). When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking (Maskos and Southern, 1992, Nuc. Acids. Res. 20:1679-1684), may also be used. In principle, and as noted supra, any type of array, for example, dot blots on a nylon hybridization membrane (see Sambrook et al., MOLECULAR CLONING—A LABORATORY MANUAL (2ND ED.), Vols. 1-3, Cold Spring Harbor Laboratory, Cold Spring Harbor, N.Y. (1989)) could be used. However, as will be recognized by those skilled in the art, very small arrays will frequently be preferred because hybridization volumes will be smaller.

In one embodiment, the arrays of the present invention are prepared by synthesizing polynucleotide probes on a support. In such an embodiment, polynucleotide probes are attached to the support covalently at either the 3' or the 5' end of the polynucleotide.

In a particularly preferred embodiment, microarrays of the invention are manufactured by means of an ink jet printing device for oligonucleotide synthesis, e.g., using the methods and systems described by Blanchard in U.S. Pat. No. 6,028,189; Blanchard et al., 1996, Biosensors and Bioelectronics 11:687-690; Blanchard, 1998, in Synthetic DNA Arrays in Genetic Engineering, Vol. 20, J. K. Setlow, Ed., Plenum Press, New York at pages 111-123. Specifically, the oligonucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells, which define the locations of the array elements (i.e., the different probes). Microarrays manufactured by this ink jet method are typically of high density, preferably having a density of at least about 2,500 different probes per 1 cm.sup.2. The polynucleotide probes are attached to the support covalently at either the 3' or the 5' end of the polynucleotide.

The polynucleotide molecules which may be analyzed by the present invention are DNA, RNA, or protein. The target polynucleotides are detectably labeled at one or more nucleotides. Any method known in the art may be used to detectably label the target polynucleotides. Preferably, this labeling incorporates the label uniformly along the length of the DNA or RNA, and more preferably, the labeling is carried out at a high degree of efficiency.

In a preferred embodiment, the detectable label is a luminescent label. For example, fluorescent labels, bioluminescent labels, chemiluminescent labels, and colorimetric labels may be used in the present invention. In a highly preferred embodiment, the label is a fluorescent label, such as a fluorescein, a phosphor, a rhodamine, or a polymethine dye derivative. Examples of commercially available fluorescent labels include, for example, fluorescent phosphoramidites such as FluorePrime (Amersham Pharmacia, Piscataway, N.J.), Fluoredite (Millipore, Bedford, Mass.), FAM (ABI, Foster City, Calif.), and Cy3 or Cy5 (Amersham Pharmacia, Piscataway, N.J.). In another embodiment, the detectable label is a radiolabeled nucleotide.

In a further preferred embodiment, target polynucleotide molecules from a patient sample are labeled differentially from target polynucleotide molecules of a reference sample. The reference can comprise target polynucleotide molecules from normal tissue samples.

Nucleic acid hybridization and wash conditions are chosen so that the target polynucleotide molecules specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook et al., MOLECULAR CLONING—A LABORATORY MANUAL (2ND ED.), Vols. 1-3, Cold Spring Harbor Laboratory, Cold Spring Harbor, N.Y. (1989), and in Ausubel et al., CURRENT PROTOCOLS IN MOLECULAR BIOLOGY, vol. 2, Current Protocols Publishing, New York (1994). Typical hybridization conditions for the cDNA microarrays of Schena et al. are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al., Proc. Natl. Acad. Sci. U.S.A. 93:10614 (1993)). Useful hybridization conditions are also provided in, e.g., Tijessen, 1993, HYBRIDIZATION WITH NUCLEIC ACID PROBES, Elsevier Science Publishers B.V.; and Kricka, 1992, NONISOTOPIC DNA PROBE TECHNIQUES, Academic Press, San Diego, Calif.

Particularly preferred hybridization conditions include hybridization at a temperature at or near the mean melting temperature of the probes (e.g., within 51° C., more preferably within 21° C.) in 1 M NaCl, 50 mM MES buffer (pH 6.5), 0.5% sodium sarcosine and 30% formamide.

When fluorescently labeled genes or gene products are used, the fluorescence emissions at each site of a microarray may be, preferably, detected by scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously (see Shalon et al., 1996, "A DNA microarray system for analyzing complex DNA samples using two-color fluorescent probe hybridization," Genome Research 6:639-645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., Genome Res. 6:639-645 (1996), and in other references cited herein. Alternatively, the fiber-optic bundle described by Ferguson et al., Nature Biotech. 14:1681-1684 (1996), may be used to monitor mRNA abundance levels at a large number of sites simultaneously.

Figure 11:
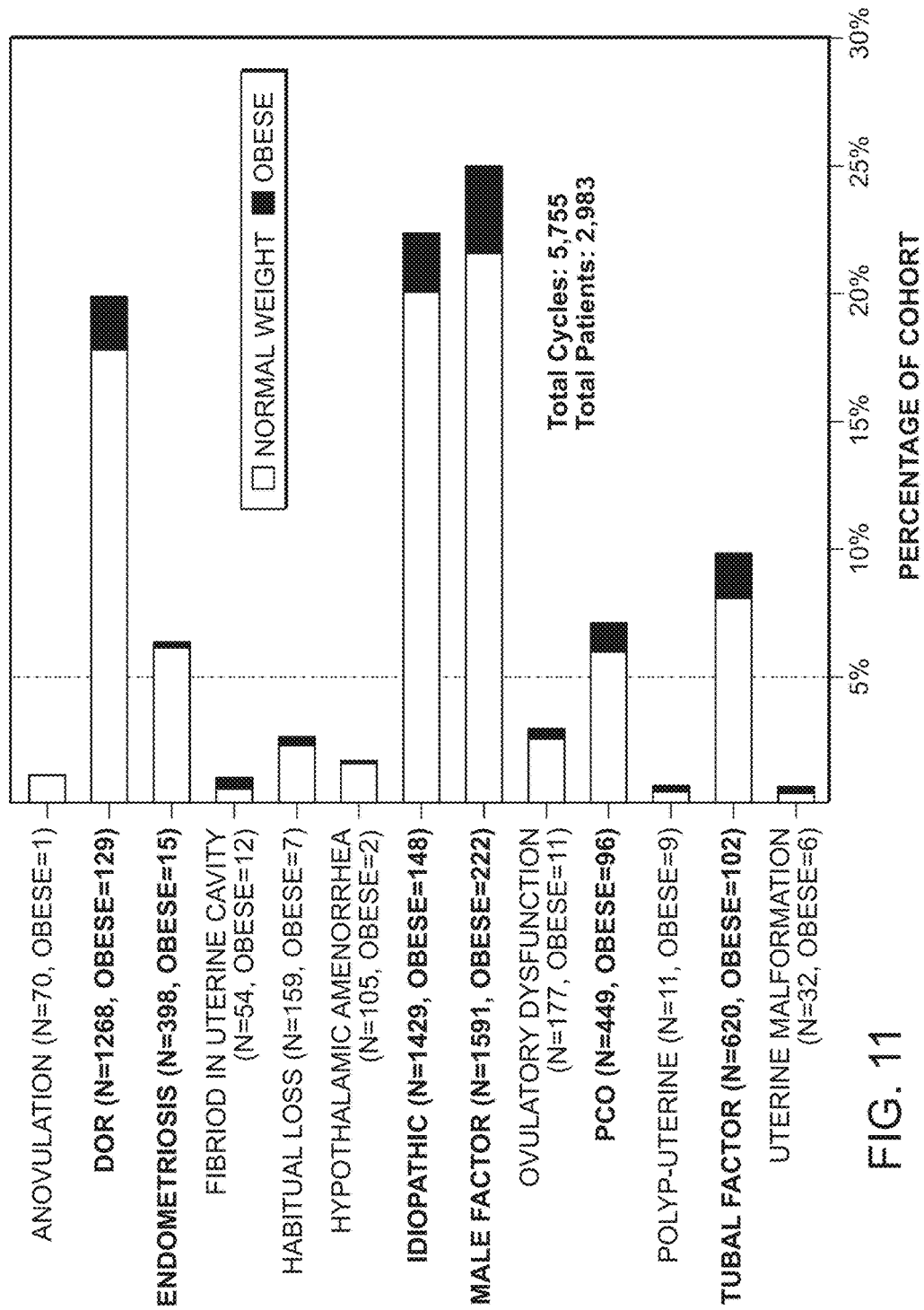
FIG. 11 illustrates the percentage of cohort for several diagnosis groups.
Figure 12:
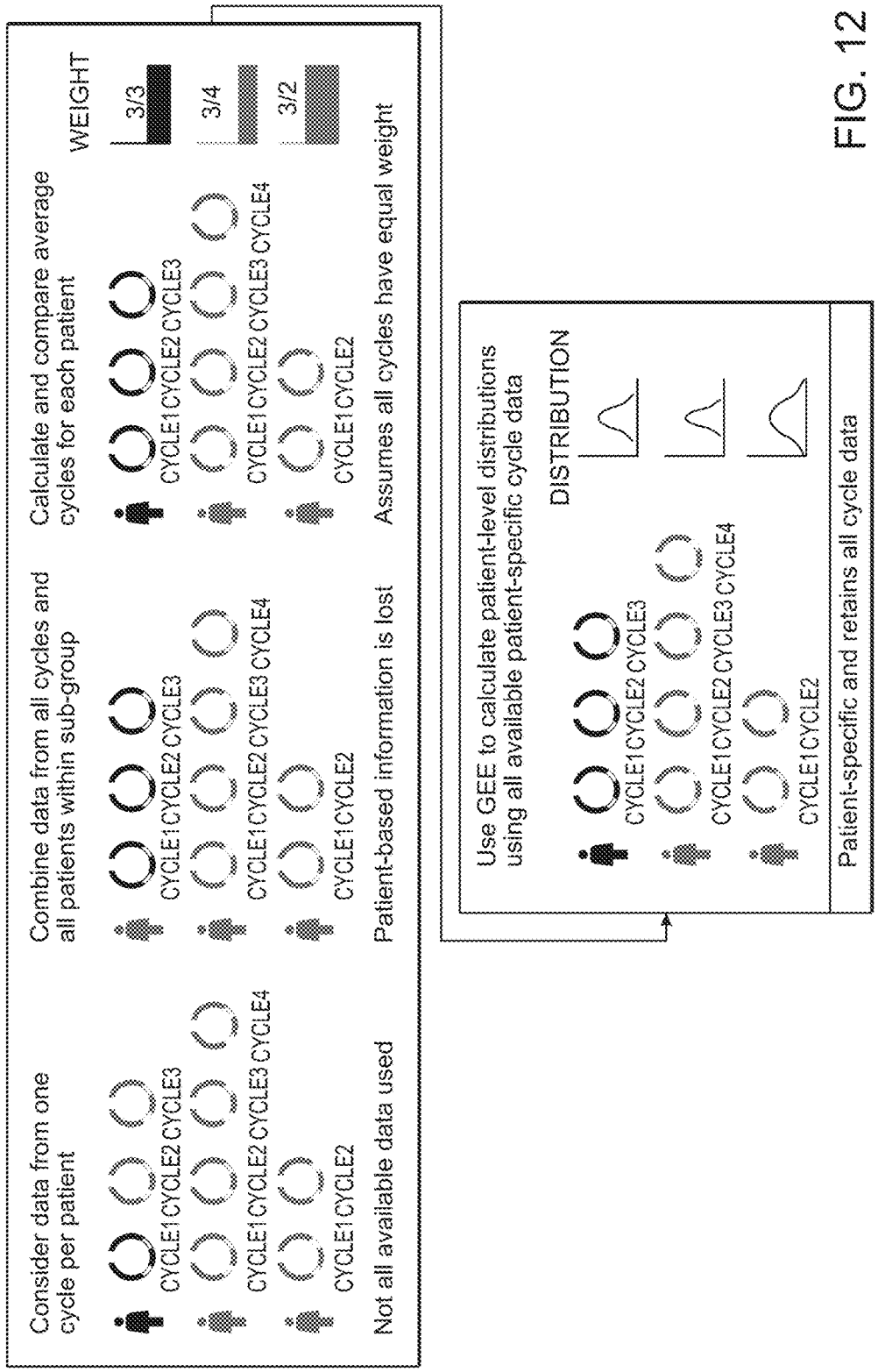
FIG. 12 illustrates methods for analyzing multi-cycle IVF data.

In the study discussed in example 3 below, among PCOS patients, obesity had significant negative effects on implantation rate by odds ratio, or OR (<50%, OR=0.55, p=0.02), clinical pregnancy (OR=0.57, p=0.03) and live birth (OR=0.44, p=0.02) outcome while no significant adverse effects from obesity were determined for other patient groups (i.e., diminished ovarian reserve, endometriosis, idiopathic, male factor, PCOS, and tubal factor). FIG. 11 illustrates the percentage of cohort for patient groups in the study. FIG. 12 illustrates methods for analyzing multi-cycle IVF data including the method used in the study discussed below where generalized estimation equation (GEE) is used to calculate patient-level distributions using all available patient-specific IVF cycle data.

Figure 13:
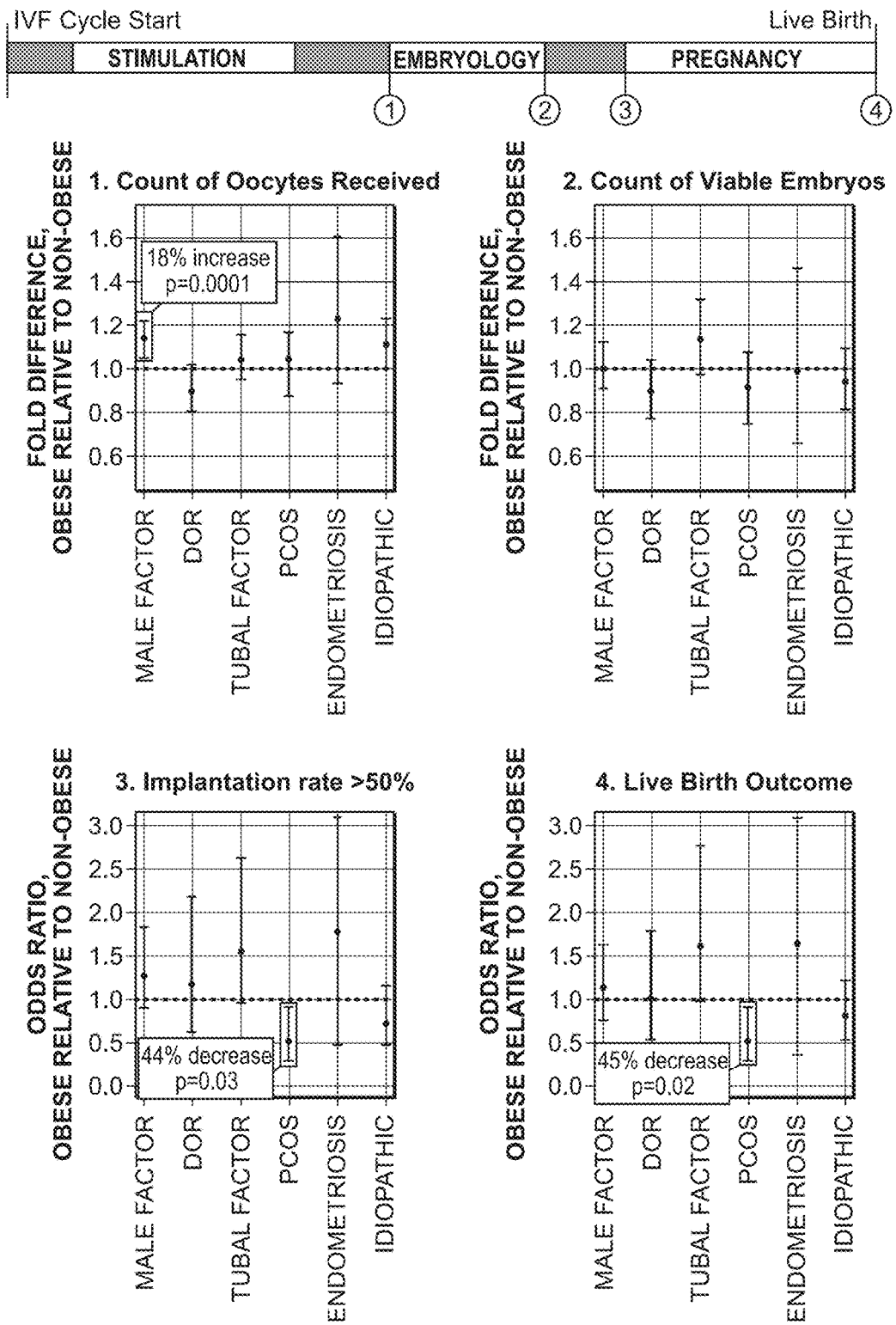
FIG. 13 illustrates the impact of obesity on oocyte retrieval, number of viable embryos, implantation rate, and live birth outcomes for several diagnosis groups.

For PCOS patients, obesity increases the risk of IVF treatment failure over two-fold and, specifically, obesity was found to adversely affect implantation rate, clinical pregnancy and live birth outcomes, obesity was found to have a negative influence on uterine receptivity and embryo implantation for PCOS patients. FIG. 13 illustrates the impact of obesity on oocyte retrieval, number of viable embryos, implantation rate, and live birth outcomes for patient groups including patients suffering from diminished ovarian reserve, endometriosis, idiopathic, male factor, PCOS, and tubal factor showing a significant decrease in implantation rate and number of live birth outcomes for obese PCOS patients.

Methods of the invention include determining a likelihood of IVF treatment success for a patient or individual based on a PCOS diagnosis and a measure of obesity. Body fat may be indicated by weight, waist circumference (e.g., the circumference of the abdomen, measured at the natural waist (in between the lowest rib and the top of the hip bone), the umbilicus (belly button), or at the narrowest point of the midsection), waist-to-hip ratio (e.g., calculated by measuring the waist and the hip (at the widest diameter of the buttocks), and then dividing the waist measurement by the hip measurement), skinfold thickness (e.g., using a special caliper to measure the thickness of a "pinch" of skin and the fat beneath it in specific areas of the body and using equations to predict body fat percentage based on these measurements), bioelectrical impedance (see, Hu F. Measurements of Adiposity and Body Composition. In: Hu F, ed. Obesity Epidemiology. New York City: Oxford University Press, 2008; 53-83, incorporated herein in its entirety), underwater weighing (densitometry), air-displacement plethysmography, dilution method (magnetic resonance imaging, or dual energy X-ray absorptiometry. In a preferred embodiment, body fat is indicated by body mass index (BMI). BMI is the ratio of weight to height, calculated as weight (kg)/height (m2), or weight (lb)/height (in2) multiplied by 703.

Body fat, as measured by one of the methods above, can then be compared to a reference number to determine if the individual is obese. Diminished success rates for PCOS diagnosed individuals may be indicated where, for instance, BMI is determined to be greater than 25, 26, 27, 28, 29, 30, 31, 32, 33, 34, or 35 kg/m$^2$. In a preferred embodiment, a BMI greater than 30 kg/m$^2$ is considered to obese and at higher risk of IVF failure.

In certain embodiments, systems and methods of the invention include receiving a PCOS diagnosis for a patient. In other embodiments, systems and methods may include diagnosing PCOS in an individual through, for example, one of the methods described in Sheehan, Polycystic Ovarian Syndrome: Diagnosis and Management, Clin Med Res. 2004 February; 2(1): 13-27.

After obtaining or determining a PCOS diagnosis and an indication of obesity in an individual, methods of the invention may include determining a likelihood of IVF success for the individual (e.g., represented by a % score indicating a likelihood of live birth after IVF treatment, a % reduction from average success rate, or an estimated number of cycles to achieve live birth). The likelihood of IVF success rate may be reported to the individual or the individual's physician alone or in combination with other fertility information In certain embodiments, the PCOS and obesity information may be combined with other factors to determine an overall likelihood of IVF success for the patient or to provide treatment recommendations for the patient.

In the study discussed in example 4 below, a large cohort of retrospective pre-implantation genetic screening (PGS) data was studied to clarify the respective contributions of FSH and age to aneuploidy. While no age-independent association between FSH and aneuploidy odds was found, the age-associated increase in aneuploidy odds was more pronounced in patients with FSH levels above 13 mUI/mL where odds of aneuploidy increased at a substantially higher rate (50%) for each additional year (OR=1.52, p<0.0001) of life.

Methods of the invention include determining a woman's relative risk of producing an aneuploid embryo based upon her age and her FSH level. FSH level may be determined from a body fluid such as urine or blood. A sample may be obtained directly from the patient or may be received. Because urine levels of FSH vary throughout the day, in certain embodiments, urine may be collected over a 24-hour period before FSH levels are determined. FSH levels in the sample may be determined using a laboratory procedure such as an immunofluorometric assay. See Kesner J S, Knecht E A, Krieg E F., Jr Time-resolved immunofluorometric assays for urinary luteinizing hormone and follicle stimulating hormone. Anal Chim Acta. 1994; 285:13-22 incorporated herein by reference in its entirety.

A greater increase, by age, of aneuploidy rates may be indicated where the FSH level for a woman is greater than as threshold level such as, for example, 10, 11, 12, 13, 14, or 15 mUI/ML. In a preferred embodiment, where a woman's FSH level is above 13 mUI/mL, she may be at an increased risk of producing aneuploid embryos as she ages. In various embodiments, the woman's risk of producing an aneuploid embryo may be determined from her FSH levels and her age above puberty or fertility. Where the woman's FSH level is below the threshold level, the risk may be increased by 8%, 9%, 10%, 11%, or 12% (from an initial or base risk level) for each year of her reproductive lifespan (e.g., time from beginning of puberty to menopause, or from beginning of regular ovulation to menopause). Where the woman's FSH level is above the threshold level, the risk may be increased by 13%, 14%, 15%, 16%, or 17% (from an initial or base risk level) for each year of her reproductive lifespan. In certain instances, reproductive lifespan may be determined for an individual based on the actual age they reached puberty or began regular ovulation (as determined, for example, by a detailed patient history) or may be assumed to have begun at standard age such as 12, 13, 14, 15, 16, or 17. An initial or base risk of producing an aneuploid embryo may be determined from an average rate among the population or taken from known studies such as Franasiak, et al., The nature of aneuploidy with increasing age of the female partner: a review of 15,169 consecutive trophectoderm biopsies evaluated with comprehensive chromosomal screening, Fertil Steril. 2014 March; 101(3):656-663; incorporated herein in its entirety.

In certain embodiments, systems and methods of the invention may include reporting to this increased risk to the patient, physician, or other individual, where the patient's FSH level is greater than 13 mUI/mL. Various embodiments may include recommending or performing a treatment for the patient including avoiding certain assistive reproductive technologies, beginning treatments earlier, or, in some cases, harvesting eggs or embryos and storing for later use in assistive reproductive technologies such as IVF. Methods for retrieving and/or storing eggs and embryos are known. See Cil, et al., Current trends and progress in clinical applications of oocyte cryopreservation, Curr Opin Obstet Gynecol. 2013 June; 25(3); Killick, S (2006). "Ultrasound and fertility". In Bates, J. Practical gynaecological ultrasound (2nd ed.). Cambridge, England: Cambridge University Press. pp. 120-5; the contents of which are incorporated herein in their entirety.

Reports as referred to herein may be produced in written form on paper or in a computer file and may be prepared by a computing device and sent to a user (e.g., patient, physician or other individual) through an input/output device such as a monitor, interactive display, or printer, for example.

Methods of the invention may be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. For example, the reference set of data may be stored at a remote location and the computer communicates across a network to access a reference set of data for all patients along with clinical outcomes (e.g., IVF success rates) to compare data derived from the female subject to the reference set. In other embodiments, however, the reference set is stored locally within the computer and the computer accesses the reference set within the CPU to compare subject data to the reference set. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

In an exemplary embodiment shown in FIG. 14, system 200, capable of carrying out methods of the invention, can include a computer 249 (e.g., laptop, desktop, or tablet). The computer 249 may be configured to communicate across a network 209. Computer 249 includes one or more processor 259 and memory 263 as well as an input/output mechanism 254. Where methods of the invention employ a client/server architecture, an steps of methods of the invention may be performed using server 213, which includes one or more of processor 221 and memory 229, capable of obtaining data, instructions, etc., or providing results via interface module 225 or providing results as a file 217. Server 213 may be engaged over network 209 through computer 249 or terminal 267, or server 213 may be directly connected to terminal 267, including one or more processor 275 and memory 279, as well as input/output mechanism 271.

Systems 200 or machines according to the invention may further include, for any of I/O 259 or 237, or interface module 225, a video display unit (e.g., a liquid crystal display (LCD) or a cathode ray tube (CRT)). Computer systems or machines according to the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 263, 279, or 229 according to the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

It will be understood that any portion of the systems and methods disclosed herein, can be implemented by computer, including the devices described above. Information is collected from a female subject. This data is then inputted into the central processing unit (CPU) of a computer. The CPU is coupled to a storage or memory for storing instructions for implementing methods of the present invention. The instructions, when executed by the CPU, cause the CPU to provide a probability of successful in vitro fertilization in a selected cycle of in vitro fertilization. The CPU provides this determination by inputting the subject data into an algorithm trained on a reference set of data from a plurality of women for whom fertility-associated phenotypic traits and pregnancy outcomes for each cycle of IVF is known. The reference set of data may be stored locally within the computer, such as within the computer memory. Alternatively, the reference set may be stored in a location that is remote from the computer, such as a server. In this instance, the computer communicates across a network to access the reference set of data. The CPU then provides a probability of achieving pregnancy at a selected point in time based on the data entered into the algorithm.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore

EXAMPLE 1

Several studies have compared the gene expression signatures of tissue from normal and endometriosis patients, identifying significant differences in the expression of particular functional pathways, such as focal adhesion, tissue remodeling and immune response.

However, there is often discrepancy in the identity of the genes themselves, most likely being a product of inter-experimental patient variability, tissue type, cohort size, experimental technique, significance thresholds etc. To help more faithfully define of the gene expression signature consistently associated with endometriosis, a meta-analysis of microarray data is drawn from several published papers.

The aim of the meta-analysis is to determine whether comparison of this signature with patient specific gene expression data leads to the identification genes whose differential expression is derived from patient-specific genetic variation, as opposed to those whose expression changes merely as a product of endometriosis.

Methodology:
Datasets:
GSE23339 (Hawkins et al., 2011): ovarian endometrioma vs eutopic endometrium from a *separate* group of normal patients.
GSE7846, GSE6364 (Sha et al., 2007; Burney et al., 2007): eutopic endometrium from endometriosis patients vs separate group of normal patients.
A normalized expression matrix was computed for each study: For Affymetrix data, RMA normalization was used (Rafael et al., 2003). For Illumina, the log 2 normalized values reported in the original publications were used.
QC metrics were calculated using Bioconductor packages (Gentleman et al., 2004) such as arrayQualityMetrics and affyQCReport.
The case control analyses were performed within each study using an empirical Bayes moderated t-test for each transcript. Results were combined across studies using a fixed effects meta-analysis, combining transcripts for a given gene across studies, and weighting by the inverse of the variances estimates for each transcript. The meta-analysis thus yielded a consensus mean, associated standard error, t-score, and p-value for each gene. False discovery rates were estimated using standard methods.
Pathway analysis was performed using SPIA (signaling pathway impact analysis). Gene ontology analysis was performed using both i) a Fisher's Exact test on the counts of significant genes (p<0.005) in and not in a given GO term, and ii) a Wilcoxon Rank Sum test on the gene specific t scores comparing genes in and not in a given GO term.

Results:
See Pathways List (below): It appears that the more 'specific' the pathway categories are, the lower the magnitude of the difference between endometriosis and normal sample gene expression. This might suggest that endometriosis is a disease of 'many genes', as opposed to a handful of specific drivers. This would fit with its heterogeneous etiology, as well as the fact that studies do not seem to reach a consensus on the endometriosis expression signature.
In accordance with existing literature, pathway categories with the highest magnitude include chemokine/cytokine signaling and other immune response mechanisms, focal adhesion, extra-cellular matrix interactions, and angiogenesis (See 'Pathways' list.)
Similarly, among the list of genes (see below) whose expression is significantly different in association with endometriosis, the upregulation of CCL3L1, CCL3, FAM180A, THBS2, PDGFRL, FN1, CLEC11A all reflect the invasive tissue remodeling and immune-response associated with the development of endometriosis.
There are another two interesting pathways that are identified as significant but that have been less discussed in previous studies. These might be worth more careful consideration:
1. Leukocyte Transendothelial Migration.
Most likely, this is detected as significant at least partly due to the presence of immunocytes in endometriotic tissue. However, while previous studies have argued that endometriosis is invasive but not strictly metastatic, the expression of a number of the genes in the LTM pathway is not specific to leukocytes or leukocyte migration:
ACTG1, Claudin-4 and EZR, among others, have all been implicated in the mediation of cell motility in different cancer types.
Furthermore, among genes whose expression is most altered in the endometriotic state, 2 of the most upregulated genes include matrix metalloproteinase 23B (MMP23B, 2.029 fold increase, confidence=11.03) and thrombospondin 2 (THBS2, 2.012 fold increase, confidence=5.037).
MMP23 has been found to be predominantly expressed in reproductive tissues (Velasco et al., 1999). Degradation of ECM is essential for cells to invade the peritoneum. MMPs are involved in the breakdown of extracellular matrix during embryonic development and reproduction, as well as arthritis and metastasis (reviewed by Christiane et al., 2014).
THBS2 modulates cell-matrix interactions, and interestingly, is involved with integrin aVB3 in the modulation of cell spreading and migration of endothelial cells (Bornstein et al., 2000).
Similarly, OSR2 is significantly downregulated (0.712 fold, confidence=12.65). TGF-beta1-mediated downregulation of this transcription factor is associated with the induction of cell migration (Kawai et al., 2012). TGFB1 is actually enriched at sites of ectopic endometrium (Komiyana et al., 2007; Medina and Lebovic, 2010).
2. Axon Guidance/Semaphorin Interactions.
Biological neuronal markers indicate specific types of nerve fibers present within endometrial layers (Tokushige et al., 2006).
There is some literature describing nerve fiber density differences between women with diagnosed endometriosis and women without endometriosis but no indication as to a driving mechanism.
Our identification of significant gene expression would be (at least among) the first to suggest a mechanism by which this increased innervation might take place.
Our analysis reveals that a number of genes involved in axon guidance are significantly upregulated in association with endometriosis, eg:
ROBO3, which competes with ROBOT/2, representing an anti-repulsion mechanism;
SEMA7A, in the absence of which neuroendocrine cell migration is impaired in mice (Messina et al., 2011).

| | Gene List for Example 1: Gene Expression Signatures associated with Endometriosis | | | | | |
|---|---|---|---|---|---|---|
| | Gene | Link | Degree of Dif | Confidence | AKA | Details |
| 326 | SPRR2F | SPRR2F | 6.83 | 4.012 | | Involved in the inflammatory stress response (Gleyzer and Scarpulla, 2013) Possibly endometrium specific (Contreras et al., 2010) |
| 366 | CCL3L1 | CCL3L1 | 3.864 | 3.037 | | Cytokines are secreted proteins that function in inflammatory and immunoregulatory processes, via their interaction with several chemokine receptors, including chemokine binding protein 2 and chemokine (C-C motif) receptor 5 (CCR5). The copy number of this gene varies among individuals, where most individuals have one to six copies, and a minority of individuals have zero or more than six copies. There are conflicting reports about copy number variation of this gene and its correlation to disease susceptibility. |
| 364 | CCL3 | CCL3 | 3.697 | 3.161 | | This locus represents a small inducible cytokine. The encoded protein, also known as macrophage inflammatory protein 1 alpha, plays a role in inflammatory responses through binding to the receptors CCR1, CCR4 and CCR5. |
| 372 | HLA-DRB3 | HLA-DRB3 | 3.461 | 2.491 | | Expressed in antigen presenting cells - constitutes part of the histocompatibility complex. |
| 1 | LOC100240735 | LOC100240735 | 3.431 | 16 | | |
| 322 | ADAMTS9-AS1 | ADAMTS9-AS1 | 3.429 | 4.047 | | |
| 70 | FAM180A | FAM180A | 2.898 | 6.725 | | Expression is TGF-B dependent in mammalian systems (Kosla et al., 2013) |
| 361 | NCF1 | NCF1 | 2.487 | 3.229 | | Neutrophil cytosolic fator - reflecting the accumulation of white blood cells, commonly associated with ednometriosis. |
| 15 | DACT1 | DACT1 | 2.155 | 11.802 | | Dishevelled signaling mediator - antoagonist of beta-catenin, therefore potentially contributing to the 'metastatic' pathology of endometriosis, through mediating loss of adhesion? |
| 175 | ITLN2 | ITLN2 | 2.122 | 5.107 | | Possibly involved in immune response? |
| 227 | C3 | C3 | 2.059 | 4.682 | | Complement component 3 - complement activation. |
| 23 | REP15 | REP15 | 2.047 | 9.911 | | |
| 17 | MMP23B | MMP23B | 2.029 | 11.031 | | A metallopeptidase involved in the breakdown of extracellular matrix during embryonic development and reproduction, as well as arthritis and metastasis . . . |

| | Gene List for Example 1: Gene Expression Signatures associated with Endometriosis | | | | | |
|---|---|---|---|---|---|---|
| | Gene | Link | Degree of Dif | Confidence | AKA | Details |
| 12 | CFH | CFH | 2.025 | 12.259 | | Degradation of ECM is essential for cells to invade the peritoneum Member of the Regulator of Complement Activation (RCA) gene cluster. Encodes a protein with twenty short consensus repeat (SCR) domains. Secreted into the bloodstream and has an essential role in the regulation of complement activation, restricting this innate defense mechanism to microbial infections. |
| 181 | THBS2 | THBS2 | 2.012 | 5.037 | | Modulates cell-matrix interactions, and interestingly, is involved with integrin aVB3 in the modulation of endothelial cell properties like cell spreading and migration (Bornstein et al, 2000) |
| 101 | IGDCC4 | IGDCC4 | 1.945 | 6.109 | | Immunoglobulin superfamily |
| 375 | FLJ41200 | FLJ41200 | 1.945 | 2.259 | | |
| 54 | LOC100506700 | LOC100506700 | 1.714 | 7.257 | | |
| 204 | PDGFRL | PDGFRL | 1.682 | 4.87 | | |
| 11 | FAM101B | FAM101B | 1.671 | 12.474 | | |
| 2 | FN1 | FN1 | 1.668 | 16 | Fibronectin | Cell adhesion, migration, embryogenesis, wound healing, blood coagulation, host defense |
| 355 | SCG5 | SCG5 | 1.662 | 3.492 | | |
| 3 | CLEC11A | CLEC11A | 1.635 | 16 | C-type lectin domain family 11, | Growth factor for primitive hematopoietic progenitor cells |
| 346 | HIST2H2BF | HIST2H2BF | 1.635 | 3.78 | | |
| 343 | FLJ27354 | FLJ27354 | 1.594 | 3.855 | | |
| 6 | PLTP | PLTP | 1.577 | 13.447 | | |
| 180 | CDCA7L | CDCA7L | 1.576 | 5.052 | | |
| 48 | S100A10 | S100A10 | 1.571 | 7.426 | | |
| 94 | LBH | LBH | 1.57 | 6.259 | | |
| 293 | MGC24103 | MGC24103 | 1.566 | 4.316 | | |
| 119 | NID2 | NID2 | 1.564 | 5.792 | | |
| 287 | SGK1 | SGK1 | 1.546 | 4.356 | | |
| 201 | OR2A9P | OR2A9P | 1.538 | 4.897 | | |
| 363 | TXNDC5 | TXNDC5 | 1.53 | 3.165 | | |
| 281 | LOC339524 | LOC339524 | 1.527 | 4.435 | | |
| 190 | SLC7A5P2 | SLC7A5P2 | 1.508 | 4.996 | | |
| 289 | FMOD | FMOD | 1.503 | 4.336 | | |
| 318 | MATN2 | MATN2 | 1.498 | 4.074 | | |
| 39 | KCTD12 | KCTD12 | 1.492 | 7.786 | | |
| 351 | C1R | C1R | 1.462 | 3.647 | | |
| 278 | CXCL12 | CXCL12 | 1.454 | 4.471 | | |
| 323 | LOC648570 | LOC648570 | 1.448 | 4.042 | | |
| 332 | STEAP1 | STEAP1 | 1.444 | 3.966 | | |
| 335 | HMOX1 | HMOX1 | 1.44 | 3.951 | | |
| 250 | SNAI2 | SNAI2 | 1.438 | 4.587 | | |
| 348 | NFKBIZ | NFKBIZ | 1.436 | 3.724 | | |
| 352 | DHRS4 | DHRS4 | 1.432 | 3.585 | | |
| 327 | LY96 | LY96 | 1.417 | 4.012 | | |
| 336 | LOXL1 | LOXL1 | 1.417 | 3.942 | | |
| 328 | IL32 | IL32 | 1.414 | 4.009 | | |
| 97 | GUCY1B3 | GUCY1B3 | 1.413 | 6.21 | | |
| 38 | GPC6 | GPC6 | 1.405 | 7.837 | | |
| 313 | OR2A20P | OR2A20P | 1.4 | 4.146 | | |
| 64 | PGCP | PGCP | 1.397 | 6.848 | | |
| 317 | JSRP1 | JSRP1 | 1.387 | 4.127 | | |
| 338 | TUBB6 | TUBB6 | 1.384 | 3.918 | | |
| 324 | ZFPM2 | ZFPM2 | 1.383 | 4.026 | | |
| 240 | GLT8D2 | GLT8D2 | 1.38 | 4.628 | | |

-continued

Gene List for Example 1: Gene Expression Signatures associated with Endometriosis

| | Gene | Link | Degree of Dif | Confidence | AKA | Details |
|---|---|---|---|---|---|---|
| 40 | HSD17B11 | HSD17B11 | 1.377 | 7.754 | | |
| 152 | PMP22 | PMP22 | 1.375 | 5.417 | | |
| 118 | ECHDC3 | ECHDC3 | 1.368 | 5.802 | | |
| 222 | DFNA5 | DFNA5 | 1.362 | 4.709 | | |
| 263 | ATL1 | ATL1 | 1.362 | 4.536 | | |
| 349 | TOMM7 | TOMM7 | 1.36 | 3.717 | | |
| 29 | GYPC | GYPC | 1.354 | 8.632 | | |
| 127 | PABPC4L | PABPC4L | 1.351 | 5.694 | | |
| 276 | KLF10 | KLF10 | 1.346 | 4.494 | | |
| 295 | PRKCDBP | PRKCDBP | 1.338 | 4.303 | | |
| 288 | BGN | BGN | 1.327 | 4.338 | | |
| 80 | CNN3 | CNN3 | 1.326 | 6.538 | | |
| 202 | OSGIN1 | OSGIN1 | 1.326 | 4.885 | | |
| 90 | NEK7 | NEK7 | 1.322 | 6.33 | | |
| 321 | JUN | JUN | 1.32 | 4.054 | | |
| 155 | CNN2 | CNN2 | 1.317 | 5.332 | | |
| 143 | CTSL1 | CTSL1 | 1.316 | 5.552 | | |
| 285 | GPR141 | GPR141 | 1.315 | 4.39 | | |
| 345 | MN1 | MN1 | 1.315 | 3.815 | | |
| 9 | TAGLN | TAGLN | 1.314 | 12.763 | | |
| 340 | BST1 | BST1 | 1.31 | 3.912 | | |
| 22 | FLJ20021 | FLJ20021 | 1.303 | 9.949 | | |
| 21 | CASP4 | CASP4 | 1.301 | 10.271 | | |
| 177 | GLIPR2 | GLIPR2 | 1.301 | 5.105 | | |
| 217 | FOXO4 | FOXO4 | 1.301 | 4.767 | | |
| 103 | CLEC10A | CLEC10A | 1.297 | 6.068 | | |
| 314 | MSC | MSC | 1.292 | 4.139 | | |
| 43 | CSTA | CSTA | 1.289 | 7.564 | | |
| 334 | SACS | SACS | 1.289 | 3.957 | | |
| 16 | CTSC | CTSC | 1.286 | 11.537 | | |
| 174 | C14orf37 | C14orf37 | 1.279 | 5.114 | | |
| 330 | FLJ41309 | FLJ41309 | 1.277 | 3.999 | | |
| 325 | HOXC6 | HOXC6 | 1.276 | 4.013 | | |
| 107 | KLF6 | KLF6 | 1.272 | 5.988 | | |
| 296 | FKBP9 | FKBP9 | 1.271 | 4.293 | | |
| 55 | CDH11 | CDH11 | 1.27 | 7.166 | | |
| 298 | ZNF815 | ZNF815 | 1.269 | 4.283 | | |
| 312 | GLIPR1 | CLIPR1 | 1.267 | 4.174 | | |
| 62 | FAM70B | FAM70B | 1.263 | 6.876 | | |
| 272 | LGALS2 | LGALS2 | 1.261 | 4.507 | | |
| 27 | ICAM5 | ICAM5 | 1.259 | 8.771 | | |
| 246 | TMEM51 | TMEM51 | 1.259 | 4.61 | | |
| 19 | RGS10 | RGS10 | 1.253 | 10.426 | | |
| 69 | CHST15 | CHST15 | 1.248 | 6.73 | | |
| 116 | GRASP | GRASP | 1.245 | 5.818 | | |
| 44 | WWC3 | WWC3 | 1.244 | 7.553 | | |
| 316 | COL6A3 | COL6A3 | 1.242 | 4.135 | | |
| 150 | EMP1 | EMP1 | 1.241 | 5.423 | | |
| 42 | CAV2 | CAV2 | 1.238 | 7.57 | | |
| 194 | SORCS2 | SORCS2 | 1.237 | 4.984 | L | |
| 171 | GAS6 | GAS6 | 1.235 | 5.156 | | |
| 302 | LAPTM5 | LAPTM5 | 1.235 | 4.24 | | |
| 195 | AOAH | AOAH | 1.229 | 4.981 | | |
| 307 | SCT | SCT | 1.221 | 4.194 | | |
| 139 | RAB23 | RAB23 | 1.22 | 5.584 | | |
| 73 | GUCY2D | GUCY2D | 1.218 | 6.631 | | |
| 162 | PDE1B | PDE1B | 1.215 | 5.261 | | |
| 207 | ROM1 | ROM1 | 1.214 | 4.861 | | |
| 102 | CGREF1 | CGREF1 | 1.211 | 6.095 | | |
| 243 | ROBO3 | ROBO3 | 1.211 | 4.622 | | |
| 35 | CCM2 | CCM2 | 1.21 | 7.952 | | |
| 79 | LOC100505500 | LOC100505500 | 1.21 | 6.546 | | |
| 59 | HSD17B14 | HSD17B14 | 1.206 | 6.926 | | |
| 290 | LRRC3 | LRRC3 | 1.206 | 4.331 | | |
| 291 | C3orf54 | C3orf54 | 1.206 | 4.326 | | |
| 284 | PLS3 | PLS3 | 1.205 | 4.432 | | |
| 129 | CNIH | CNIH | 1.2 | 5.668 | | |
| 138 | ODZ4 | ODZ4 | 1.199 | 5.592 | | |
| 283 | EEF1A2 | EEF1A2 | 1.198 | 4.433 | | |
| 114 | COL6A2 | COL6A2 | 1.196 | 5.832 | | |
| 126 | SLC7A1 | SLC7A1 | 1.196 | 5.697 | | |
| 274 | PIK3CD | PIK3CD | 1.196 | 4.495 | | |
| 188 | ADAM8 | ADAM8 | 1.191 | 4.999 | | |
| 212 | ALDH1B1 | ALDH1B1 | 1.191 | 4.808 | | |
| 63 | NAT8B | NAT8B | 1.188 | 6.871 | | |

-continued

Gene List for Example 1: Gene Expression Signatures associated with Endometriosis

| | Gene | Link | Degree of Dif | Confidence | AKA | Details |
|---|---|---|---|---|---|---|
| 179 | ADAMTS2 | ADAMTS2 | 1.188 | 5.064 | | |
| 261 | RPL23AP53 | RPL23AP53 | 1.187 | 4.544 | | |
| 258 | ZNF703 | ZNF703 | 1.186 | 4.559 | | |
| 259 | ST3GAL1 | ST3GAL1 | 1.185 | 4.547 | | |
| 34 | GTSE1 | GTSE1 | 1.184 | 8.471 | | |
| 273 | LOC100507054 | LOC100507054 | 1.184 | 4.502 | | |
| 219 | C19orf40 | C19orf40 | 1.182 | 4.762 | | |
| 4 | GPR161 | GPR161 | 1.181 | 16 | | |
| 31 | RECQL | RECQL | 1.18 | 8.574 | | |
| 36 | FOXC1 | FOXC1 | 1.179 | 7.909 | | |
| 262 | CBS | CBS | 1.177 | 4.537 | | |
| 294 | ZMYND15 | ZMYND15 | 1.177 | 4.314 | | |
| 218 | ACAP1 | ACAP1 | 1.176 | 4.765 | | |
| 249 | EGFLAM | EGFLAM | 1.174 | 4.589 | | |
| 286 | RAD51AP2 | RAD51AP2 | 1.174 | 4.377 | | |
| 238 | SHISA4 | SHISA4 | 1.173 | 4.637 | | |
| 275 | SH3BGRL | SH3BGRL | 1.173 | 4.495 | | |
| 8 | ARPC2 | ARPC2 | 1.172 | 13.069 | | |
| 244 | C21orf30 | C21orf30 | 1.172 | 4.62 | | |
| 18 | POU2F2 | POU2F2 | 1.171 | 10.542 | | |
| 153 | TIMP2 | TIMP2 | 1.171 | 5.363 | | |
| 208 | ZNF503 | ZNF503 | 1.171 | 4.847 | | |
| 85 | TLE3 | TLE3 | 1.168 | 6.434 | | |
| 185 | BEGAIN | BEGAIN | 1.168 | 5.023 | | |
| 81 | IKBIP | IKBIP | 1.167 | 6.532 | | |
| 33 | FAM20C | FAM20C | 1.166 | 8.548 | | |
| 68 | FTL | FTL | 1.165 | 6.762 | | |
| 164 | GSTO1 | GSTO1 | 1.165 | 5.209 | | |
| 125 | SEMA7A | SEMA7A | 1.162 | 5.707 | | |
| 225 | EID1 | EID1 | 1.157 | 4.685 | | |
| 282 | SCARF2 | SCARF2 | 1.155 | 4.434 | | |
| 117 | C4orf3 | C4orf3 | 1.154 | 5.817 | | |
| 158 | NAGS | NAGS | 1.154 | 5.323 | | |
| 159 | MYADM | MYADM | 1.154 | 5.304 | | |
| 214 | COL1A1 | COL1A1 | 1.154 | 4.789 | | |
| 266 | BCAS4 | BCAS4 | 1.154 | 4.529 | | |
| 93 | LAMP2 | LAMP2 | 1.152 | 6.26 | | |
| 100 | DCN | DCN | 1.151 | 6.115 | | |
| 148 | SLC43A3 | SLC43A3 | 1.15 | 5.478 | | |
| 30 | NR3C1 | NR3C1 | 1.149 | 8.614 | | |
| 187 | PLD2 | PLD2 | 1.147 | 5.008 | | |
| 267 | WDR53 | WDR53 | 1.147 | 4.527 | | |
| 24 | YBX1 | YBX1 | 1.145 | 9.76 | | |
| 170 | PIP4K2A | PIP4K2A | 1.145 | 5.157 | | |
| 67 | UNC13D | UNC13D | 1.144 | 6.769 | | |
| 221 | FOLR2 | FOLR2 | 1.144 | 4.71 | | |
| 77 | PTP4A2 | PTP4A2 | 1.143 | 6.577 | | |
| 26 | TNFRSF10C | TNFRSF10C | 1.142 | 8.802 | | |
| 199 | FIBCD1 | FIBCD1 | 1.142 | 4.91 | | |
| 145 | TPM2 | TPM2 | 1.14 | 5.534 | | |
| 130 | PSMA7 | PSMA7 | 1.134 | 5.649 | | |
| 223 | PDIA2 | PDIA2 | 1.133 | 4.703 | | |
| 133 | NR2F2 | NR2F2 | 1.132 | 5.604 | | |
| 271 | CMBL | CMBL | 1.132 | 4.513 | | |
| 163 | MICALCL | MICALCL | 1.129 | 5.222 | | |
| 203 | IPO5 | IPO5 | 1.129 | 4.878 | | |
| 206 | TNS1 | TNS1 | 1.123 | 4.864 | | |
| 247 | KCTD20 | KCTD20 | 1.123 | 4.607 | | |
| 265 | GNA12 | GNA12 | 1.122 | 4.529 | | |
| 132 | ASB1 | ASB1 | 1.119 | 5.613 | | |
| 231 | ADC | ADC | 1.119 | 4.662 | | |
| 198 | SPOCK2 | SPOCK2 | 1.116 | 4.914 | | |
| 52 | CDK6 | CDK6 | 1.112 | 7.313 | | |
| 233 | RBFOX2 | RBFOX2 | 1.112 | 4.656 | | |
| 229 | ST3GAL2 | ST3GAL2 | 1.111 | 4.678 | | |
| 192 | COMT | COMT | 1.108 | 4.986 | | |
| 235 | SEMA6B | SEMA6B | 1.106 | 4.653 | | |
| 51 | HSP90AA1 | HSP90AA1 | 1.104 | 7.362 | | |
| 239 | FCGR2C | FCGR2C | 1.104 | 4.628 | | |
| 224 | ALPK2 | ALPK2 | 1.103 | 4.694 | | |
| 71 | MAST4 | MAST4 | 1.102 | 6.715 | | |
| 110 | IGHA1 | IGHA1 | 1.102 | 5.944 | | |
| 41 | COL6A1 | COL6A1 | 1.101 | 7.678 | | |

Gene List for Example 1: Gene Expression Signatures associated with Endometriosis

| | Gene | Link | Degree of Dif | Confidence | AKA | Details |
|---|---|---|---|---|---|---|
| 216 | LOC152225 | LOC152225 | 1.101 | 4.774 | | |
| 210 | RABGGTB | RABGGTB | 1.1 | 4.834 | | |

Pathways List for Example 1: Gene Expression Signatures associated with Endometriosis

| Name | Genes Dysregulated (/Genes in Pathway) | Dysregulated Genes ($p \leq 0.005$) | Magnitude | Log10p value | FDR |
|---|---|---|---|---|---|
| Chemokine signaling pathway | 22/184 | ADCY8; ARRB1; BRAF; CCL3, 3L1, 7; CXCL2, 12; CXCR5; DOCK2; GNG3, 7, 10; JAK3; LYN; NCF1; PIK3CD; PLCB4; PRKACG; RAP1A; ROCK1; SHC3 | 13.43 | 2.77 | 0.03 |
| Focal adhesion | 29/200 | ACTG1, N3; BCL2; BRAF; CAV2; COL1A1, 1A2, 5A1, 5A2, 6A1, 6A2, 6A3; EGFR; FN1; ITGB3; JUN; LAMA1; MYL9; PAK6; PARVA; PDGFA; PIK3CD; PPP1R12A; PTEN; RAP1A; ROCK1; SHC3; THBS2; VCL | 9.4 | 3.13 | 0.03 |
| Cytokine-cytokine receptor interaction | 24/260 | CCL3, 3L1, 7; CD40, 70; CSF1R; CXCL2, 12; CXCR5; EGFR; EPOR; IFNA5; IL12RB1, 17B, 20RB; OSM; PDGFA; PRL; TNFRSF10A, 10C, 10D, 13B; TNFSF9, 12 | 5.13 | 4.51 | 0 |
| *Staphylococcus Aureus* Infection | 11/52 | C1QB; C1R; C1S; C3; CFH; FCGR2C; HLA-DPB1, -DRB3; ITGB2; KRT10; SELPLG | 4.36 | 2.92 | 0.03 |
| Leukocyte transendothelial migration | 18/116 | ACTG1; ACTN3; CD99; CLDN4, 5; CXCL12; EZR; ITGB2; MAPK11; MSN; MYL9; NCF1; NCF2; OCLN; PIK3CD; RAP1A; ROCK1; VCL | 3.71 | 2.05 | 0.11 |
| ECM-receptor interaction | 12/84 | COL1A1, 1A2, 5A1, 5A2, 6A1, 6A2, 6A3; FN1; ITGB3; LAMA1; SV2C; THBS2 | 3.49 | 2.89 | 0.03 |
| Systemic lupus erythematosus | 26/124 | ACTN3; C1QB; C1R; C1S; C3; CD40; FCGR2C; H2AFJ; H2AFX; HIST1H2AC, AD, AE, BD, BE, BF, BG, BK; HIST1H3E; HIST1H4A; HIST2H2AB, AC, BE, BF; HLA-DPB1, -DRB3; SSB | 2.65 | 5.42 | 0 |
| Osteoclast Differentiation | 21/128 | ACP5; AKT2; FHL2; FYN; GAB2; JAK1; JUNB; LILRB1; MAPK8; NFATC1; PIK3CG; PIK3R1, R3; PPP3CA; SOCS3; TEC; TGFB2; TNFRSF1A, 11B | 1.31 | 1.95 | 0.13 |
| Sulfur relay system | 3/10 | CTU2; NFS1; TST | −0.54 | 1.39 | 0.42 |
| Pathogenic *E. Coli* infection | 13/56 | ACTG1; ARPC2; EZR; LY96; NCL; OCLN; ROCK1; TUBA3E; TUBB, 2B, 6, 8; YWHAQ | −2.23 | 2.68 | 0.03 |

EXAMPLE 2

Identification of Phase-Specific Genetic Signatures for Endometriosis

The ambiguous knowledge of the mechanisms of endometriosis development complicates its treatment. The accepted mechanism for endometriosis is retrograde menstruation, which is the backflow of menstrual fluid and associated endometrial cells through the fallopian tubes. See FIG. 3. As shown in FIG. 4, retrograde menstruation causes adhesion and proliferation of endometrial cells outside of the uterine. The ectopic endometrial growth causes inflammation, immune system evasions, and EP dependence/P4 resistances. FIG. 4 also sets forth other potential contributory factors of endometriosis, including the presence of Mullerian rests, endometrial stem cells, and metaplasia.

Methods of the invention, according to certain embodiments, rely on genetics and bioinformatics in order to identify clinically significant genetic signatures of endometriosis. The genetic signatures, determined via methods of the invention, can be used to classify a subject's clinical condition (e.g. uterine phase or grade of endometriosis) and can be used to target treatment.

Data Set

Figure 5:
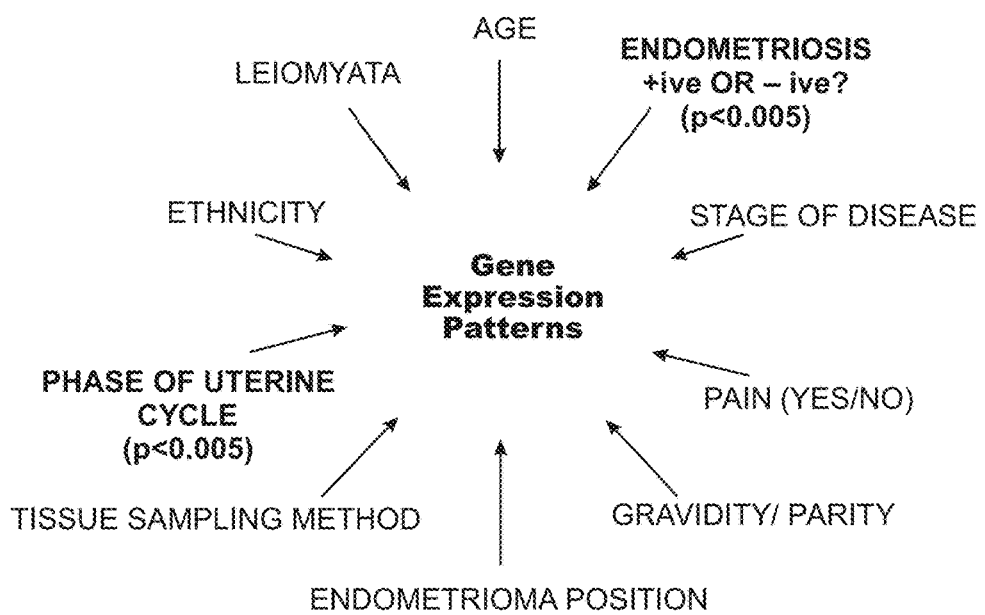
FIG. 5 illustrates various parameters examined in the meta-analysis of data and associated with endometriosis.

A meta-analysis was conducted to combined and correlate phase-specific micro-array data of several different endometrial studies. The following table lists the studies, type of microarray and the number of patients. Incorporating all of the studies, the meta-analysis analyzed data from 106 samples from 61 patients. The data from the study was subject to a meta-analysis as previously described. FIG. 5 illustrates the clinical parameters that were assessed for the micro-array studies: age, presence/absence of endometriosis, stage of the disease, presence of pain, gravidty/parity, endometrioma position, tissue sampling method, phase of the uterine cycle, ethnicity, and leiomyata.

| Study | Type of Array | #Patients |
|---|---|---|
| Burney, Richard O., et al. "Gene expression analysis of endometrium reveals progesterone resistance and candidate susceptibility genes in women with endometriosis." Endocrinology 148.8 (2007): 3814-3826 | Affymetrix, HG U133 + 2.0 | 21 |
| Crispi, Stefania, et al. "Transcriptional profiling of endometriosis tissues identifies genes related to organogenesis defects." Journal of cellular physiology 228.9 (2013): 1927-1934 | Affymetrix, U133A2.0 | 8 |
| Eyster, Kathleen M., et al. "Whole genome deoxyribonucleic acid microarray analysis of gene expression in ectopic versus eutopic endometrium." Fertility and sterility 88.6 (2007): 1505-1533 | GE/Amersham CodeLink, Human HG | 11 |
| Hever, Aniko, et al. "Human endometriosis is associated with plasma cells and overexpression of B lymphocyte stimulator." Proceedings of the National Academy of Sciences 104.30 (2007): 12451-12456 | Affymetrix, HG U133 + 2.0 | 10 |
| Hull, M. Louise, et al. "Endometrial-peritoneal interactions during endometriotic lesion establishment." The American journal of pathology 173.3 (2008): 700-715 | Affymetrix, HG U133A | 9 |
| Talbi, S., et al. "Molecular phenotyping of human endometrium distinguishes menstrual cycle phases and underlying biological processes in normo-ovulatory women." Endocrinology 147.3 (2006): 1097-1121. | Affymetrix, HG U133 + 2.0 | 16 |

Results

Figure 6A:
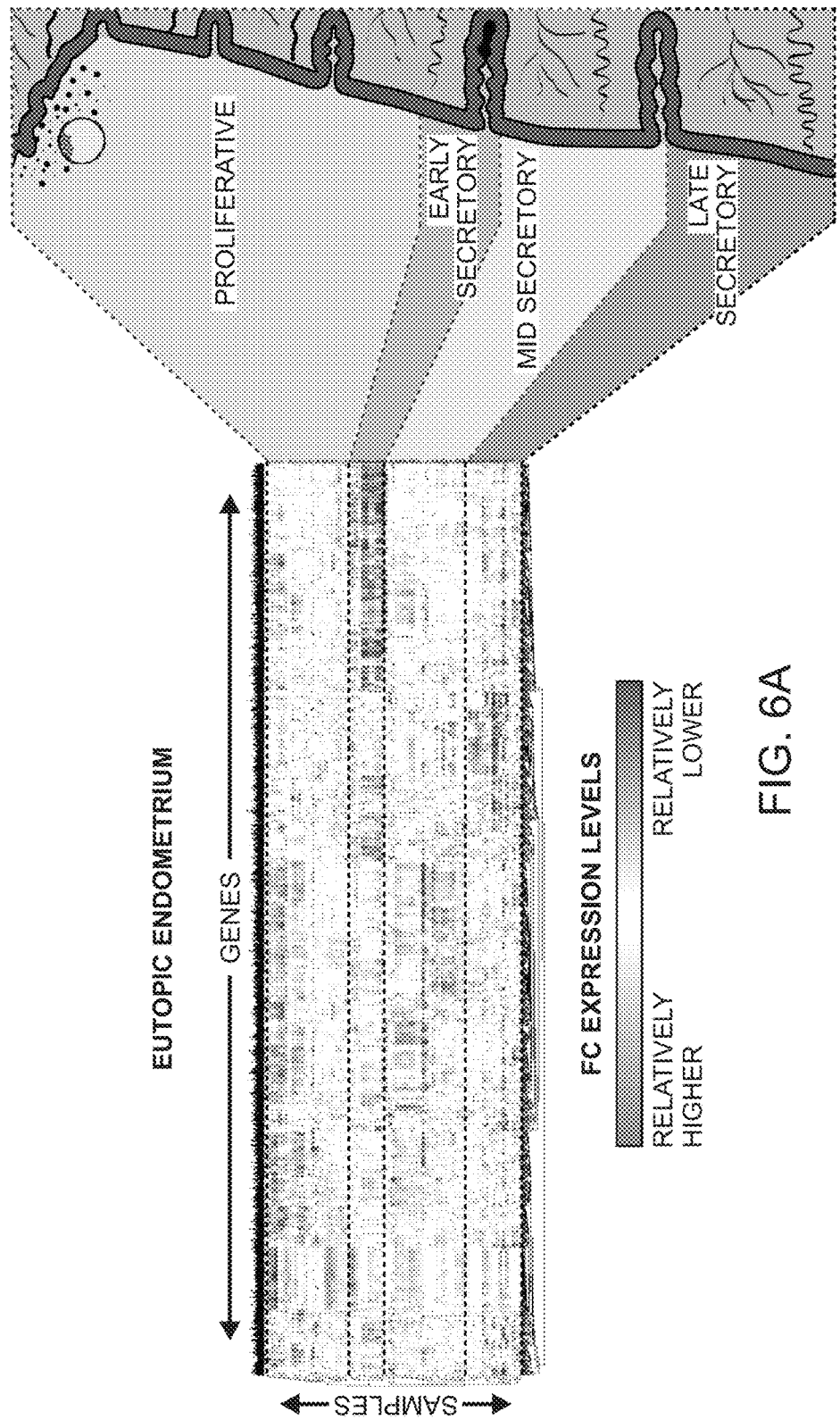
FIG. 6A illustrates gene expression of the eutopic endometrium of the samples across the proliferative, early secretory, mid-secretory, and late secretory phases.
Figure 6B:
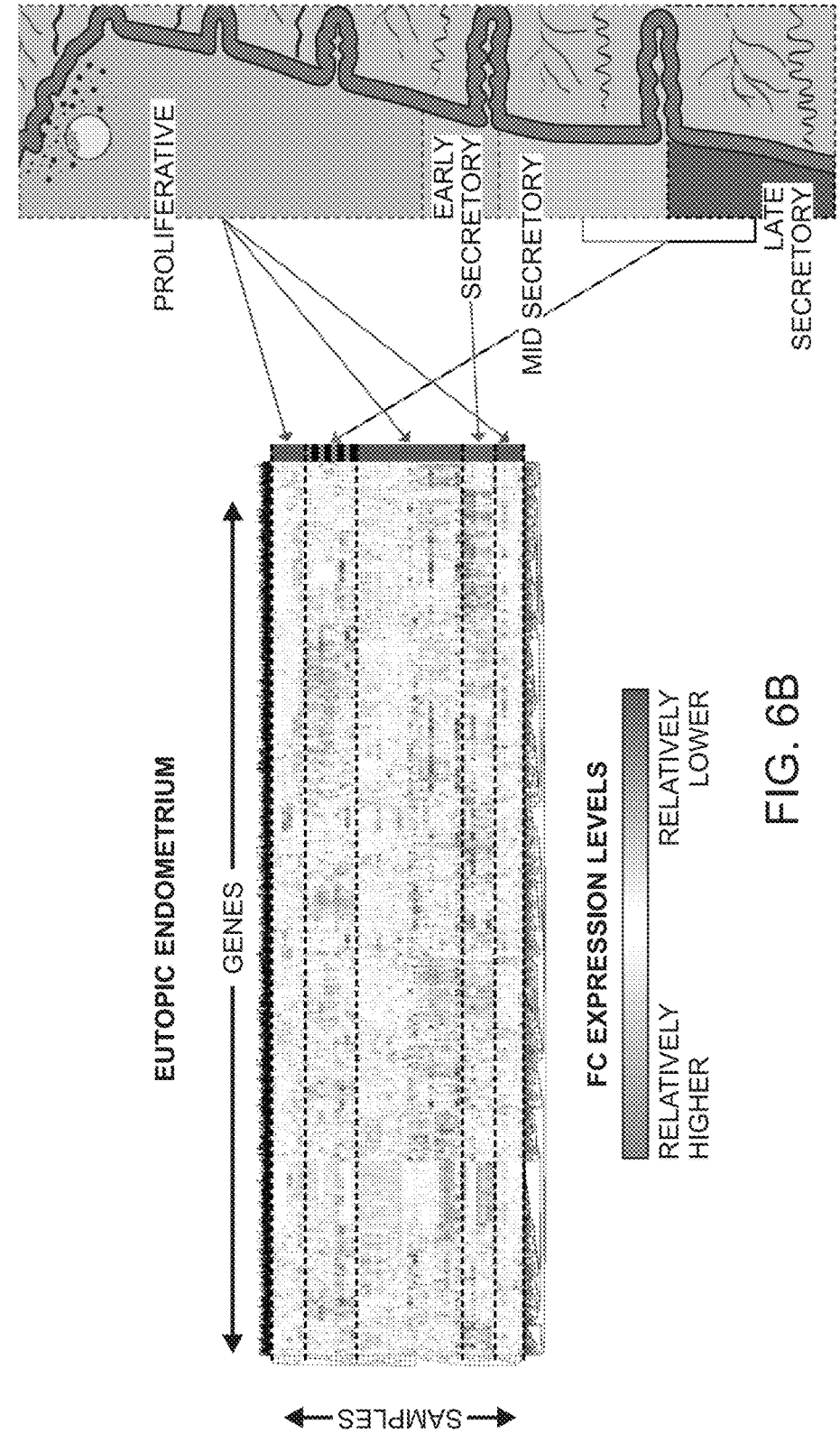
FIG. 6B illustrates gene expression of the ectopic endometrium of endometriosis positive samples across the proliferative, early secretory, mid-secretory, and late secretory phases.

Based on the meta-analysis, the parameters that dominated gene expression patterns include: 1) the phase of the uterine cycle and 2) the presence/absence of endometriosis. FIG. 6A illustrates gene expression of the eutopic endometrium of the samples across the proliferative, early secretory, mid-secretory, and late secretory phases. FIG. 6B illustrates gene expression of the ectopic endometrium across the proliferative, early secretory, mid-secretory, and late secretory phases. K-means clustering analysis of the micro-array data indicated showed that genetic signatures that ectopic and eutopic endometrial tissue were phased dependent in different ways.

The endometriosis phase-specific expression patterns were compared to the normal phase-specific expression patterns in order to identify genetic expression signatures specific to endometriosis and specific to a certain phase of the uterine cycle. FIG. 7 illustrates the phase-specific genetic signature differences between endometriosis and normal populations. The proliferative phase showed 430 genes with a fold-change greater than 2.0 (P-value less than 0.0005), the early secretory phase showed 151 genes with a fold-change greater than 2.0 (P-value less than 0.0005), and the mid-late secretory phase showed 3 genes with a fold-change greater than 2.0 (P-value less than 0.0005).

As illustrated in FIGS. 8-10, the meta-analysis revealed that certain genes of the endometriosis samples are up-regulated and down-regulated as compared to the normal. In addition, the misregulation of genes of the endometriosis sample varied across the different phases. The phase-specific regulation pattern of genes associated with endometriosis can be used as a regulation signature of the disease. FIG. 8 illustrates up-regulated and de-regulated genes associated with endometriosis at the proliferative stage. FIG. 9 illustrates up-regulated and de-regulated genes associated with endometriosis at the early secretory stage. FIG. 10 illustrates up-regulated genes associated with endometriosis at the mid to late secretory phase.

Discussion

The phase-specific endometriosis signatures identified using methods of the invention can be used as biomarkers for the disease and to guide course of treatment. Additional information can be correlated into the meta-analysis to obtain phase-specific endometriosis signatures associated with particular parameters, for example, age, stage of endometriosis, infertility, and other phenotypic traits. The clinical applications of the phase-specific endometriosis signatures are discussed hereinafter.

In certain embodiments, the phase-specific endometriosis signatures can be utilized to target diagnosis of endometriosis. For example, the expression levels of transcripts in one or more samples obtained from a patient suspected of having endometriosis can be compared to known phase-specific endometriosis signatures. The samples can be obtained at a particular phase or across several time-points of the patient's uterine cycle. The expression levels can be compared to signatures corresponding to one phase or diverse group of signatures from the various phases of the uterine cycle. Similarities between the patient's expression level and the phase-specific endometriosis signatures are the patient's phase-specific endometriosis signature and indicate that the patient has endometriosis. A course of treatment can be chosen that is tailored to the patient's phase-specific endometriosis signatures. For example, drugs may be recommended or prescribed to the patient to coincide with the phase in which the patient has endometriosis signatures. In addition, drugs may be recommended or prescribed to the patients that are known to target the gene or the biochemical pathways associated with the gene. In instances where the phase-specific endometriosis signatures is also keyed to a particular grade (i.e. severity) of endometriosis, the comparison between the patient's expression pattern and the endometriosis signatures may be indicative of the grade of the patient's endometriosis.

The phase-specific genetic signatures can also be applied to identify and chart the patient's specific uterine cycle. The uterine cycle is very individual specific-ranging between 21 days to 35 days, with the norm being 28 days. In addition, the length of the phases of the uterine cycle likewise varies among individuals. Since treatment of endometriosis may be implicated for certain phases, the ability to genetically confirm the phase of an individual to direct the timing of treatment is advantageous. According to methods of the invention, the patient's expression levels across different time-points can be compared phase-specific endometriosis signatures to determine the timing of the patient's uterine cycle. For instances, correlations between the patient's expression levels and signatures of a particular phase are indicative of the phase of the patient. Utilizing genetics to determine the timing of a patient's uterine cycle provides benefits such as being able to tailor treatment of a variety of reproductive conditions, including the treatment of infertility, premenstrual dysphoric disorder, and endometriosis. In various scenarios, a better understanding of the timing of one's uterine cycle provides greater insight into the hormonal state of the patient, which may guide hormone treatment regimens.

EXAMPLE 3

Though an effect of obesity on IVF success rate seems likely, there is disagreement about the precise nature of the relationship between these two parameters. Articles differ in their approach to address this question: Many of them focus on patients with specific infertility diagnoses, while others have no inclusion criteria. To determine how obesity affects IVF success rates for patients, and to determine whether this relationship differs between patients with different infertility diagnoses, relationships between obesity and an increased risk of IVF treatment failure were investigated among women with different infertility diagnoses. A retrospective analysis was employed using de-identified fresh and cryo-thawed self IVF cycles (N=5208, 2738 patients) from a large reproductive medical center.

Methods:

A Reproductive Medicine Associates of New York, LLP dataset of 5208 cycles was used for the analysis. Logistic regression models were created and controlled for age, day 3 follicle stimulating hormone (FSH), peak estradiol level, number of oocytes retrieved, number of embryos transferred, and whether intra-cytoplasmic sperm injection (ICSI) procedure was performed).

The infertility diagnoses included in the analysis were diminished ovarian reserve, endometriosis, idiopathic, male factor, PCOS, and tubal factor (Table 1).

TABLE 1

Sample information for diagnoses included

| diagnosis | cycles | obese cycles | patients | obese patients | % obese patients | p-value |
|---|---|---|---|---|---|---|
| Overall | 5208 | 648 | 2738 | 344 | 0.124 | |
| DOR | 1065 | 94 | 615 | 61 | 0.088 | 0.97 |
| Endometriosis | 327 | 13 | 170 | 9 | 0.04 | 0.99 |
| Idiopathic | 1347 | 140 | 705 | 66 | 0.104 | 1 |
| Male Factor | 1492 | 218 | 742 | 105 | 0.146 | 0.1 |
| PCOS | 439 | 93 | 223 | 47 | 0.212 | 0.0005 |
| Tubal Factor | 538 | 90 | 283 | 56 | 0.167 | 0.0006 |

(NB: p-value is obtained from a proportion-test, which checks if the proportion of obese patients for a given diagnosis is greater than in the data combining all six diagnoses.)

Results:

Both clinical pregnancy and live birth outcome were correlated with obesity across all patients, defining obesity as BMI 30 kg/m2 and non-obese as BMI<30 kg/m2. For data combining patients of all diagnoses, there was no correlation between obesity on clinical pregnancy [Table 2] or live birth outcome [Table 3].

The analysis of repeated, this time breaking the cohort down by diagnosis, comparing clinical pregnancy and live birth outcome rates, in relation to obesity. PCOS was found to be the only diagnosis in which a relationship between obesity and clinical pregnancy (OR=0.57, p=0.03) [Table 2], and live birth outcome (OR=0.44, p=0.02) exists [Table 3].

TABLE 2

Change in likelihood of Clinical Pregnancy outcome given presence of patient obesity.

| | Likelihood of Clinical Pregnancy if patient is obese | |
|---|---|---|
| Diagnosis | Odds Ratio | P-value |
| All Diagnoses | 1.08 | 0.43 |
| PCOS | 0.57 | 0.03 |
| Male Factor | 1.03 | 0.86 |
| DOR | 1.32 | 0.32 |
| Tubal Factor | 1.38 | 0.19 |
| Endometriosis | 1.07 | 0.92 |
| Idiopathic | 1.01 | 0.96 |

TABLE 3

Change in likelihood of Live Birth outcome given presence of patient obesity.

| | Likelihood of Live Birth if patient is obese | |
|---|---|---|
| Diagnosis | Odds Ratio | P-value |
| All Diagnoses | 0.95 | 0.71 |
| PCOS | 0.44 | 0.02 |
| Male Factor | 1.33 | 0.27 |
| DOR | 0.94 | 0.88 |
| Tubal Factor | 2.35 | 0.1 |
| Endometriosis | 0.74 | 0.72 |
| Idiopathic | 0.71 | 0.22 |

As a secondary analysis, a specific point along an IVF cycle was determined where the effects of obesity become significant. To do this, 'landmarks' such as number of oocytes retrieved, rates of embryo development, number of embryos transferred and implantation rate were correlated with obesity. This analysis was repeated using data subset for different common infertility diagnoses, to determine what parts of the cycle are most affected by obesity, for each diagnosis.

Since obesity was found to have an effect on all outcomes post ET in the PCOS population, further analysis was used to pinpoint where the effect manifested. To achieve that, implantation rate less than 50% (in addition to the standard confounding variables) was controlled for in the LB outcome analysis.

Obesity was not correlated significantly with any IVF cycle 'landmarks' between oocyte retrieval and embryo transfer, for any diagnosis. This result indicates that the effect of obesity on IVF outcome occurs after embryo transfer takes place.

Implantation rate was significantly adversely correlated with presence of obesity for PCOS patients, but not for other diagnoses. In investigating whether implantation rate less than 50% was correlated with obesity, it was determined that, for PCOS patients, Implantation Rate<50% was almost twice as likely if the patient was obese (OR=1.82, p=0.02) [Table 4]. This result supports the hypothesis that the influence of obesity on IVF success for PCOS patients occurs after embryo transfer.

TABLE 4

Likelihood of implantation rate less than 50%, given presence of patient obesity.

| Diagnosis | Likelihood of Implantation Rate < 50% if patient is obese | |
|---|---|---|
| | Odds Ratio | P-value |
| All Diagnoses | 0.95 | 0.61 |
| PCOS | 1.82 | 0.02 |

TABLE 4-continued

Likelihood of implantation rate less than 50%, given presence of patient obesity.

| Diagnosis | Likelihood of Implantation Rate < 50% if patient is obese | |
|---|---|---|
| | Odds Ratio | P-value |
| Male Factor | 0.85 | 0.33 |
| DOR | 0.76 | 0.42 |
| Tubal Factor | 0.63 | 0.06 |
| Endometriosis | 0.84 | 0.78 |
| Idiopathic | 1.30 | 0.77 |

Having found that obesity is correlated with reduced implantation rate for PCOS patients, it was then investigated whether the effect on live birth outcome occurred independently of its reduction of implantation rate, or if a reduced implantation rate was the source of the negative effect on Live Birth.

Analysis indicated that obesity's negative impact on implantation rate is the source of its negative effect on live birth, and not merely an independent effect.

TABLE 5

Effects of both 'implantation rate less than 50%' and obesity on live birth outcome for PCOS patients.

| | Effect on live birth outcome (PCOS patients) |
|---|---|
| obesity | OR = 0.53, p = 0.2 |
| implantation rate less than 50% | OR = 0.2, p < $10^{-9}$ |

Detailed Data for Example 3:

1) Clinical Outcomes

Retrieved~obese + SrgFollicleslessthanEq14 + Age + FSHMax + PeakE2

| diagnosis | effect (obese) | p-value (obese) | lwr | upr | n (cycles) | n (obese) |
|---|---|---|---|---|---|---|
| male factor | 1.09 | 0.02 | 1.02 | 1.16 | — | |
| PCOS | 0.9 | 0.07 | 0.81 | 1.01 | — | |
| Idiopathic | 1.07 | 0.14 | 0.98 | 1.16 | — | |
| Tubal Factor | 1 | 0.99 | 0.91 | 1.1 | — | |
| DOR | 1.02 | 0.7 | 0.9 | 1.16 | — | |
| endo-metriosis | 0.97 | 0.86 | 0.71 | 1.34 | — | |
| overall | 1.04 | 0.07 | 1 | 1.08 | 4513 | 567 | family = poisson
data includes Retrieved = 0
data includes EmbryosTransferred = 0
data excludes frozen cycles CountViable~obese + Retrieved + Age + FSHMax + PeakE2 + icsi + cryo

| diagnosis | effect (obese) | p-value (obese) | lwr | upr | n (cycles) | n (obese) |
|---|---|---|---|---|---|---|
| male factor | 1 | 0.99 | 0.91 | 1.1 | 1492 | 218 |
| PCOS | 0.9 | 0.16 | 0.78 | 1.04 | 439 | 93 |
| Idiopathic | 0.97 | 0.67 | 0.87 | 1.09 | 1347 | 140 |
| Tubal Factor | 1.13 | 0.06 | 1 | 1.29 | 538 | 90 |
| DOR | 0.91 | 0.21 | 0.78 | 1.06 | 1065 | 94 |
| endo-metriosis | 0.93 | 0.73 | 0.62 | 1.4 | 327 | 13 |

| 1) Clinical Outcomes | | | | | |
|---|---|---|---|---|---|
| overall | 1 | 0.92 | 0.95 | 1.06 | 5208 | 648 | family = poisson
data includes Retrieved = 0
data includes EmbryosTransferred = 0

EmbryosTransferred~obese + Age + FSHMax + PeakE2 + icsi + cryo

| diagnosis | effect (obese) | p-value (obese) | lwr | upr | n (cycles) | n (obese) |
|---|---|---|---|---|---|---|
| male factor | 1.1 | 0.02 | 1.02 | 1.19 | 1492 | 218 |
| PCOS | 0.99 | 0.82 | 0.88 | 1.11 | 439 | 93 |
| Idiopathic | 0.97 | 0.67 | 0.87 | 1.09 | 1347 | 140 |
| Tubal Factor | 0.98 | 0.72 | 0.87 | 1.1 | 538 | 90 |
| DOR | 0.88 | 0.12 | 0.75 | 1.03 | 1065 | 94 |
| endometriosis | 0.77 | 0.09 | 0.57 | 1.04 | 327 | 13 |
| overall | 1.03 | 0.28 | 0.98 | 1.08 | 5208 | 648 | family = poisson
data includes Retrieved = 0
data includes EmbryosTransferred = 0

ImplantationRatelessthan50~obese + Retrieved + EmbryosTransferred +
cryo + Age + FSHMax + PeakE2 + icsi

| diagnosis | OR (obese) | p-value (obese) | lwr | upr | n (cycles) | n (obese) |
|---|---|---|---|---|---|---|
| male factor | 0.85 | 0.33 | 0.61 | 1.18 | 1492 | 218 |
| PCOS | 1.81 | 0.02 | 1.11 | 2.96 | 439 | 93 |
| Idiopathic | 1.29 | 0.24 | 0.84 | 1.98 | 1347 | 140 |
| Tubal Factor | 0.63 | 0.06 | 0.38 | 1.02 | 538 | 90 |
| DOR | 0.76 | 0.42 | 0.39 | 1.47 | 1065 | 94 |
| endometriosis | 0.84 | 0.78 | 0.24 | 2.96 | 327 | 13 |
| overall | 0.84 | 0.78 | 0.24 | 2.96 | 5208 | 648 | family = binomial
data includes Retrieved = 0
data includes EmbryosTransferred = 0

ClinPregOutcome~obese + Retrieved + EmbryosTransferred +
cryo + Age + FSHMax + PeakE2 + icsi

| diagnosis | OR (obese) | p-value (obese) | lwr | upr | n (cycles) | n (obese) |
|---|---|---|---|---|---|---|
| male factor | 1.03 | 0.86 | 0.74 | 1.45 | 1492 | 218 |
| PCOS | 0.57 | 0.03 | 0.34 | 0.94 | 439 | 93 |
| Idiopathic | 1.01 | 0.96 | 0.69 | 1.48 | 1347 | 140 |
| Tubal Factor | 1.38 | 0.19 | 0.85 | 2.25 | 538 | 90 |
| DOR | 1.32 | 0.32 | 0.76 | 2.3 | 1065 | 94 |
| endometriosis | 1.07 | 0.92 | 0.28 | 4.17 | 327 | 13 |
| overall | 1.08 | 0.43 | 0.89 | 1.3 | 5208 | 648 | family = binomial
data includes Retrieved = 0
data includes EmbryosTransferred = 0

LiveBirthOutcome~obese + Retrieved + EmbryosTransferred +
cryo + Age + FSHMax + PeakE2 + icsi

| diagnosis | OR (obese) | p-value (obese) | lwr | upr | n (cycles) | n (obese) |
|---|---|---|---|---|---|---|
| male factor | 1.33 | 0.27 | 0.81 | 2.19 | 1492 | 218 |
| PCOS | 0.44 | 0.02 | 0.21 | 0.9 | 439 | 93 |
| Idiopathic | 0.71 | 0.22 | 0.41 | 1.22 | 1347 | 140 |
| Tubal Factor | 2.35 | 0.1 | 0.84 | 6.56 | 538 | 90 |

| 1) Clinical Outcomes | | | | | | |
|---|---|---|---|---|---|---|
| DOR | 0.94 | 0.88 | 0.43 | 2.05 | 1065 | 94 |
| endo-metriosis | 0.74 | 0.72 | 0.14 | 3.93 | 327 | 13 |
| overall | 0.95 | 0.71 | 0.72 | 1.25 | 5208 | 648 | family = binomial
data includes Retrieved = 0
data includes EmbryosTransferred = 0

AnyEmbryosTransferred~obese + Age + FSHMax + PeakE2 + icsi + cryo

| diagnosis | effect (obese) | p-value (obese) | lwr | upr | n (cycles) | n (obese) |
|---|---|---|---|---|---|---|
| male factor | 1.65 | 0.12 | 0.88 | 3.08 | 1492 | 218 |
| PCOS | 0.57 | 0.17 | 0.26 | 1.26 | 439 | 93 |
| Idiopathic | 0.96 | 0.88 | 0.55 | 1.69 | 1347 | 140 |
| Tubal Factor | 1.15 | 0.77 | 0.44 | 2.99 | 538 | 90 |
| DOR | 0.84 | 0.55 | 0.48 | 1.47 | 1065 | 94 |
| endo-metriosis | 0.48 | 0.39 | 0.09 | 2.54 | 327 | 13 |
| overall | 1.03 | 0.28 | 0.98 | 1.08 | 5208 | 648 | family = binomial
data includes Retrieved = 0
data includes EmbryosTransferred = 0

LB~obese + . . . + controlling for ImplantationRatelessthan50
LiveBirthOutcome~obese + Retrieved + EmbryosTransferred +
cryo + Age + FSHMax + PeakE2 + icsi + ImplantationRatelessthan50

| diagnosis | OR (obese) | p-value (obese) | lwr | upr | OR (imprateLT50) | p-value (imprateLT50) | lwr | upr | n (cycles) | n (obese) |
|---|---|---|---|---|---|---|---|---|---|---|
| male factor | 1.245 | 0.421 | 0.730 | 2.126 | 0.073 | 0.000 | 0.047 | 0.115 | 1492.000 | 218.000 |
| PCOS | 0.534 | 0.197 | 0.206 | 1.384 | 0.033 | 0.000 | 0.015 | 0.073 | 439.000 | 93.000 |
| Idiopathic | 0.964 | 0.914 | 0.497 | 1.870 | 0.051 | 0.000 | 0.030 | 0.087 | 1347.000 | 140.000 |
| Tubal Factor | 1.914 | 0.237 | 0.652 | 5.616 | 0.081 | 0.000 | 0.034 | 0.195 | 538.000 | 90.000 |
| DOR | 0.708 | 0.475 | 0.275 | 1.824 | 0.109 | 0.000 | 0.058 | 0.205 | 1065.000 | 94.000 |
| endo-metriosis | 0.406 | 0.194 | 0.104 | 1.581 | 0.081 | 0.000 | 0.035 | 0.190 | 327.000 | 13.000 |
| overall | 0.946 | 0.728 | 0.693 | 1.292 | 0.073 | 0.000 | 0.057 | 0.093 | 5208.000 | 648.000 | family = binomial
data includes Retrieved = 0
data includes EmbryosTransferred = 0

LiveBirthOutcome~obese + Retrieved + EmbryosTransferred +
cryo + Age + FSHMax + PeakE2 + icsi + ImplantationRatelessthan50

| diagnosis | OR (obese) | p (obese) | OR (imprate < 50) | p (imprate < 50) |
|---|---|---|---|---|
| male factor | 1.25 | 0.42 | 0.07 | $<10^{-9}$ |
| PCOS | 0.53 | 0.2 | 0.03 | $<10^{-9}$ |
| Idiopathic | 0.96 | 0.91 | 0.05 | $<10^{-9}$ |
| Tubal Factor | 1.91 | 0.24 | 0.08 | $<10^{-7}$ |
| DOR | 0.71 | 0.48 | 0.11 | $<10^{-9}$ |
| endo-metriosis | 0.41 | 0.19 | 0.08 | $<10^{-8}$ |
| overall | 0.95 | 0.73 | 0.07 | $<10^{-9}$ |

2) Oocyte/Embryo development outcomes (conditional on retrieval)

Countof2PN~obese + Retrieved + Age + FSHMax + PeakE2 + icsi

| diagnosis | effect (obese) | p-value (obese) | lwr | upr | n (cycles) | n (obese) |
|---|---|---|---|---|---|---|
| male factor | 0.98 | 0.53 | 0.91 | 1.05 | 1255 | 184 |
| PCOS | 0.93 | 0.19 | 0.84 | 1.04 | 332 | 77 |
| Idiopathic | 1.02 | 0.6 | 0.94 | 1.11 | 1176 | 123 |
| Tubal Factor | 1.11 | 0.01 | 1.03 | 1.21 | 456 | 81 |
| DOR | 1 | 0.96 | 0.86 | 1.15 | 1016 | 89 |
| endometriosis | 1.03 | 0.82 | 0.82 | 1.28 | 274 | 11 |
| overall | 1.01 | 0.5 | 0.97 | 1.06 | 4509 | 565 | family = poisson
data does not include Retrieved = 0
data includes EmbryosTransferred = 0

CountofDeg~obese + Retrieved + Age + FSHMax + PeakE2 + icsi

| diagnosis | effect (obese) | p-value (obese) | lwr | upr | n (cycles) | n (obese) |
|---|---|---|---|---|---|---|
| male factor | 1.09 | 0.44 | 0.88 | 1.35 | 1255 | 184 |
| PCOS | 1.49 | 0.08 | 0.96 | 2.32 | 332 | 77 |
| Idiopathic | 1.32 | 0.07 | 0.98 | 1.78 | 1176 | 123 |
| Tubal Factor | 1.21 | 0.28 | 0.85 | 1.72 | 456 | 81 |
| DOR | 0.89 | 0.61 | 0.58 | 1.37 | 1016 | 89 |
| endometriosis | 1.53 | 0.24 | 0.75 | 3.11 | 274 | 11 |
| overall | 1.16 | 0.04 | 1.01 | 1.33 | 4509 | 565 | family = poisson
data does not include Retrieved = 0
data includes EmbryosTransferred = 0

CountAbnormal~obese + Retrieved + Age + FSHMax + PeakE2 + icsi

| diagnosis | effect (obese) | p-value (obese) | lwr | upr | n (cycles) | n (obese) |
|---|---|---|---|---|---|---|
| male factor | 1.05 | 0.7 | 0.81 | 1.37 | 1255 | 184 |
| PCOS | 1.07 | 0.67 | 0.78 | 1.48 | 332 | 77 |
| Idiopathic | 1 | 0.97 | 0.8 | 1.23 | 1176 | 123 |
| Tubal Factor | 0.96 | 0.79 | 0.73 | 1.27 | 456 | 81 |
| DOR | 1.08 | 0.61 | 0.8 | 1.47 | 1016 | 89 |
| endometriosis | 0.78 | 0.5 | 0.38 | 1.6 | 274 | 11 |
| overall | 1.03 | 0.6 | 0.92 | 1.16 | 4509 | 565 | family = poisson
data does not include Retrieved = 0
data includes EmbryosTransferred = 0

3) Oocyte/Embryo development outcomes (conditional on retrieval, grouped on retrieved)

binary_Countof2PN~obese + Age + FSHMax + PeakE2 + Retrieved + icsi

| diagnosis | effect (obese) | p-value (obese) | lwr | upr | n (cycles) | n (obese) |
|---|---|---|---|---|---|---|
| male factor | 1.03 | 0.69 | 0.89 | 1.19 | 1255 | 184 |
| PCOS | 0.89 | 0.38 | 0.69 | 1.15 | 332 | 77 |
| Idiopathic | 0.99 | 0.95 | 0.84 | 1.17 | 1176 | 123 |
| Tubal Factor | 1.38 | 0 | 1.14 | 1.68 | 456 | 81 |
| DOR | 0.97 | 0.84 | 0.7 | 1.33 | 1016 | 89 |
| endometriosis | 1.22 | 0.44 | 0.73 | 2.03 | 274 | 11 | family = binomial
data does not include Retrieved = 0
data includes Embryos Transferred = 0 binary_CountofDeg~obese + Age + FSHMax + PeakE2 + Retrieved + icsi

| diagnosis | effect (obese) | p-value (obese) | lwr | upr | n (cycles) | n (obese) |
|---|---|---|---|---|---|---|
| male factor | 1.18 | 0.19 | 0.92 | 1.52 | 1255 | 184 |
| PCOS | 1.73 | 0.04 | 1.02 | 2.96 | 332 | 77 |
| Idiopathic | 1.13 | 0.54 | 0.76 | 1.68 | 1176 | 123 |
| Tubal Factor | 1.08 | 0.72 | 0.7 | 1.67 | 456 | 81 |
| DOR | 0.88 | 0.63 | 0.54 | 1.45 | 1016 | 89 |
| endometriosis | 1.54 | 0.29 | 0.69 | 3.43 | 274 | 11 | family = binomial
data does not include Retrieved = 0
data includes EmbryosTransferred = 0 binary_CountofAbnormal~obese + Age + FSHMax + PeakE2 + Retrieved + icsi

| diagnosis | effect (obese) | p-value (obese) | lwr | upr | n (cycles) | n (obese) |
|---|---|---|---|---|---|---|
| male factor | 1.03 | 0.83 | 0.76 | 1.4 | 1255 | 184 |
| PCOS | 1.18 | 0.39 | 0.81 | 1.71 | 332 | 77 |
| Idiopathic | 0.97 | 0.81 | 0.74 | 1.26 | 1176 | 123 |
| Tubal Factor | 0.97 | 0.87 | 0.71 | 1.33 | 456 | 81 |
| DOR | 1.16 | 0.43 | 0.8 | 1.68 | 1016 | 89 |
| endometriosis | 0.93 | 0.8 | 0.52 | 1.66 | 274 | 11 | family = binomial
data does not include Retrieved = 0
data includes EmbryosTransferred = 0

4) Oocyte/Embryo development outcomes (conditional on retrieval)

Countof2PN~obese + Retrieved + Age + FSHMax + PeakE2 + icsi + CountofM2

| diagnosis | effect (obese) | p-value (obese) | lwr | upr | n (cycles) | n (obese) |
|---|---|---|---|---|---|---|
| male factor | 0.97 | 0.49 | 0.9 | 1.05 | 1255 | 184 |
| PCOS | 0.94 | 0.2 | 0.85 | 1.04 | 332 | 77 |
| Idiopathic | 1.03 | 0.52 | 0.95 | 1.12 | 1176 | 123 |
| Tubal Factor | 1.11 | 0.01 | 1.02 | 1.21 | 456 | 81 |
| DOR | 0.99 | 0.94 | 0.86 | 1.14 | 1016 | 89 |
| endometriosis | 1.01 | 0.91 | 0.81 | 1.26 | 274 | 11 |
| overall | 1.01 | 0.59 | 0.97 | 1.05 | 4509 | 565 | family = poisson
data does not include Retrieved = 0
data includes EmbryosTransferred = 0

4) Oocyte/Embryo development outcomes (conditional on retrieval)

CountofDeg~obese + Retrieved + Age + FSHMax + PeakE2 + icsi + CountofM2

| diagnosis | effect (obese) | p-value (obese) | lwr | upr | n (cycles) | n (obese) |
|---|---|---|---|---|---|---|
| male factor | 1.09 | 0.44 | 0.88 | 1.35 | 1255 | 184 |
| PCOS | 1.49 | 0.07 | 0.97 | 2.28 | 332 | 77 |
| Idiopathic | 1.31 | 0.08 | 0.97 | 1.77 | 1176 | 123 |
| Tubal Factor | 1.29 | 0.12 | 0.94 | 1.78 | 456 | 81 |
| DOR | 0.91 | 0.67 | 0.6 | 1.39 | 1016 | 89 |
| endometriosis | 1.55 | 0.24 | 0.75 | 3.18 | 274 | 11 |
| overall | 1.16 | 0.03 | 1.01 | 1.34 | 4509 | 565 | family = poisson
data does not include Retrieved = 0
data includes EmbryosTransferred = 0

4) Oocyte/Embryo development outcomes (conditional on retrieval)

CountAbnormal~obese + Retrieved + Age + FSHMax + PeakE2 + icsi + CountofM2

| diagnosis | effect (obese) | p-value (obese) | lwr | upr | n (cycles) | n (obese) |
|---|---|---|---|---|---|---|
| male factor | 1.05 | 0.69 | 0.81 | 1.37 | 1255 | 184 |
| PCOS | 1.06 | 0.71 | 0.77 | 1.47 | 332 | 77 |
| Idiopathic | 1 | 0.99 | 0.81 | 1.24 | 1176 | 123 |
| Tubal Factor | 0.95 | 0.74 | 0.72 | 1.26 | 456 | 81 |
| DOR | 1.08 | 0.61 | 0.8 | 1.47 | 1016 | 89 |
| endometriosis | 0.68 | 0.3 | 0.33 | 1.41 | 274 | 11 |
| overall | 1.03 | 0.64 | 0.91 | 1.16 | 4509 | 565 | family = poisson
data does not include Retrieved = 0
data includes EmbryosTransferred = 0

5) Oocyte/Embryo development outcomes (conditional on retrieval, grouped on MII)

binary_Countof2PN~obese + Age + FSHMax + PeakE2 + Retrieved + icsi

| diagnosis | effect (obese) | p-value (obese) | lwr | upr | n (cycles) | n (obese) |
|---|---|---|---|---|---|---|
| male factor | 0.94 | 0.68 | 0.71 | 1.25 | 1255 | 184 |
| PCOS | 0.8 | 0.37 | 0.49 | 1.3 | 332 | 77 |
| Idiopathic | 0.89 | 0.44 | 0.67 | 1.19 | 1176 | 123 |
| Tubal Factor | 1.41 | 0.05 | 1 | 1.98 | 456 | 81 |
| DOR | 0.8 | 0.35 | 0.5 | 1.28 | 1016 | 89 |
| endometriosis | 0.75 | 0.18 | 0.49 | 1.14 | 274 | 11 | family = binomial
data does not include Retrieved = 0
data includes EmbryosTransferred = 0 binary_CountofDeg~obese + Age + FSHMax + PeakE2 + Retrieved + icsi

| diagnosis | effect (obese) | p-value (obese) | lwr | upr | n (cycles) | n (obese) |
|---|---|---|---|---|---|---|
| male factor | 1.3 | 0.08 | 0.97 | 1.76 | 1255 | 184 |
| PCOS | 1.27 | 0.32 | 0.79 | 2.05 | 332 | 77 |
| Idiopathic | 1.48 | 0.1 | 0.93 | 2.37 | 1176 | 123 |
| Tubal Factor | 1.08 | 0.74 | 0.69 | 1.7 | 456 | 81 |
| DOR | 0.68 | 0.32 | 0.32 | 1.44 | 1016 | 89 |
| endometriosis | 1.32 | 0.5 | 0.59 | 2.98 | 274 | 11 | family = binomial
data does not include Retrieved = 0
data includes EmbryosTransferred = 0 binary_CountofAbnormal~obese + Age + FSHMax + PeakE2 + Retrieved + icsi

| diagnosis | effect (obese) | p-value (obese) | lwr | upr | n (cycles) | n (obese) |
|---|---|---|---|---|---|---|
| male factor | 1.12 | 0.61 | 0.73 | 1.7 | 1255 | 184 |
| PCOS | 1.18 | 0.39 | 0.81 | 1.71 | 332 | 77 |
| Idiopathic | 1.02 | 0.87 | 0.77 | 1.35 | 1176 | 123 |
| Tubal Factor | 0.87 | 0.51 | 0.58 | 1.31 | 456 | 81 |

-continued

| 5) Oocyte/Embryo development outcomes (conditional on retrieval, grouped on MII) | | | | | | |
|---|---|---|---|---|---|---|
| DOR | 1.15 | 0.6 | 0.68 | 1.93 | 1016 | 89 |
| endo-metriosis | 0.96 | 0.9 | 0.5 | 1.83 | 274 | 11 | family = binomial
data does not include Retrieved = 0
data includes EmbryosTransferred = 0

Implantation Rates impl.rate = ImplatationRatePerSac >= threshold
impl.rate~obese + Retrieved + EmbryosTransferred +
cryo + Age + FSHMax + PeakE2 + icsi

| PCOS | threshold | OR | p-val |
|---|---|---|---|
| 1 | 0.1 | 0.565 | 0.026 |
| 2 | 0.2 | 0.58 | 0.033 |
| 3 | 0.3 | 0.566 | 0.023 |
| 4 | 0.4 | 0.551 | 0.017 |
| 5 | 0.5 | 0.551 | 0.017 |
| 6 | 0.6 | 0.39 | 0.003 |
| 7 | 0.7 | 0.409 | 0.006 |
| 8 | 0.8 | 0.409 | 0.006 |
| 9 | 0.9 | 0.414 | 0.007 | family = binomial
data does includes Retrieved = 0
data includes EmbryosTransferred = 0
impl.rate = ImplatationRatePerSac >= threshold
impl.rate~obese + Retrieved + EmbryosTransferred +
cryo + Age + FSHMax + PeakE2 + icsi

| Male Factor | threshold | OR | p-val |
|---|---|---|---|
| 1 | 0.1 | 1.041 | 0.816 |
| 2 | 0.2 | 1.032 | 0.854 |
| 3 | 0.3 | 1.085 | 0.625 |
| 4 | 0.4 | 1.218 | 0.245 |
| 5 | 0.5 | 1.179 | 0.332 |
| 6 | 0.6 | 1.453 | 0.041 |
| 7 | 0.7 | 1.405 | 0.093 |
| 8 | 0.8 | 1.451 | 0.069 |
| 9 | 0.9 | 1.451 | 0.069 | family = binomial
data does includes Retrieved = 0
data includes EmbryosTransferred = 0
impl.rate = ImplatationRatePerSac >= threshold
impl.rate~obese + Retrieved + EmbryosTransferred +
cryo + Age + FSHMax + PeakE2 + icsi

| Idiopathic | imp.threshold | imp.OR | imp.pvals |
|---|---|---|---|
| 1 | 0.1 | 0.982 | 0.927 |
| 2 | 0.2 | 0.936 | 0.735 |
| 3 | 0.3 | 0.842 | 0.393 |
| 4 | 0.4 | 0.774 | 0.238 |
| 5 | 0.5 | 0.774 | 0.242 |
| 6 | 0.6 | 0.633 | 0.108 |
| 7 | 0.7 | 0.753 | 0.362 |
| 8 | 0.8 | 0.656 | 0.2 |
| 9 | 0.9 | 0.662 | 0.211 | family = binomial
data does includes Retrieved = 0
data includes EmbryosTransferred = 0
impl.rate = ImplatationRatePerSac >= threshold
impl.rate~obese + Retrieved + EmbryosTransferred +
cryo + Age + FSHMax + PeakE2 + icsi

| Tubal Factor | imp.threshold | imp. OR | imp.pvals |
|---|---|---|---|
| 1 | 0.1 | 1.395 | 0.179 |
| 2 | 0.2 | 1.395 | 0.179 |
| 3 | 0.3 | 1.241 | 0.38 |
| 4 | 0.4 | 1.55 | 0.079 |
| 5 | 0.5 | 1.598 | 0.062 |
| 6 | 0.6 | 1.259 | 0.459 |
| 7 | 0.7 | 1.2 | 0.596 |
| 8 | 0.8 | 1.2 | 0.596 |

5) Oocyte/Embryo development outcomes (conditional on retrieval, grouped on MII)

| | 9 | 0.9 | 1.2 | 0.596 |
|---|---|---|---|---| family = binomial  
data does includes Retrieved = 0  
data includes EmbryosTransferred = 0  
impl.rate = ImplatationRatePerSac >= threshold  
impl.rate~obese + Retrieved + EmbryosTransferred + cryo + Age + FSHMax + PeakE2 + icsi

| DOR | imp.threshold | imp.OR | imp.pvals |
|---|---|---|---|
| | 1 | 0.1 | 1.32 | 0.315 |
| | 2 | 0.2 | 1.372 | 0.248 |
| | 3 | 0.3 | 1.299 | 0.37 |
| | 4 | 0.4 | 1.321 | 0.395 |
| | 5 | 0.5 | 1.316 | 0.416 |
| | 6 | 0.6 | 1.384 | 0.459 |
| | 7 | 0.7 | 1.886 | 0.164 |
| | 8 | 0.8 | 1.713 | 0.267 |
| | 9 | 0.9 | 1.713 | 0.267 | family = binomial  
data does includes Retrieved = 0  
data includes EmbryosTransferred = 0  
impl.rate = ImplatationRatePerSac >= threshold  
impl.rate~obese + Retrieved + EmbryosTransferred + cryo + Age + FSHMax + PeakE2 + icsi

| Endometriosis | imp.threshold | imp.OR | imp.pvals |
|---|---|---|---|
| | 1 | 0.1 | 0.968 | 0.962 |
| | 2 | 0.2 | 0.93 | 0.914 |
| | 3 | 0.3 | 0.984 | 0.981 |
| | 4 | 0.4 | 1.192 | 0.782 |
| | 5 | 0.5 | 1.192 | 0.785 |
| | 6 | 0.6 | 2.21 | 0.251 |
| | 7 | 0.7 | 2.572 | 0.176 |
| | 8 | 0.8 | 2.591 | 0.178 |
| | 9 | 0.9 | 2.591 | 0.178 | family = binomial  
data does includes Retrieved = 0  
data includes EmbryosTransferred = 0  
impl.rate = ImplatationRatePerSac >= threshold  
impl.rate~obese + Retrieved + EmbryosTransferred + cryo + Age + FSHMax + PeakE2 + icsi

| Endometriosis | imp.threshold | imp.OR | imp.pvals |
|---|---|---|---|
| | 1 | 0.1 | 1.072 | 0.461 |
| | 2 | 0.2 | 1.056 | 0.565 |
| | 3 | 0.3 | 1.022 | 0.819 |
| | 4 | 0.4 | 1.055 | 0.589 |
| | 5 | 0.5 | 1.052 | 0.614 |
| | 6 | 0.6 | 1.028 | 0.815 |
| | 7 | 0.7 | 1.071 | 0.597 |
| | 8 | 0.8 | 1.056 | 0.68 |
| | 9 | 0.9 | 1.061 | 0.653 | family = binomial  
data does includes Retrieved = 0  
data includes EmbryosTransferred = 0

Sample Information

| Sample Info diagnosis | cycles | obese cycles | patients | obese patients | % obese patients | p-value |
|---|---|---|---|---|---|---|
| all | 5208 | 648 | 2738 | 344 | 0.124 | |
| DOR | 1065 | 94 | 615 | 61 | 0.088 | 0.97 |
| Endometriosis | 327 | 13 | 170 | 9 | 0.04 | 0.99 |
| Idiopathic | 1347 | 140 | 705 | 66 | 0.104 | 1 |
| Male Factor | 1492 | 218 | 742 | 105 | 0.146 | 0.1 |
| PCO | 439 | 93 | 223 | 47 | 0.212 | 0.0005 |
| Tubal Factor | 538 | 90 | 283 | 56 | 0.167 | 0.0006 |

| 5) Oocyte/Embryo development outcomes (conditional on retrieval, grouped on MII) | | |
|---|---|---| percentage is number of obese patients for given diagnosis/number of patients for that diagnosis
p-value is from proportion test: proportion of obese overall to proportion of obese in diagnosis
use one-sided alternative hypothesis for prop.test

| | effect | p-val |
|---|---|---|
| PCOS | | |
| Count ooc. retrieved | 0.9 | 0.07 |
| Count viable embryos | 0.9 | 0.16 |
| embryos transferred? | 0.99 | 0.82 |
| implantation rate < 0.5? | 1.81 | 0.02 |
| clinical pregnancy? | 0.57 | 0.03 |
| live birth? | 0.44 | 0.02 |
| Male Factor | | |
| Count ooc. retrieved | 1.09 | 0.02 |
| Count viable embryos | 1 | 0.99 |
| embryos transferred? | 1.1 | 0.02 |
| implantation rate < 0.5? | 0.85 | 0.33 |
| clinical pregnancy? | 1.03 | 0.86 |
| live birth? | 1.33 | 0.27 |

| | OR (obese) | p (obese) | OR (imprate < 50) | p (imprate < 50) |
|---|---|---|---|---|
| odds ratio p-value | 0.53 dominant effect on implantation rate < 50%: obesity | 0.2 dominant effect on Live Birth outcome implantation rate less than 50% | 0.03 | <$10^{-9}$ |

| | effect on implantation rate less than 50% | |
|---|---|---|
| obesity | OR = 1.81, p = 0.02 | |

| | effect on live birth outcome (PCOS patients) | |
|---|---|---|
| obesity | OR = 0.53, p = 0.2 | |
| implantation rate less than 50% | OR = 0.2, p < $10^{-9}$ | |

| | effect on 'implantation rate less than 50%' | effect on live birth outcome |
|---|---|---|
| obesity | OR = 1.81, p = 0.02 | OR = 0.53, p = 0.2 |
| implantation rate less than 50% | NA | OR = 0.2, p < $10^{-9}$ |

Example 4

High aneuploidy rates are often associated with poor oocyte and embryo quality, both of which decrease with age. As with aneuploidy, FSH levels also rise with age; however, no direct link has been demonstrated between FSH levels and aneuploidy. A large cohort of retrospective pre-implantation genetic screening (PGS) data was studied to clarify the respective contributions of FSH and age to aneuploidy.

Patients analyzed included those with partners of normal karyotype, who underwent fresh in vitro fertilization (IVF) cycles in which 1 oocyte was retrieved, PGS was performed, and day 3 FSH levels were known for the cycle. The effects of patients' age and FSH levels (assessed both as a continuous variable and above/below a threshold of 13 mUI/mL) were correlated with aneuploidy status using generalized estimation equation (GEE) models.

A total of 462 patients with 2207 embryos were analyzed. Overall, patients with normal ploidy were younger (35.5±4.0 vs. 38.1±4.4) and had a lower basal FSH level (7.56±3.6 vs. 8.1±3.5) compared to those with aneuploidy. The odds of aneuploidy increased by 10% for each year of a woman's reproductive lifespan (OR=1.1, p<0.0001). No independent contribution of FSH levels to odds of aneuploidy was found when assessed as a continuous variable (p=0.75) or when considered above a threshold of 13 (p=0.45). However, it was observed that for women with FSH levels above 13 mUI/mL, their odds of aneuploidy increased at a substantially higher rate (50%) for each additional year (OR=1.52, p<0.0001) of life.

The findings suggest that equivalent FSH levels should not be directly equated with egg quality in women of different age. This has significant implications for the management of infertility in younger women with elevated FSH levels. Also, these women might benefit from earlier treatment intervention and egg/embryo banking, given that their odds of aneuploidy rise more rapidly over time than women of the same age without elevated FSH levels.

What is claimed is:

1. A method for assessing endometriosis, the method comprising:
   sequencing nucleic acid obtained from a tissue sample to determine levels of transcripts of a plurality of genes present in a tissue sample obtained from a subject suspected of having endometriosis, the plurality of genes comprising CCL 3L 1, CCL 3, FAM 180A, THBS 2, PDGFRL, FN 1, CLE 11A, CCNA 2, KIF 20A, BUB 1B, HSD 17B 6, HSD 11B 1, C 7, C 3, CXCL 2, CXCL 12, CXCL 13, PDGFC, CXCL 14, ACTA 2, TAGLN, ROBO 3, MT 1M, and SORBS 1;
   analyzing said levels against a reference regulation pattern specific to a time-point in a uterine cycle using a computer system having a processor, thereby to generate a patient-specific signature;
   preparing a report characterizing an endometriosis status of the subject based upon said patient-specific signature; and
   treating the subject with an effective amount of drugs specific to the patient-specific signature;
   wherein the reference regulation pattern is generated using gene expression data obtained from the plurality of genes across each phase of the uterine cycle from a reference population that includes both normal patients and endometriosis patients.

2. The method of claim 1, wherein the time-point comprises a phase in the uterine cycle.

3. The method of claim 2, wherein the phase is selected from the group consisting of the menstruation phase, the proliferative phase, the early secretory phase, the midsecretory phase, and the late secretory phase.

4. The method of claim 1, wherein the tissue comprises endometrial tissue.

5. The method of claim 4, wherein the endometrial tissue is ectopic, eutopic, or both.

6. The method of claim 5, wherein the regulation pattern is specific to ectopic tissue, eutopic tissue, or both.

7. The method of claim 1, wherein the regulation pattern comprises one or more transcripts selected from the group consisting of de-regulated transcripts, up-regulated transcripts, and combinations thereof.

8. The method of claim 1, wherein the characterizing step comprises determining the subject's phase in the uterine cycle.

9. The method of claim 8, wherein the treatment is based on the subject's phase in the uterine cycle.

10. A method for assessing endometriosis in a subject, the method comprising:
    sequencing nucleic acid obtained from a blood sample to determine levels of transcripts of a plurality of genes expressed by the subject across different time-points of the subject's uterine cycle, the plurality of genes comprising CCL 3L 1, CCL 3, FAM 180A, THBS 2, PDGFRL, FN 1, CLE 11A, CCNA 2, KIF 20A, BUB 1B, HSD 17B 6, HSD 11B 1, C 7, C 3, CXCL 2, CXCL 12, CXCL 13, PDGFC, CXCL 14, ACTA 2, TAGLN, ROBO 3, MT 1M, and SORBS 1;
    analyzing the determined transcript levels against reference transcript signatures corresponding to the different time-points of the uterine cycle using a computer system having a processor, wherein the reference transcript signatures are generated using gene expression data obtained from the plurality of genes across each phase of the uterine cycle from a reference population that includes both normal patients and endometriosis patients;
    generating, using the computer system, a patient-specific genetic signature for endometriosis at each time-point based on differential transcripts of the genes determined from the analyzing step;
    classifying endometriosis based on the patient-specific genetic signature; and
    treating the subject with a treatment specific to the patient-specific signature, wherein the treatment comprises administering an effective amount of vitamins or drugs.

11. The method of claim 10, wherein the different time-points comprise the phases of the subject's uterine cycle.

12. The method of claim 11, wherein the different phases are selected from the group consisting of the menstruation phase, the proliferative phase, the early secretory phase, the midsecretory phase, and the late secretory phase.

13. The method of claim 10, wherein the classifying step comprises determining the type of the endometriosis.

14. The method of claim 13, wherein the type of endometriosis is selected from the group consisting of subtle, typical, cystic ovarian, and deep.

15. The method of claim 10, wherein the treatment comprises applying a therapy during a time-point in which a differential transcript was identified.

16. The method of claim 10 wherein the sample comprises endometrial tissue.

17. The method of claim 16, wherein the endometrial tissue is ectopic, eutopic or both.

* * * * *